United States Patent
Lai et al.

(10) Patent No.: US 11,617,760 B2
(45) Date of Patent: *Apr. 4, 2023

(54) SAFE LENTIVIRAL VECTORS FOR TARGETED DELIVERY OF MULTIPLE THERAPEUTIC MOLECULES

(71) Applicant: American Gene Technologies International Inc., Rockville, MD (US)

(72) Inventors: Zhennan Lai, Rockville, MD (US); Jeffrey A. Galvin, Rockville, MD (US)

(73) Assignee: American Gene Technologies International Inc., Rockville, MD (US)

( * ) Notice: Subject to any disclaimer, the term of this patent is extended or adjusted under 35 U.S.C. 154(b) by 9 days.

This patent is subject to a terminal disclaimer.

(21) Appl. No.: 17/228,301

(22) Filed: Apr. 12, 2021

(65) Prior Publication Data

US 2021/0401868 A1 Dec. 30, 2021

Related U.S. Application Data

(60) Continuation of application No. 16/687,525, filed on Nov. 18, 2019, now Pat. No. 11,007,209, which is a division of application No. 13/333,882, filed on Dec. 21, 2011, now Pat. No. 10,548,914, which is a continuation of application No. 12/581,871, filed on Oct. 19, 2009, now abandoned.

(60) Provisional application No. 61/243,121, filed on Sep. 16, 2009, provisional application No. 61/116,138, filed on Nov. 19, 2008, provisional application No. 61/196,457, filed on Oct. 17, 2008.

(51) Int. Cl.
| | |
|---|---|
| A61K 31/7088 | (2006.01) |
| C07K 14/47 | (2006.01) |
| C12N 15/86 | (2006.01) |
| C12N 15/113 | (2010.01) |
| A61K 48/00 | (2006.01) |

(52) U.S. Cl.
CPC ...... *A61K 31/7088* (2013.01); *C07K 14/4746* (2013.01); *C12N 15/1135* (2013.01); *C12N 15/86* (2013.01); *A61K 48/00* (2013.01); *C07K 2319/10* (2013.01); *C12N 2310/14* (2013.01); *C12N 2320/32* (2013.01); *C12N 2330/51* (2013.01); *C12N 2740/16043* (2013.01); *C12N 2830/008* (2013.01); *C12N 2830/20* (2013.01)

(58) Field of Classification Search
CPC .......... C12N 15/1137; C12N 2310/141; C12N 2310/531; C12N 15/1135; C12N 15/86; C12N 2310/14; C12N 2320/32; C12N 2330/51; C12N 2740/16043; C12N 2830/008; C12N 2830/20; A61P 15/00; A61K 31/7088; A61K 48/00; C07K 14/4746; C07K 2319/10
See application file for complete search history.

(56) References Cited

U.S. PATENT DOCUMENTS

| | | |
|---|---|---|
| 5,674,703 A | 10/1997 | Woo et al. |
| 6,156,514 A | 12/2000 | Acevedo et al. |
| 6,399,383 B1 | 6/2002 | Apt et al. |
| 6,635,472 B1 | 10/2003 | Lauermann |
| 7,371,542 B2 | 5/2008 | Ivanova et al. |
| 9,527,904 B2 | 12/2016 | Balazs et al. |
| 9,834,791 B2 | 12/2017 | Zhang et al. |
| 10,233,464 B2 | 3/2019 | Panza et al. |
| 10,548,914 B2* | 2/2020 | Lai ..................... C07K 14/4746 |
| 11,007,209 B2* | 5/2021 | Lai ......................... A61P 35/00 |
| 2003/0013196 A1 | 1/2003 | Engelman et al. |
| 2003/0096787 A1 | 5/2003 | Perridcaudet et al. |
| 2003/0119770 A1 | 6/2003 | Lai |
| 2004/0161412 A1 | 8/2004 | Penn et al. |
| 2004/0192629 A1 | 9/2004 | Xu et al. |
| 2004/0214158 A1 | 10/2004 | Sethi et al. |
| 2004/0248296 A1 | 12/2004 | Beresford et al. |
| 2005/0019927 A1 | 1/2005 | Markus et al. |
| 2006/0183230 A1 | 8/2006 | Silla et al. |
| 2007/0026521 A1 | 2/2007 | Colosi |
| 2007/0141679 A1 | 6/2007 | Sodroski |
| 2007/0203333 A1 | 8/2007 | McSwiggen et al. |

(Continued)

FOREIGN PATENT DOCUMENTS

| | | |
|---|---|---|
| BR | 2515 | 3/2019 |
| EP | 3468617 | 4/2019 |

(Continued)

OTHER PUBLICATIONS

Vargas, J. Jr. et al., "Conditionally replicating lentiviral-hybrid episomal vectors for suicide gene therapy," Antiviral Res. Dec. 2008 vol. 80 No. 3, pp. 288-294.

GenBank Accession No. S60559 "(long control region) [human papillomavirus, type 16, Genomic, 860 nt]" May 7, 1993 [located online Nov. 21, 2017 at https://ncbi.nlm.nih.gov/nuccore/S60559] entire DNA sequence.

(Continued)

*Primary Examiner* — J. E. Angell
(74) *Attorney, Agent, or Firm* — DLA Piper LLP (US)

(57) ABSTRACT

The present application discloses a lentiviral transfer system which includes: (i) a self-inactivating transfer vector comprising: multiple gene units, wherein each gene unit includes a heterologous nucleic acid sequence operably linked to a regulatory nucleic acid sequence; and (ii) a helper construct which lacks a 5' LTR, wherein the 5' LTR has been replaced with a heterologous promoter, in which the helper construct further comprises: a lentiviral env nucleic acid sequence containing a deletion, wherein the deleted env nucleic acid sequence does not produce functional env protein; and a packaging signal contains a deletion, wherein the deleted packaging signal is nonfunctional.

14 Claims, 50 Drawing Sheets

Specification includes a Sequence Listing.

(56) References Cited

U.S. PATENT DOCUMENTS

| | | |
|---|---|---|
| 2008/0003225 A1 | 1/2008 | Vie et al. |
| 2008/0003682 A1 | 1/2008 | Lois-Caballe et al. |
| 2008/0131940 A1 | 6/2008 | Chiu |
| 2008/0153737 A1 | 6/2008 | Lieberman et al. |
| 2008/0227736 A1 | 9/2008 | Chen et al. |
| 2009/0304688 A1 | 12/2009 | Fournie et al. |
| 2010/0017911 A1 | 1/2010 | Dawson et al. |
| 2010/0119511 A1 | 5/2010 | Wang et al. |
| 2010/0120155 A1 | 5/2010 | Brennan et al. |
| 2011/0207226 A1 | 8/2011 | Ni et al. |
| 2012/0114607 A1 | 5/2012 | Lai et al. |
| 2013/0142766 A1 | 6/2013 | Dodo et al. |
| 2013/0122380 A1 | 8/2013 | Aquino et al. |
| 2014/0155468 A1 | 6/2014 | Gregory et al. |
| 2014/0234958 A1 | 8/2014 | Kashara et al. |
| 2014/0248277 A1 | 9/2014 | Hoffman et al. |
| 2014/0336245 A1 | 11/2014 | Mingozzi et al. |
| 2015/0010578 A1 | 1/2015 | Balazs et al. |
| 2015/0018539 A1 | 1/2015 | Fellmann |
| 2015/0176006 A1 | 6/2015 | Krause et al. |
| 2016/0243169 A1 | 8/2016 | Chen et al. |
| 2018/0161455 A1 | 6/2018 | Panza |
| 2020/0155590 A1 | 5/2020 | Zhennan |

FOREIGN PATENT DOCUMENTS

| | | |
|---|---|---|
| EP | 3468618 | 4/2019 |
| IN | 201947000153 | 2/2019 |
| JP | 2002506652 | 3/2002 |
| JP | 2008518591 | 6/2008 |
| JP | 2012508591 | 4/2012 |
| WO | WO 99/21979 | 5/1999 |
| WO | 199947691 | 9/1999 |
| WO | 2002020554 | 3/2002 |
| WO | 2004053137 | 6/2004 |
| WO | 2005033282 | 4/2005 |
| WO | 2006048215 | 5/2006 |
| WO | 2007000668 | 1/2007 |
| WO | 2007133674 | 11/2007 |
| WO | 2009100928 | 8/2009 |
| WO | 2009147445 | 12/2009 |
| WO | 2010051521 | 5/2010 |
| WO | 2010117974 | 10/2010 |
| WO | 2010127166 | 11/2010 |
| WO | 2011008348 | 1/2011 |
| WO | 2011071476 | 6/2011 |
| WO | 2011119942 | 9/2011 |
| WO | 2012061075 | 5/2012 |
| WO | 2014187881 | 11/2014 |
| WO | 2015078999 | 6/2015 |
| WO | 2016200997 | 7/2016 |
| WO | 2017213697 | 12/2017 |
| WO | 2017214327 | 12/2017 |

OTHER PUBLICATIONS

Zufferey et al., "Self-Inactivating Lentivirus Vector for Safe and Efficient In Vivo Gene Delivery," Journal of Virology, vol. 72(12), pp. 9873-9880, (1998).

Gorziglia et al., "Elimination of Both E1 and E2A from Adenovirus Vectors Further Improves Prospects for In Vivo Human gene Therapy," Journal of Virology, vol. 70(6), pp. 4173-4178, (1996).

Vargas et al., "Novel Integrase-Defective Lentiviral Episomal Vectors for Gene Transfer," Human Gene Therapy, vol. 15(4), pp. 361-372, (Apr. 2004).

Wendelburg et al., "An Enhanced EBNA1 Variant with reduced IR3 Domain for Long-Term Episomal Maintenance and Transgene Expression of ORIP-Based Plasmids in Human Cells," Gene Therapy, vol. 5, pp. 1389-1399, (Oct. 1998).

Westerhout et al., "A Conditionally Replicating HIV-Based Vector that Stably Expresses an Antiviral shRNA Against HIV-1 Replication," Molecular Therapy: The Journal of the American Society of Gene Therapy, vol. 14(2), pp. 268-275, (May 2006).

Akinsheye et al., "Fetal Hemoglobin in Sickle Cell Anemia," Blood, vol. 118(1), pp. 19-27, (2011).

Lin et al., "Up-Regulation of Bcl-2 is Required for the Progression of Prostate Cancer Cells from an Androgen-Dependent to an Androgen-Independent Growth Stage," Cell Research, vol. 17, pp. 531-536, (2007).

Richard Lu et al., "Siman Virus 40-Based Replication of Catalytically Inactive Human Immunodeficiency Virus Type 1 Integrase Mutants in Nonpermissive T Cells and Monocyte-Derived Macrophages", Journal of Virology, vol. 78, Jan. 2004, p. 658-668. DOI: 10.1128/JVI.78.2658-668.2004.

FM Sverdrup et al., "Development of human papillomavirus plasmids capable of episomal replication in human cell lines", Gene Therapy, Mar. 26, 1999, p. 1317-1321, Retrieved from the Internet: URL: http://www.stockton-pressco.uk/gt.

Kathleen Van Craenenbroeck et al., "Episomal vectors for gene expression in mammalian cells", Eur J. Biochem, vol. 267, p. 5665-5678, Jul. 14, 2000.

Bergvall et al. "The E1 proteins", Virology 445; p. 35-56, (Year:2013).

McBride, A., "The Papillomavirus E2 proteins", Virology 445: p. 57-79, (Year: 2013).

Chiang C-m et al., "Viral E1 and E2 proteins support replication of homologous and heterologous papillomaviral origins." PNAS 89: p. 5799-5803, (Year: 1992).

Krajinovic et al., "Sequencing data on the long control region of human papillomavirus type 16." Journal of General Virology 72:2573-2576, (Year: 1991).

Seedorg et al., "Human Papillomavirus type 16 DNA sequence." Virology 145: p. 181-185, (Year: 1985).

"Daryl S. Schiller, ""Parameters Influencing Measurement of the Gag Antigen-Specific T-Proliferative Response to HIV Type 1 Infection,""AIDS Research and Human Retroviruses, vol. 16, No. 3, pp. 259-271, (2000)."

Hong Wang., "Indirect Stimulation of Human V2V2 Cells Through Alterations in Isoprenoid Metabolism," The Journal of Immunology, (2011).

Hee Yeon Kim., "Famesyl diphosphate synthase is important for the maintenance of glioblastoma stemness," Experimental & Molecular Medicine, (2018).

Wang et al., "Butyrophilin 3A1 Plays an Essential Role in Prenyl Pyrophosphate Stimulation of Human Vg2Vd2 T Cells," Journal of Immunology, vol. 191(3), pp. 1029-1042, (Jul. 5, 2013).

Condiotti et al., "Prolonged Liver-Specific Transgene Expression by a Non-Primate Lentiviral Vector," Biochemical and Biophysical Research Communications, vol. 320(3), pp. 998-1006, (Jul. 30, 2004).

Nowacki et al., "The PAH Mutation Analysis Consortium Database: Update 1996," Nucleic Acid Research, vol. 25(1), pp. 139-142, (Jan. 1, 1997).

Ding et al., "Administration-Route and Gender-Independent Longterm Therapeutic Correction of Phenylketonuria (PKU) in a Mouse Model by Recombinant Adeno-Associated Virus 8 Pseudotyped Vector-Mediated Gene Transfer," Gene Therapy, vol. 13, pp. 583-587, (Dec. 1, 2005).

Oh et al. "Lentiviral Vector Design Using Alternative RNA Export Elements," Retrovirology, vol. 4:38, pp. 1-10, (2007).

Tokuyama, H. et al., "Vy9Vδ2 T Cell Cytotoxicity Against Tumor Cells is Enhanced by Monoclonal Antibody Drugs—Rituximab and Trastuzumab," Int J Cancer, vol. 122(11), pp. 2526-2534, (2008).

Schiller, C. B. et al., "CD19-Specific Triplebody SPM-1 Engages NK and yδ T Cells for Rapid and Efficient Lysis of Malignant B-Lymphoid Cells," Oncotarget, vol. 7(50), pp. 83392-83408, (2016).

Poonia, B. and C. D. Panza, "Gamma delta T cells from HIV+ donors can be expanded in vitro by zoledronate/interleukin-2 to become cytotoxic effectors for antibody-dependent cellular cytotoxicity," Cytotherapy 14(2): 173-181, (2012).

Gertner-Dardenne, J. et al., "Bromohydrin pyrophosphate enhances antibody-dependent cell-mediated cytotoxicity induced by therapeutic antibodies," Blood 113(20): 4875-4884, (2009).

Fisher, J. P. et al., ""Effective Combination Treatment of GD2-Expressing Neuroblastoma and Ewing's Sarcoma Using Anti-GD2 ch14.18/CHO Antibody with Vy9Vδ2+ yδT Cells, OncoImmunology, vol. 5(1), pp. e1025194, (2016).

(56) References Cited

OTHER PUBLICATIONS

Couzi, L. et al., ""Antibody-Dependent Anti-Cytomegalovirus Activity of Human γδ T Cells Expressing CD16 (FcγRIIIa),"" Blood, vol. 119(6), pp. 1418-1427, (2012).
Chen, Z. and M. S. Freedman, "CD16+ γδ T Cells Mediate Antibody Dependent Cellular Cytotoxicity: Potential Mechanism in the Pathogenesis of Multiple Sclerosis," Clin Immunology, vol. 128(2), pp. 219-227, (2008).
Capietto, A. H. et al., "Stimulated γδ T Cells Increase the in Vivo Efficacy of Trastuzumab in HER-2+ Breast Cancer," J Immunology, vol. 187(2), pp. 1031-1038, (2011).
Moser et al., "γd T cells: novel initiators of adaptive immunity," Immunological Reviews, vol. 215, pp. 89-102 (Feb. 2, 2007).
GenBank Accession No. JG619773, MNESC1NG-T3-001_L15_6FEB2009_054_MNESC1NG cell culture from Mahonia nervosa Berberis nervosa cDNA, mRNA sequence, Feb. 13, 2014 (online). [Retrieved on Dec. 5, 2017]. Retrieved from the internet:<URL: https://www.ncbi.nlm.nih.gov/nucest/JG619773 > entire document.
Lu et al., "Anti-Sense-Mediated Inhibition of Human Immunodeficiency Virus (HIV) Replication by Use of an HIV Type 1-Based Vector Results in Severely Attenuated Mutants Incapable of Developing Resistance," Journal of Virology, vol. 79, No. 13, pp. 7079-7088 (Jul. 2004).
Stunkel et al., "The Chromatin Structure of the Long Control Region of Human Papillomavirus Type 16 Repress Viral Oncoprotein Expression," Journal of Virology, vol. 73, No. 3, pp. 1918-1930 (Mar. 1999).
{Long control region} [humanpapillomavirus, type 16, Genomic, 860 nt]; Accession S60559. Publication [online]. May 7, 1993, https://www.ncbi.nlm.nih.gov/nucleotide/237343?report-genbank&log$-nucltop&blast_rank=1&RID=H3FCKA00014; pp. 1.
Human papillomavirus type 16 (HPV16), complete genome; GenBank: K02718.1; Publication [online], Mar. 18, 1994, https://www.ncbi.nlm.nih.gov/nucleotide/333031?report=genbank&log$=nucltop&blast_rank-22&RID=H3E1THFU014; pp. 1-4.
Gober et al., "Human T Cell Receptor γδ Cells Recognize Endogenous Mevalonate Metabolites in Tumor Cells," J. of Experimental Med., Jan. 20, 2003, vol. 197, pp. 163-168.
Thompson et al., "Alkylamines cause Vγ9Vδ2 T-cell activation and proliferation by inhibiting the mevalonate pathway," Blood, Jan. 15, 2006, vol. 107, pp. 651-654.
USPTO; Non-Final Office Action dated Feb. 22, 2018 in U.S. Appl. No. 13/333,882.
USPTO; Advisory Action dated Nov. 16, 2018 in U.S. Appl. No. 13/333,882.
USPTO; Restriction Requirement dated Oct. 22, 2019 in the U.S. Appl. No. 15/580,661.
USPTO; Notice of Allowance dated Oct. 29, 2019 in the U.S. Appl. No. 13/333,882.
USPTO; Notice of Allowance dated Nov. 27, 2019 in the U.S. Appl. No. 13/333,882.
USPTO; Non-Final Office Action dated Jan. 13, 2020 in the U.S. Appl. No. 15/580,661.
USPTO; Final Office Action dated Jun. 2, 2020 in the U.S. Appl. No. 15/580,661.
USPTO; Restriction Requirement dated Jun. 15, 2020 in the U.S. Appl. No. 16/308,373.
USPTO; Non-Final Office Action dated Sep. 22, 2020 in the U.S. Appl. No. 16/308,373.
USPTO; Notice of Allowance dated Jan. 13, 2021 in the U.S. Appl. No. 16/687,525.
USPTO; Non-Final Office Action dated Feb. 19, 2021 in the U.S. Appl. No. 15/580,661.
USPTO; Corrected Notice of Allowance dated Mar. 3, 2021 in the U.S. Appl. No. 16/687,525.
USPTO; Corrected Notice of Allowance dated Apr. 13, 2021 in the U.S. Appl. No. 16/687,525.
USPTO; Final Office Action dated Apr. 15, 2021 in the U.S. Appl. No. 16/308,373.
USPTO; Issue Notification dated May 18, 2021 in the U.S. Appl. No. 16/687,525.
PCT: International Search Report dated Nov. 7, 2016 in Application No. PCT/US2016/036519.
PCT: Written Opinion dated Nov. 7, 2016 in Application No. PCT/US2016/036519.
PCT: International Search Report dated Jun. 9, 2017 in Application No. PCT/US2016/066185.
PCT: Written Opinion dated Jun. 9, 2017 in Application No. PCT/US2016/066185.
PCT: International Search Report dated Dec. 15, 2017 in Application No. PCT/US2017/36433.
PCT: Written Opinion dated Dec. 15, 2017 in Application No. PCT/US2017/36433.
JP: Japanese Office Action in the JP Application No. 2018-563892 dated Oct. 14, 2020.
EPO: Extended Search Report dated Dec. 12, 2018 in EP Application No. 16808223.8.
JP: Japanese Office Action in the Application No. 2017-564550 dated Mar. 18, 2020.
EPO; Office Action in the EPO Application No. 16808223.8 dated May 11, 2020.
EPO: Supplementary European Search Report dated Dec. 19, 2019 in the Application No. 16904834.5.
EPO: Supplementary European Search Report dated Dec. 19, 2019 in the Application No. 17810976.5.
JP: Japanese Office Action dated Mar. 29, 2021 in the JP Application No. 2017-564550.
IL Office Action in Israeli Application No. 261627, dated Jan. 9, 2022, 5 pages.
JP Office Action in Application No. 2018-563892, dated May 27, 2022, 4 pages.
JP Office Action in Application No. 2018-563822, dated Jun. 2, 2022, 10 pages.
CN Office Action in Application No. 201780047904.1, dated Jun. 14, 2022, 8 pages.
KR Office Action in Application No. 10-2019-700296, dated Jul. 19, 2022, 5 pages.
JP Notice of Allowance in Japanese Application No. 2018-563892, dated Sep. 28, 2022, 6 pages (with English translation).
JP Office Action in Japanese Application No. 2021-021627, dated Aug. 1, 2022, 12 pages (with English translation).
U.S. Notice of Allowance in U.S. Appl. No. 16/563,738, dated Aug. 31, 2022, 5 pages.
EP Office Action in European Application No. 17810976, dated Nov. 18, 2022, 6 pages.
IN Office Action in Indian Application No. 201947000153, dated Oct. 28, 2022, 8 pages.

* cited by examiner

FIG. 2

| Heterologous Proteins for Use in the Present Invention | |
|---|---|
| Heterologous Protein | Reference |
| Human: | |
| ZAP-70 protein-tyrosine kinase | Isakov et al. 1996 |
| ABC transporter tap1 processing (TAP) | Meyer et al. 1994 |
| ABC transporter tap2 processing (TAP) | Meyer et al. 1994 |
| $\alpha_2 C_2$ adrenoceptor | Marjamaki et al. 1994 |
| α-galactosidase A | Coppola et al. 1994 |
| α and β globins | Groebe et al. 1992 |
| $\alpha_1$ glycine receptor | Cascio et al. 1993 |
| α-macroglobulins (aM) | Rompaey & Marynen 1992 |
| α and β platelet-derived growth factor receptors | Jensen et al. 1992 |
| Adenosine deaminase | Medin et al. 1990 |
| aldase reductase | Nishimura et al. 1991 |

FIG. 2 (Continued)

| Heterologous Proteins for Use in the Present Invention | |
|---|---|
| Heterologous Protein | Reference |
| α-interferon | Maeda et al. 1985 |
| 5-α reductase (type 1) | Delos et al. 1994 |
| Ah receptor and Ah receptor nuclear translocater | Chan et al. 1994 |
| Alzheimer amyloid precursor protein | Ramakrishna et al. 1991 |
| Alzheimer β-amyloid peptide precursor | Currie et al. 1991 |
| Amyloid peptide precursor | Essalmani et al. 1996 |
| Amyloid precursor protein | Bhasin et al. 1991 |
| Amyloid b protein precursor | Bhasin et al. 1991 |
| Amyloid precursor protein | Lowery et al. 1991 |
| Androgen receptor | Beitel et al. 1995 |
| Angiotensin | Williams et al. 1994 |
| Androgen receptor | Chang et al. 1992 |
| Antithrombin III | Gillespie et al. 1991 |
| Apolipoprotein E | Gretch et al. 1991 |
| Aromatase P450 | Amarneh & Simpson 1995 |
| Autoantigen of Wegener's granulomatrosis (PR3) | Szymkowiak et al. 1996 |
| b1,2-N-acetylglucosaminyl-transferase I (hGNT-I) | Wagner et al. 1996 |
| β1 γ2 dimers of G-protein | Dietrich et al. 1992 |
| β1,β2,γ2 subunits of heterotrimeric guanine nucleotide-binding protein | Graber et al. 1992 |
| β1 –adrenergic receptor | Ravet et al. 1992 |
| β2 –adrenergic receptor | Kleymann et al. 1993 |
| β-adrenergic receptor kinase | Sohlemann et al. 1993 |
| β galactosidase | Itoh et al. 1990 |
| β interferon | Smith et al. 1983 |
| β2 –glycoprotein I | Igarashi et al. 1996 |
| BCl2 | Alnemri et al. 1992 |
| BCl-2 oncoprotein | Reid et al. 1992 |

FIG. 2 (Continued)

| Heterologous Proteins for Use in the Present Invention | |
|---|---|
| Heterologous Protein | Reference |
| bone morphogenetic protein-2 | Maruoka et al. 1995 |
| Cc gene | Poul et al. 1995 |
| Cg1 sequence | Poul et al. 1995 |
| C-reactive protein | Marnell et al. 1995 |
| cAMP-specific phosphodiesterase | Amegadzie et al. 1995 |
| CD95/APO-1/Fas ligand | Mariani et al. 1996 |
| CD4 | Murphy et al. 1990; Lazarte et al. 1992 |
| Cdc42 GTP-binding protein | Cerione et al. 1995 |
| c-fos protein | Tratner et al. 1990 |
| CYP2A6 | Nanji et al. 1994 |
| calpain I | Meyer et al. 1996 |
| Carcinoembryonic antigen | Bei et al. 1994 |
| Carcinoembryonic antigen CD 66b | Yamamaka et al. 1996 |
| Carcinoembryonic antigen CD66c | Yamamaka et al. 1996 |
| Cholecystokinin B (CCK$_9$) | Gimpl et al. 1996 |
| Choriogonadotropin α subunit | Nakhai et al. 1991 |
| Choriogonadotropin β-subunit | Chen et al. 1991 |
| Choriogonadotropin β-subunit descarboxyl-terminal peptide | Chen and Bahl 1991 |
| Chorionic gonadotropin hormone precursor | Nakhai et al. 1991 |
| Chorionic gonadotropin hormone (β-subunit) | Hasnain et al. 1994 |
| Chorionic gonadotropin hormone β subunit | Nakhai et al. 1992 |
| Complement C1r | Sass et al. 1977 |
| Complement C1r proenzyme | Gal et al. 1989 |
| Complement protein C9 | Tomlinson et al. 1993 |
| Corticosteroid binding globulin | Ghose Dastidar et al. 1991 |
| c-myc protein | Miyamoto et al. 1985 |

FIG. 2 (Continued)

| Heterologous Proteins for Use in the Present Invention | |
|---|---|
| Heterologous Protein | Reference |
| Complement protein C9 | Tomlinson et al. 1993 |
| Corticosteroid binding globulin (hCBG) | Ghose-Dastidar et al. 1991 |
| Creatine kinase B (B-CK) | de Kok et al. 1995 |
| Cyclooxygenase-2 | Cromlish et al. 1994 |
| Cytochrome b5 | Patten & Koch 1995 |
| Cytochrome B558 | Katkin et al. 1992 |
| Cytochrome CYP3A4 | Lee et al. 1995 |
| Cytochrome P450 CYP3A4 | Buters et al. 1994 |
| Cytochrome P-450 isoform(s) | Clair et al. 1994 |
| Cytomegalovirus 65K tegument phosphoprotein | La Fauci et al. 1994 |
| Cytomegalovirus IE1, IE1 exon 4 | Davrinche et al. 1993 |
| Cytosolic phospholipase A2 | Abdullah et al. 1995 |
| D4 dopamine receptor | Mills et al. 1993 |
| DNA ligase I | Gallina et al. 1995 |
| DNA polymerase α subunit | Copeland and Wang 1991 |
| DNA polymerase d catalytic subunit | Zhou et al. 1996 |
| DNA topoisomerase I | Zhelkovsky & Moore 1994 |
| Dopamine D2 receptor | Javitch et al. 1994 |
| EGF receptor | Greenfield et al. 1988 |
| EGF receptor-tyrosine kinase domain | Wedegaertner et al. 1989 |
| Endothelial nitric oxide synthase | Chen et al. 1996 |
| Epidermal growth factor receptor | Waterfield & Greenfield 1991 |
| Epidermal-growth-factor receptor protein-tyrosine kinase | McGlynn et al. 1992 |
| Epidermal growth factors IX and XIIa | Astermark et al. 1994 |
| Erythrocyte anion exchanger | Dale et al. 1996 |
| Erythropoietin | Quelle et al. 1992 |
| Estrogen receptor | Beekman et al. 1994 |

FIG. 2 (Continued)

| Heterologous Proteins for Use in the Present Invention | |
|---|---|
| Heterologous Protein | Reference |
| factor VIII - B domain deleted | Webb et al. 1993 |
| Fibroblast growth factor receptor subtype ligand binding domain | Sisk et al. 1992 |
| follicle-stimulating hormone receptor | Christophe et al. 1993 |
| furin | Bravo et al. 1994 |
| $GABA_A$ receptor α1 subunits | Birnir et al. 1995 |
| $GABA_A$ receptor β1 subunits | Birnir et al. 1995 |
| ga773 - 2 antigen | Strassburg et al. 1992 |
| GMP synthetase | Lou et al. 1995 |
| Glucocerebrosidase | Martin et al. 1988 |
| Glucocorticoid receptor | Srinivasan et al. 1990 |
| Glutamic acid decarboxylase | Mauch et al. 1993 |
| glycine receptor α1 | Morr et al. 1995 |
| group b rotavirus ADRV, VP4 | Mackow et al. 1993 |
| group II Phospholipase A2 | Tremblay et al. 1993 |
| growth hormone | Sumathy et al. 1996 |
| growth hormone receptor - extracellular domain | Ota et al. 1991 |
| $5-HT_{1A}$ receptor | Mulheron et al. 1994 |
| hst-1 transforming protein | Miyagawa et al. 1988 |
| heart (R)-3-hydroxybutyrate dehydrogenase | Green et al. 1996 |
| Hematopoietic glycopeptide erythropoietin | Quelle et al. 1992 |
| Hemopexin | Satoh et al. 1994 |
| Heparin cofactor II | Ciaccia et al. 1995 |
| Hepatitis b virus X protein | Klein et al. 1992 |
| Hepatocyte growth factor | Yee et al. 1993 |
| Hepatocyte growth factor | Lee et al. 1993 |
| high-affinity IgE receptor-a chain | Yagi et al. 1994 |
| 17b-hydroxysteroid dehydrogenase | Breton et al. 1994 |

FIG. 2 (Continued)

| Heterologous Proteins for Use in the Present Invention | |
|---|---|
| Heterologous Protein | Reference |
| 5-hydroxytryptamine$_{1A}$ | Butkerait et al. 1995 |
| 5-hydroxytryptamine receptors (5-HT$_{1A}$, 5-HT$_{1D\alpha}$, 5-HT$_{1D\beta}$, 5-HT$_{1E}$) | Parker et al. 1994 |
| IgA | Carayannopoulos et al. 1994 |
| IL2 receptor α & β chains | Lindqvist et al. 1993 |
| Immunodeficiency virus-type 1 gag precursor | Chazal et al. 1994 |
| Immunodeficiency virus-1 gp41 | Lu et al. 1993 |
| Immunodeficiency virus-1 gp120 | Yeh et al. 1993 |
| insulin holoreceptor | Paul et al. 1990 |
| insulin receptor substrate-1 | Siemeister et al. 1995 |
| insulin receptor β-subunit | Herrera et al. 1988 |
| insulin receptor β subunit transmembrane/cytoplasmic domain | Li et al. 1992 |
| insulin receptor ectodomain | Sissom et al. 1989; 1991 |
| insulin receptor protein-tyrosine kinase domain | Ellis et al. 1988 |
| insulin receptor cytoplasmic domain of β subunit | Herrera et al. 1988 |
| insulin receptor protein tyrosine-kinase-cytoplasmic domain | Ellis and Levine 1991 |
| insulin-like growth factor II | Congote and Li, 1994 |
| insulin-like growth factor II | Marumoto et al. 1992 |
| Intercellular adhesion molecule 1 (ICAM-1) | Cobb et al. 1992 |
| Interferon-g glycoforms | Ogonah et al. 1995 |
| Interleukin 2 | Smith et al. 1985 |
| Interleukin 2 glycoprotein variants | Grabenhorst et al. 1993 |
| Interleukin-2 receptor gamma chain | Raivio et al. 1995 |
| Interleukin 5 | Brown et al. 1995 |
| Interleukin 6 | Matsuura et al. 1991 |
| Interleukin-6 receptor | Weiergraber et al. 1995 |

FIG. 2 (Continued)

| Heterologous Proteins for Use in the Present Invention | |
|---|---|
| Heterologous Protein | Reference |
| Intrinsic factor | Gordon et al. 1992 |
| iron regulatory factor | Emery-Goodman et al. 1993 |
| Isoforms (neuronal, inducible, endothelial) nitric oxide synthase | Nakane et al. 1995 |
| Ku autoantigen | Allaway et al. 1990 |
| Lecithin-cholesterol acyltransferase | Chawla & Owen 1995 |
| Leukotriene A4 hydrolase | Gierse et al. 1993 |
| link protein | Grover & Roughley 1994 |
| liver carboxylesterase | Kroetz et al. 1993 |
| Lymphocytic activation gene (LAG-1) | Baixeras et al. 1990 |
| lysyl hydroxylase | Krol et al. 1996; Pirskanen et al. 1996 |
| Lysosomal β-galactosidase | Itoh et al. 1991 |
| 5'lipoxygenase | Dunk et al. 1989 |
| m1 muscarinic acetylcholine receptors | Haga et al. 1996 |
| μ2 muscarinic cholinergic receptor | Debburman et al. 1995 |
| μ3 (hμ3) muscarinic cholinergic receptors | Debburman et al. 1995 |
| MHC class I HLA-b27 antigen | Levy and Kvist 1990 |
| MHC class II DR4a, DR4b, extracellular domain | Scheerle et al. 1992 |
| Macrophage colony stimulating factor | Qiu et al. 1995 |
| Matrilysin | Lopez de Turiso et al. 1996 |
| Metallothionein-II | Schmiel et al. 1985 |
| Mineralocorticosteriod receptor | Binart et al, 1991 |
| Monocyte chemoattractant protein-1 | Ueda et al. 1994; Ishii et al. 1995 |
| Multidrug resistance 1 | Germann et al. 1990 |
| Multidrug resistance P-glycoprotein | Rao et al. 1994 |
| Muscarine receptor μ2 | Kameyama et al. 1994 |

FIG. 2 (Continued)

| Heterologous Proteins for Use in the Present Invention | |
|---|---|
| Heterologous Protein | Reference |
| Myeloperoxidase | Taylor et al. 1992 |
| Myogenic factors myf4, myf5 | Braun et al. 1991 |
| N-formyl peptide receptor | Quehenberger et al. 1992 |
| $Na^+/H^+$ antiporter | Fafournoux et al. 1991 |
| NADPH-P450 oxidoreductase | Tamura et al. 1992 |
| nerve growth factor | Buxser et al. 1991 |
| nerve growth factor receptor | Vissavajjhala et al. 1990 |
| Neutrophil NADPH oxidase factors p47-[phox], p67[phox] | Leto et al. 1991 |
| Nuclear hormone receptor H-2RIIBP | Marks et al. 1992 |
| Nucleolar protein p120 | Ren et al. 1996 |
| Oxytocin receptor | Gimpl et al. 1995 |
| p53 | Patterson et al. 1996 |
| P450 2E1 | Patten & Koch 1995 |
| Pancreatic lipase | Thirstrup et al. 1993 |
| Pancreatic procolipase | Lowe 1994 |
| Papillomavirus type 11 E1, E2 | Bream et al. 1993 |
| Papillomavirus type 11 L1 protein | Rose et al. 1993 |
| Papillomavirus type 16 E2 | Sanders et al. 1995 |
| Papillomovirus type 16 L1 protein | Kirnbauer et al. 1993 |
| Papillomavirus type 45 L1 protein | Touze et al. 1996 |
| Parainfluenza virus type 3, 7, HN, 7HN | Lehman et al. 1993 |
| Parathyroid hormone | Mathavan et al. 1995 |
| Parvovirus B19 vp1, vp2 | Cubie et al. 1993 |
| Phospholipase $A_2$ | Abdullah et al. 1995 |
| Placental aromatase (CYP19A1) | Sigle et al. 1994 |
| plasma plasminogen | Whitefleet-Smith et al. 1989 |
| Plasminogen | Davidson et al. 1991 |

FIG. 2 (Continued)

| Heterologous Protein | Reference |
|---|---|
| Plasminogen (HPg) | Castellino et al. 1993 |
| Plasminogen activator inhibitor-2 | Pei et al. 1995 |
| Platelet glycoprotein IBb | Finch et al. 1996 |
| platelet 12-lipoxygenase | Chen et al. 1993 |
| poly(ADP-ribose) polymerase | Giner et al. 1992 |
| pre-pro endothelin-1 | Benatti et al. 1992 |
| pre-pro gastrin releasing peptide | Lebacq-verheyden et al. 1988 |
| pro-a1(III) chains | Tomita et al. 1995 |
| ProapoA-I | Sorci-Thomas et al. 1996 |
| Progesterone receptor (A form) | Elliston et al. 1992 |
| Progesterone receptors A&B forms | Christensen et al. 1991 |
| prolyl 4-hydroxylase a, b subunits | Vuori et al. 1992 |
| prolyl 4-hydroxylase a subunit with BiP polypeptide | Veijola et al. 1996 |
| prosaposin | Leonova et al. 1996 |
| prostaglandin G/H synthase | George et al. 1996 |
| prostaglandin G/H synthase 1 | Barnett et al. 1994 |
| prostaglandin G/H synthase 2 | Barnett et al. 1994 |
| protein disulphide isomerase | Vuori et al. 1992 |
| protein kinase c-d | Rankl et al. 1994 |
| protein kinase Cm | Dieterich et al. 1996 |
| pro-urokinase | Gao and Hu 1994 |
| rab 6 | Yang et al. 1992 |
| rap1A | Quilliam et al. 1990 |
| recombinant IL-8 | Kang et al. 1992 |
| recombinant p56$^{lck}$ | Flotow et al. 1996 |
| renin | Mathews et al. 1996 |
| respiratory syncytial virus F and G glycoproteins | Wathen et al. 1989 |

FIG. 2 (Continued)

| Heterologous Proteins for Use in the Present Invention | |
|---|---|
| Heterologous Protein | Reference |
| retinoblastoma pp110$^{RB}$ | Wang et al. 1990 |
| retinoic acid receptor a1 | Quick et al. 1994 |
| retinoic acid receptor - g1 | Reddy et al. 1992 |
| ssDNA-binding protein | Stigger et al. 1994 |
| sex steroid-binding protein (hSBP/hABP, hSHBG) | Sui et al. 1995 |
| soluble human insulin receptor - ectodomain | Sissom and Ellis 1992 |
| soluble human insulin receptor tyrosine kinase | Ahn et al. 1993 |
| Sos1 protein | Frech et al. 1995 |
| steroid 5α-reductase | Iehle et al. 1993 |
| synthetic basic fibroblast growth factor | Hills & Crane-Robinson 1995 |
| TII (CD2) t-lymphocyte surface glycoprotein | Richardson et al. 1988 |
| TII (CD2) | Alcover et al. 1988 |
| T-cell leukemia virus type 1 p40 | Nyunoya et al. 1988 |
| T-cell protein tyrosine kinase | Lehr et al. 1996 |
| T-cell protein-tyrosine-phosphatase | Zander et al. 1991 |
| T-lymphotropic virus type 1 envelope protein | Yamashita et al. 1992 |
| terminal transferase | Chang et al. 1988 |
| terminal deoxynucleotidyl transferase | di Primio et al. 1992 |
| thrombomodulin | Marumoto et al. 1993 |
| thromboxane synthase | Yokoyama et al. 1993 |
| thyroid hormone B1 receptor | Putlitz et al. 1991 |
| thyroid peroxidase | Kendler et al. 1993 |
| thyrotropin receptor extracellular domain | Seetharamaiah et al. 1993 |
| thyrotropin hormone receptor- extracellular domain | Huang et al. 1993 |
| tissue inhibitor of metalloproteinases-1 | Gomez et al. 1994 |
| tissue plasminogen activator | Jarvis et al. 1993 |
| tissue-type plasminogen activator | Steiner et al. 1988 |

FIG. 3

| Transport genes | References |
|---|---|
| VP22 in lentivirus | Lai and Brady, 2002 |
| Pancreatic presecretory proteins | Thomas, 1982 |
| Resistance -cell (cancer) division proteins (Transporter AcrB) | Krishan et al., 2000<br>Gary et al., 2006 |
| HIV-1-Tat | Schwarze et al., 1999 |
| Antennapedia homeobox domain | Derossi et al., 1996 |
| Mitochondrial carrier proteins | Walker et al., 1992 |
| Amino acid: cation symporters (Proton glutamate symporter) | Koch et al., 2007 |
| Drug/Metabolite transporter (Multidrug resistance transporter EmrE) | Livshits, et al., 2003 |
| Light absorption-driven transporter (Bacteriorhodopsin-like proteins) | Waschuk et al., 2005 |
| Transmembrane cytochrome b-like proteins (Coenzyme Q-cytochrome reductase) | Dudkina et al., 2005 |
| Electrochemical potential-driven transporters (ATPases) | Ishmukhametov et al., 2007 |
| Mitochondrial membrane transport protein | Nicholls et al., 2005 |
| Glucose transporters | Hediger et al., 1994 |
| P-glycoprotein | Michael et al., 2002 |
| Glutamate transporter | Shigeri et al., 2004 |
| Norepinephrine transporter | Shannon et al., 2000 |

FIG. 3 (Continued)

| Transport genes | References |
|---|---|
| Vesicular monoamine transporter | Rang et al., 2003 |
| The H+/peptide co-transporters (PEPT1/2) | Kenichi et al., 2000 |
| Renal peptide transporters | Daniel et al., 1997 |
| Apolipoprotein E | Gretch et al., 1991 |

FIG. 4

| Promoter Element | Inducer | References |
|---|---|---|
| MT II<br><br>Regulation of human metallothionein – IIA gene | Phorbol Ester (TFA)<br>Heavy metals | Palmiter et al., 1982; Haslinger and Karin, 1985; Searle et al., 1985; Stuart et al., 1985; Imagawa et al., 1987, Karin et al., 1987; Angel et al., 1987b; McNeall et al., 1989 |
| MMTV (mouse mammary tumor virus)<br><br>promoter involved in regulation by Glucocorticoids involved Pathway in Chronic Obstructive Pulmonary disease | Glucocorticoids | Huang et al., 1981; Lee et al., 1981; Majors and Varmus, 1983; Chandler et al., 1983; Lee et al., 1984; Ponta et al., 1985; Sakai et al., 1988 |
| $\beta$-Interferon<br><br>regulation of infection disease | Poly(rI)x<br>poly(rc) | Tavernier et al., 1983 |
| Adenovirus 5 E2<br><br>Gene therapy promoter in anti-cancer infection disease | E1a | Imperiale and Nevins, 1984 |
| Collagenase<br>anti-wrinkle application | Phorbol Ester (TPA) | Angel et al., 1987a |

FIG. 4 (Continued)

| Promoter Element | Inducer | References |
|---|---|---|
| Stromelysin<br>application on cardiovascular disease | Phorbol Ester (TPA) | Angel et al., 1987b |
| SV40<br>Gene Vector selection | Phorbol Ester (TPA) | Angel et al., 1987b |
| Murine MX Gene<br>for Newcastle disease in bird industry | Interferon, Newcastle Disease Virus | |
| GRP78 Gene<br>regulation of Hepatitis C virus | A23187 | Resendez et al., 1988 |
| α-2-Macroglobulin<br>Sickle cell disease | IL-6 | Kunz et al, 1989 |
| Vimentin<br>Serum inductibility of the human vimentin promoter | Serum | Rittling et al., 1989 |
| MHC Class I Gene H-2Kb<br>regulation for cancer/gene therapy | Interferon | Blanar et al., 1989 |
| HSP70<br>Cell-specific activation of Glial-cell | Ela, SV40 Large T Antigen | Taylor et al., 1989; Taylor and Kingston, 1990a, b |
| Proliferin<br>Chronic myelogenous leukemic cell | Phorbol Ester-TPA | Mordacq and Linzer, 1989 |
| Tumor Necrosis Factor<br>cancer cell gene therapy, immune disease | FMA | Hensel et al., 1989 |

FIG. 4 (Continued)

| Promoter Element | Inducer | References |
|---|---|---|
| Thyroid Stimulating Hormone a Gene<br>Thyroid cell specific promoter activator | Thyroid Hormone | Chatterjee et al., 1989 |
| CMV promoter<br>general mammalian promoter | | |
| hSyn-1<br>human neuron-specific promoter | | |
| hPSA<br>human Prostate Specific Antigen Promoter | | |
| hCCKAR<br>Human Cholecystorinin (CCK) promoter for gene drug specific expression in pancreatic cancer cells, but not in normal cells | | |
| hAFP<br>human Alpha-Fetoprotein promoter<br>Specificity: Hepatocellular carcinoma (liver cancer cells) | | |
| Neu-Oncoven/c-erbB2 promoter<br>human breast pancreatic cancer (promoter) | | |

FIG. 4 (Continued)

| Promoter Element | Inducer | References |
|---|---|---|
| CEA promoter (Carcinoembryonic Antigen) human epithelial cancer cells (lung cancer, gastric cancer cells) | | |

FIG. 5

| ENHANCER | REFERENCES |
|---|---|
| Immunoglobulin Heavy Chain | Banerji et al., 1983; Gilles et al., 1983; Grosschedl and Baltimore, 1985; Atchinson and Perry, 1986, 1987; Imler et al., 1987; Weinberger et al., 1984; Kiledjian et al., 1988; Porton et al., 1990 |
| Immunoglobulin Light Chain | Queen and Baltimore, 1983; Picard and Schaffner, 1984 |
| T-Cell Receptor | Luria et al., 1987; Winoto and Baltimore, 1989; Redondo et al., 1990 |
| HLA DQα and DQβ<br>β-Interferon | Sullivan and Peterlin, 1987;<br>Goodbourn et al., 1986; Fujita et al., 1987; Goodbourn and Maniatis, 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRα | Sherman et al., 1989 |
| β-Actin | Kawamoto et al., 1988; Ng et al.; 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Ornitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987; Tronche et al., 1989, 1990 |
| α-Fetoprotein | Godbout et al., 1988; Campere and Tilghman, 1989 |

FIG. 5 (Continued)

| ENHANCER | REFERENCES |
|---|---|
| t-Globin | Bodine and Ley, 1987; Perez-Stable and Constantini, 1990 |
| β-Globin | Trudel and Constantini, 1987 |
| e-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987; Schaffner et al., 1988 |
| Polyoma | Swartzendruber and Lehman, 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and Villarreal, 1988 |

FIG. 5 (Continued)

| ENHANCER | REFERENCES |
|---|---|
| Retroviruses | Kriegler and Botchan, 1982, 1983; Levinson et al., 1982; Kriegler et al., 1983, 1984a, b, 1988; Bosze et al., 1986; Miksicek et al., 1986; Celander and Haseltine, 1987; Thiesen et al., 1988; Celander et al., 1988; Choi et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al, 1987; Stephens and Hentschel, 1987; Glue et al., 1988 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |
| Human Immuno- deficiency Virus | Muesing et al., 1987; Hauber and Cullan, 1988; Jakobovits et al., 1988; Feng and Holland, 1988; Takebe et al., 1988; Rosen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

FIG. 7

| ELEMENT / INDICATION | First Regulatory Nucleic Acid Sequence | First Heterologous Nucleic Acid Sequence | Second Regulatory Nucleic Acid Sequence | Second Heterologous Nucleic Acid Sequence | Reference |
|---|---|---|---|---|---|
| PROSTATE CANCER | CMV | P53 | hPSA<br><br>None<br>HIV-Tat<br>VP22 | Bcl-2 RNAi | |
| PANCREATIC CANCER | CMV | P53 | hCCKAR<br><br>None<br>HIV-Tat<br>VP22 | K-ras RNAi | |
| LIVER CANCER | CMV | P53 | hAFP<br><br>None<br>HIV-Tat<br>VP22 | Bcl-2 RNAi | |
| GAUCHER'S DISEASE | CMV<br><br>None<br>VP22 | Glucocerebrosidase | IRES/Cleavage site<br><br>None | Human intrinsic selectable marker, e.g.:<br><br>IL-2Ra (huCD25)<br>huNGF | |
| FABRY'S DISEASE | CMV<br><br>None<br>VP22 | Alpha Galactosidase A | IRES/Cleavage site<br><br>None | IL-2Ra (huCD25) | |
| ALZHEIMER'S DISEASE | CMV<br><br>None<br>VP22 | hNGF | Cleavage site/hNSE | AAP (beta-amyloid precursor protein) RNAi | |
| PARKINSON'S DISEASE | CMV<br><br>None<br>VP22 | hNGF | Cleavage site/hNSE | AAP (beta-amyloid precursor protein) RNAi<br><br>+ third gene<br><br>CS-hBDNF (brain-derived neurotropic factor) | |
| PARKINSON'S DISEASE | CMV<br><br>None | hBDNF (brain-derived neurotropic factor) | Cleavage site/hNSE | hGAD (human glutamic acid decarboxylase) | |
| PARKINSON'S DISEASE | CMV<br><br>VP22 | hBDNF (brain-derived neurotropic factor) | Cleavage site/hNSE | hGAD (human glutamic acid decarboxylase)<br><br>+ third gene<br><br>CS-hNGF | |
| LEBER CONGENITAL AMAUROSIS (blindness and optic nerve disease) | CMV | RPE65 (retinal pigment epithelium) | Cleavage site/hNSE | hBDNF (brain-derived neurotropic factor) | |

FIG. 7 (Continued)

| ELEMENT / INDICATION | First Regulatory Nucleic Acid Sequence | First Heterologous Nucleic Acid Sequence | Second Regulatory Nucleic Acid Sequence | Second Heterologous Nucleic Acid Sequence | Reference |
|---|---|---|---|---|---|
| LEBER CONGENITAL AMAUROSIS (blindness and optic nerve disease) | CMV VP22 | RPE65 (retinal pigment epithelium) | Cleavage site/hNSE | hBDNF (brain-derived neurotropic factor) + third gene CS-hNGF | |
| COSMETIC Anti-Wrinkle Gene Reagent Formulate 1 | CMV | MMP (which one?) RNAi | Cleavage site | TL (tropoelastin) RNAi | |
| COSMETIC Anti-Wrinkle Gene Reagent Formulate 2 | CMV | Collagen type 1 alpha 1 | Cleavage site | FE (fibroblast elastases) | |
| COSMETIC Anti-Wrinkle Gene Reagent Formulate 3 | CMV | SOD (superoxide dismutase) | Cleavage site | ?? | |
| COSMETIC Hair-enhancement Reagent | CMV | SH (sonic hedgehog) | Cleavage site | DSG4 (desmoglein 4) | |

FIG. 7 (Continued)

| ELEMENT / INDICATION | Cloned Structural Gene | Clone Type | Exemplary Construct | Reference |
|---|---|---|---|---|
| Adrenal Gland Disease | Activin | Porcine-cDNA | LV - CMV - p-cDNA - (CS) - EGFP | Mason AJ, Nat, 318:659 1985 |
| Coronary Artery Disease | Adenosine Deaminase | h-cDNA | LV - CMV - h-cDNA - (CS) - RNAi (fatty acid) | Wiginton DA, PNAS, 80:7481, 1983 |
| Cardiovascular Disease | Angiotensinogen I | r-cDNA r-gDNA | LV - CMV - (r)cDNA - (CS) - r-gDNA | Ohkubo H, PNAS, 80:2196, 1983; Tanaka T, JBC, 259:8063, 1984 |
| Congenital Antithrombin IV Deficiency Liver Disease | Antithrombin III | h-cDNA h-cDNA and gDNA | LV - CMV - h-cDNA - (CS) - AFP-gDNA | Bock SC, NAR 10:8113, 1982; Prochownik EV, JBC, 258:8389, 1983 |
| Alpha-1 Antitrypsin Deficiency Lung Disease | Antitrypsin, alpha 1 | h-cDNA h-gDNA RFLP | LV - CMV - h-cDNA - (CS) - h-gDNA (RFLP) | Kurachi K, PNAS, 78:6826, 1981; Leicht M, Nat, 297:655, 1982; Cox DW, AJHG, 36:134S, 1984 |
| Tangier Disease with Coronary Artery Disease | Apolipoprotein A-I | h-cDNA, h-gDNA RFLP h-gDNA | LV - CMV - h-cDNA - (CS) - h-gDNA - (CS) - RFLP | Shoulders CC, NAR, 10:4873, 1982; Karathanasis SK, Nat, 301:718, 1983; Karathanasis SK, PNAS, 80:6147, 1983 |
| Coronary Artery Disease | Apolipoprotein A-II | h-cDNA Chr h-cDNA | LV - CMV - h-cDNA - (CS) - Chr | Sharpe CR, NAR, 12:3917, 1984; Sakaguchi, AY, AJHB, 36:207S, 1984; Knott TJ, BBRC, 120:734, 1984 |
| Risk Factor for Alzheimer's Disease | Apolipoprotein C-I | h-cDNA | LV - CMV - h-cDNA - (CS) - RNAi (B-amyloid) | Knott TJ, NAR, 12:3909, 1984 |
| Premature Vacular Disease | Apolipoprotein C-II | h-cDNA h-cDNA h-cDNA RFLP | LV - CMV - h-cDNA - (CS) RFLP | Jackson CL, PNAS, 81:2945, 1984; Mykelbost O, JBC, 249:4401, 1984; Fojo SS, PNAS, 81:6354, 1984; Humphries SE, CGen, 26:389, 1984 |
| Cardiovascular Disease with Metabolic Syndrome (IRL=triacylglycero-rich Lipoprotein) | Apolipoprotein C-III | h-cDNA and gDNA h-cDNA | LV - CMV - h-cDNA - (CS) - h-cDNA | Karathanasis SK, Nat, 304:371, 1983; Sharpe CR, NAR, 12:3917, 1984 |
| Cerebral Palsy Alzheimer's Disease | Apolipoprotein E | h-cDNA | LV - CMV - h-cDNA - (CS) - RNAi (B-amyloid) | Breslow JL, JBC, 257:14639, 1982 |

FIG. 7 (Continued)

| ELEMENT / INDICATION | Cloned Structural Gene | Clone Type | Exemplary Construct | Reference |
|---|---|---|---|---|
| Congenital Heart Disease | Atrial Natriuretic Factor | h-cDNA<br>h-cDNA<br>h-cDNA<br>h-gDNA<br>h-gDNA<br>h-gDNA | LV - CMV - h-gDNA (CS) - h-cDNA | Oikawa S, Nat, 309:724, 1984; Nakayama K, Nat. 310:699, 1984; Zivin BA, PNAS, 81:6325, 1984; Seidman CE, Sci, 225:1206, 1984; Nemer M, Nat, 312:654, 1984; Greenberg BI, Nat, 312:665, 1984 |
| Crohn's Disease Inflammatory Bowel Disease | Chorionic Gonadotropin, Alpha Chain | h-cDNA RFLP | LV - CMV - h-cDNA - (CS) - RFLP | Fiddes JC, Nat, 281:351, 1981; Boothby M, JBC, 256:5121, 1981 |
| Gestational Trophoblastic Disease | Chorionic Gonadotropin Beta Chain | h-cDNA<br>h-gDNA<br>h-gDNA | LV - CMV - h-cDNA - (CS) - h-gDNA | Fiddes JC, Nat, 286:684, 1980; Boorstein WR, Nat, 300:419, 1982; Talmadge K, Nat, 307:37, 1984 |
| Infection Disease | Chymosin, pro-(rennin) | bovine-cDNA | LV - CMV - h-cDNA - (CS) - EGFP | Harris TJR, NAR, 10:2177, 1982 |
| Coeliac Disease | Complement, Factor B | h-cDNA<br>h-cDNA and gDNA | LV - CMV - h-cDNA - (CS) - gDNA | Woods DE, PNBAS, 79:5661, 1982; Duncan R, PNAS, 80:4464, 1983 |
| Grave's Disease | Complement C2 | h-cDNA<br>h-gDNA (C2, C4, and B) | LV - CMV - h-cDNA - (CS) - h-gDNA | Bentley DR, PNAS, 81:1212, 1984; Carroll MC, Nat, 307:237, 1984 |
| Renal Disease | Complement C3 | m-cDNA<br>h-gDNA | LV - CMV - h-gDNA-(CS) - m-cDNA | Domdey H, PNAS, 79:7619, 1983; Whitehead AS, PNAS, 79:5021, 1982 |
| Lupus Disease | Complement C4 | h-cDNA and gDNA<br>h-cDNA | LV - CMV - h-cDNA (CS) - gDNA | Carroll MC, PNAS, 80:264, 1983; Whitehead AS, PNAS, 80:5387, 1983 |
| Autoimmune Disease | Complement C9 | h-cDNA | LV - CMV - h-cDNA - (CS) - EGFP | DiScipio BC, PNAS, 81:7298, 1984 |
| Alzheimer's Disease A Stress Factor | Corticotropin releasing factor | sheep-cDNA<br>h-gDNA | LV - CMV - h-gDNA - (CS) - RNAi (B-amyloid) | Furutani Y, Nat, 301:537, 1983; Shibahara S, EMBO J, 2:775, 1983 |
| Salivary Disease Prostate Disease/Cancer | Epidermal growth factor | m-cDNA<br>m-cDNA<br>h-gDNA | LV - CMV - h-gDNA - (CS) - m-cDNA | Gray A, Nat, 303:722, 1983; Scott J, Sci, 221:236, 1983; Brissenden JE, Nat, 310:781, 1984 |
| Tongue (oral) Cancer | Epidermal growth factor receptor, oncogene c-erb B | h-cDNA and Chr | LV - CMV - h-cDNA - (CS) - Chr | Lan CR, Sci, 224:843, 1984 |
| Immune Disorder | Epoxide dehydratase | r-cDNA | LV - CMV - r-cDNA - (CS) - EGFP | Gonzalez FJ, JBC, 256:4697, 1981 |

FIG. 7 (Continued)

| ELEMENT / INDICATION | Cloned Structural Gene | Clone Type | Exemplary Construct | Reference |
|---|---|---|---|---|
| Congenital Heart Disease | Erythropoietin | h-cDNA | LV - CMV - h-cDNA - (CS) - RNAi (fatty acids) | Lee-Huang S, PNAS, 81:2708, 1984 |
| Inflammation Disease | Esterase inhibitor, dehydratase | h-cDNA | LV - h-cDNA - (CS) - RNAi (IL-2) | Stanley KK, EMBO J, 3:1429, 1984 |
| N/K | Factor VIII | h-cDNA and gDNA h-cDNA | | Gitschier J, Nat, 312:326, 1984. |
| N/K | Factor IX, Christmas factor | h-cDNA h-cDNA RFLP h-gDNA | | Kurachi K, PNAS, 79:6461, 1982; Choo KH, Nat, 299:178, 1982; Camerino G, PNAS, 81:498, 1984; Anson DS, EMBO J, 3:1053, 1984 |
| N/K | Factor X | h-cDNA | | Leytus SP, PNAS, 81:3699, 1984 |
| Dysfibrinogenemia Disorder | Fibrinogen A, alpha | h-cDNA | LV - CMV - hc-DNA - (CS) - hNGF | Kant JA, PNAS, 80:3953, 1983 |
| Cardiovascular Disease | B beta, gamma | h-gDNA (gamma) h-cDNA (alpha gamma) h-gDNA (gamma) | LV - CMV - h-gDNA - (CS) - h-cDNA | Fornace AJ, Sci, 224:161, 1984; Imam AMA, NAR, 11:7427, 1983; Fornace AJ, JBC, 259:12826, 1984 |
| Respiratory Disease | Gastrin releasing peptide | h-cDNA | LV - CMV - h-cDNA - (CS) - RNAi (IL-2) | Spindel ER, PNAS, 81:5699, 1984 |
| Human Diabetes | Glucagon, prepro. | hamster-cDNA h-gDNA | LV - CMV - h-gDNA - (CS) - h-gDNA | Bell GI, Nat, 302:716, 1983; Bell GI, Nat, 304:368, 1983 |
| Growth Hormone Deficiency and Other Growth Disorders i.e., Creutzfeldt-Jakob Disease | Growth hormone | h-cDNA h-gDNA GH-like gene | LV - CMV - h-cDNA - (CS) - h-gDNA | Martial JA, Sci, 205:602, 1979; DeNoto FM, NAR, 9:3719, 1981; Owerbach, D, Sci, 209:289, 1980 |
| Growth Hormone Deficiency and Other Growth Disorders i.e., Creutzfeldt-Jakob Disease | Growth hormone, RF | h-cDNA | LV - CMV - h-cDNA - (CS) - IGF-1 | Gubler V, PNAS, 80:3411, 1983 |
| Acromegaly | Somatocrinin | h-cDNA | LV - CMV - h-cDNA - (CS) - RNAi (GH&H) | Mayo KE, Nat, 306:86:1983 |
| Retina Disease | Hemopexin | h-cDNA | LV - CMV - h-cDNA - (CS) - BXL-xl | Stanley KK, EMBO J, 3:1439, 1984 |
| Trophoblastic Disease | Inhibin | porcine-cDNA | LV - CMV - p-cDNA - (CS) - EGFP | Mason AJ, Nat, 318:659, 1985 |

FIG. 7 (Continued)

| ELEMENT / INDICATION | Cloned Structural Gene | Clone Type | Exemplary Construct | Reference |
|---|---|---|---|---|
| Obesity Syndrome | Insulin, prepro | h-gDNA | LV - CMV - h-gDNA - (CS) - RNAi (fatty acid) | Ullrich A, Sci, 209:612, 1980 |
| Ischemic Heart Disease Amyotrophic Lateral Sclerosis | Insulin-like growth factor I | h-cDNA h-cDNA Chr | LV - CMV - h-cDNA - (CS) - Chr | Jansen M, Nat, 306:609, 1983; Bell GI, Nat, 3 10:775, 1984; Brissenden JE, Nat, 310:781, 1984 |
| Chronic Liver Disease | Insulin-like growth factor II | h-cDNA h-gDNA Chr | LV - CMV - h-cDNA - (CS) - h-gDNA - (CS) - Chr. | Bell GI, Nat, 310:775, 1984; Dull TJ, Nat, 310:777, 1984; Brissenden JE, Nat, 310:781, 1984 |
| Hemophilia/Von-Willebrand's Disease Hepatitis Disease | Interferon, alpha (leukocyte), multiple | h-cDNA h-cDNA h-gDNA h-gDNA h-gDNA | LV - CMV - h-cDNA - (CS) - h-gDNA - | Maeda S, PNAS, 77:7010, 1980; Goeddel DV, NAT, 290:20, 1981; Lawn RM, PNAS, 78:5435, 1981; Todokoro K, EMBO J, 3:1809, 1984; Torczynski RM, PNAS, 81:6451, 1984 |
| Regulation of Immune Response to Viral Infection Rheumatic/Inflammation Diseases | Interferon, beta (fibroblast) | h-cDNA h-gDNA h-gDNA (related) h-gDNA (related) h-cDNA | LV - CMV - h-gDNA - (CS) - h-cDNA | Taniguchi T, Gene; 10:11, 1980; Lawn RM, NAR, 9:1045, 1981; Sehgal P, PNAS, 80:3632, 1983; Sagar AD, Sci, 223:1312, 1984; Gray PW, Nat, 295:503, 1982 |
| Rheumatoid Arthritis Disease | Interferon, gamma (immune) | h-cDNA h-gDNA | LV - CMV - h-cDNA - (CS) - h-gDNA | Gray PW, Nat, 298:859, 1982 |
| Rheumatoid Arthritis | Interleukin-1 | m-cDNA | LV - CMV - m-cDNA - (CS) - EGFP | Lomedico PT, Nat, 312:458, 1984 |
| HIV-Therapy | Interleukin-2 | h-cDNA | LV - CMV - h-cDNA - (CS) - RNAi (Pol) | Devos R, NAR, 11:4307, 1983 |
| Immunoregulatory - IL-2 | T-cell Growth factor | h-cDNA h-gDNA Chr | LV - CMV - h-cDNA - (CS) - h-gDNA - (CS) - Chr. | Taniguchi T, Nat, 302:305, 1983; Holbrook NJ, PNAS, 81:1634, 1984; Siege LF, Sci, 223:175, 1984 |
| Autoimmune Disease Myeloproliferative Disease | Interleukin-3 | m-cDNA | LV - CMV - m-cDNA - (CS) - EGFP | Fung MC, Nat, 307:233, 1984 |
| Rheumatoid Disease | Kininogen, two forms | bovine-cDNA bovine-cDNA and gDNA | LV - CMV - h-cDNA - (CS) - gDNA | Nawa H, PNAS, 80:90, 1983; Kitamura N, Nat, 305:545, 1983 |
| Gynecologic Disease | Luteinizing hormone, beta subunit | h-gDNA and Chr | LV - CMV - h-gDNA - (CS) - Chr | Talmadge K, Nat, 307:37, 1984 |

FIG. 7 (Continued)

| ELEMENT / INDICATION | Cloned Structural Gene | Clone Type | Exemplary Construct | References |
|---|---|---|---|---|
| Disorders of Reproductive Endocrine System | Luteinizing hormone releasing hormone | h-cDNA and gDNA | LV - CMV - h-cDNA - (CS) - gDNA | Seeburg PH, Nat, 311:666, 1984 |
| Liver Related Disease | Lymphotoxin | h-cDNA and gDNA | LV - CMV - h-cDNA - (CS) - gDNA | Gray PW, Nat, 312:721, 1984 |
| Cutaneous Mastocytoma Atherosclerosis | Mast cell growth factor | m-cDNA | LV - CMV - m-cDNA - CS) - RNAi | Yokoya T, PNAS, 81:1070, 1984 |
| Neurological Disorders | Nerve growth factor, beta subunit | m-cDNA h-gDNA Chr | LV - CMV - h-gDNA - (CS) - Chr - (CS) - NGF | Scott J, Nat, 302:538, 1983; Ullrich A, Nat, 303:821, 1983; Franke C, Sci, 222:1248, 1983 |
| Autoimmune Disease | Oncogene, c-sis, PGDF | h-gDNA | LV - CMV - h-gDNA - CS) - P53 | Dalla-Favera R, Nat, 295:31, 1981 |
| Pancreatic Disease | Pancreatic polypeptide and icosapeptide | h-cDNA h-cDNA | LV - CMV - h-cDNA - (CS) - h-gDNA | Clarke ME, Nat, 208:464, 1984; Boel E, EMBO J, 3:909, 1984 |
| Pseudo Hypoparathyroidism | Parathyroid hormone, prepro | h-cDNA h-gDNA | LV - CMV - h-cDNA - (CS) - h-gDNA | Hendy GN, PNAS, 78:7365, 1981; Vasicek TJ, PNAS, 80:2127, 1983 |
| Liver Disease | Plasminogen | h-cDNA and gDNA | LV - CMV - h-cDNA - (CS) - gDNA | Malinowski DP, Fed P, 42:1761, 1983 |
| Cardiometabolic Disorder | Plasminogen activator | h-cDNA h-cDNA h-gDNA h-cDNA r-gDNA | LV - CMV - h-cDNA - (CS) - h-gDNA - (CS) - r-gDNA | Edlund T, PNAS, 80:349, 1983; Pennica D, Nat, 301:214, 1983; Ny T, PNAS, 81:5355, 1984; Cook ME, JBC, 256:4007, 1981; Cooke NE, Nat, 297:603, 1982 |
| Cushing's Disease | Proopiomelanocortin | h-cDNA h-gDNA | LV - CMV - h-cDNA - (CS) - h-gDNA | DeBold CR, Sci, 220:721, 1983; Cochet M, Nat, 297:335, 1982 |
| Congenital Thrombotic Disease | Protein C | h-cDNA | LV - CMV - h-cDNA - (CS) - h-cDNA | Foster D, PNAS, 81:4766, 1984 |
| Coronary Heart Disease | Prothrombin | bovine-cDNA | LV - CMV - b-cDNA - (CS) - GFP | MacGillivray RTA, PNAS, 77:5153, 1980 |
| Vasoconstriction Disease | Relaxin | h-gDNA h-cDNA (2 genes) Chr | LV - CMV - h-gDNA - (CS) - h-cDNA - (CS) - Chr | Hudson P, Nat, 301:628, 1983; Hudson P, EMBO J, 3:2333, 1984; Crawford, RJ, EMBO J, 3:2341, 1984 |

FIG. 7 (Continued)

| ELEMENT / INDICATION | Cloned Structural Gene | Clone Type | Exemplary Construct | Reference |
|---|---|---|---|---|
| Diabetic Renal Disease | Renin, prepro | h-cDNA<br>h-gDNA<br>h-gDNA<br>Chr | OV - CMV - h-cDNA - (CS) - h-gDNA - (CS) - Chr | Imai T, PNAS, 80:7405, 1983; Hobart PM, PNAS 81:5026, 1984; Miyazaki H, PNAS, 81:5999, 1984; Chirgwin JM, SCMG, 10:415, 1984 |
| Pituitary Disease Huntington's Disease | Somatostatin | h-cDNA<br>h-gDNA and Ri-IP | LV - CMV - h-cDNA - (CS) - h-gDNA - (CS) - Ri-IP | Shen IP, PNAS, 79:4575, 1982; Naylor SL, PNAS, 80:2686, 1983 |
| Inflammatory Disease | Substances P & K | bovine-gDNA | LV - CMV - h-gDNA - (CS) - opioid analogous gene | Nawa H, Nat, 312:729, 1984 |
| Gastroenterological Therapy | Tachykinin, prepro | bovine-cDNA | LV - CMV - h-cDNA - (CS) - EGFP | Nawa H, Nat, 306:32, 1983 |
| Thromboembolic Disease | Urokinase | h-cDNA | LV - CMV - h-cDNA - (CS) - NGF | Verde P, PNAS, 81:4727, 1984 |

FIG. 9

Selected Cloned Structural Genes

|   | Gene | | Clone Type | Reference |
|---|---|---|---|---|
| 1 | LV-CMV-pcDNA-(cs)-EGFP | Activin | Porcine-cDNA Adrenal gland disease | Mason AJ, Nat, 318:659, 1985 |
| 2 | LV-CMV-hcDNA-(cs)-RNAi (fatty acid) | Adenosine deaminase (Coronary Artery disease) | h-cDNA | Wiginton DA, PNAS, 80:7481, 1983 |
| 3 | LV-CMV-(r)cDNA-(cs)-r-gDNA | Angiotensinogen1 (Cardiovascular disease) | r-cDNA r-gDNA | Ohkubo H, PNAS, 80:2196, 1983; Tanaka T, JBC, 259: 8063, 1984 |
| 4 | LV-CMV-hcDNA-(cs)-AFP-gDNA Liver disease | Antithrombin III (Congenital antithrombin IV deficiency) | h-cDNA h-cDNA and gDNA | Bock SC, NAR 10:8113, 1982; Prochownik EV, JBC, 258:8389, 1983 |

FIG. 9 (Continued)

Selected Cloned Structural Genes

| | | Gene | Clone Type | Reference |
|---|---|---|---|---|
| 5 | LV-CMV-hcDNA-(cs)-h-gDNA(RFLP) | Antitrypsin, alpha 1 (α-antitrysin deficiency Lung Disease) | h-cDNA h-gDNA RFLP | Kurachi K, PNAS, 78:6826, 1981; Leicht M, Nat. 297:655, 1982; Cox DW, AJHG, 36:134S, 1984 |
| 6 | LV-CMV-hcDNA-(cs)-h-gDNA-(cs)-RFLP | Apolipoprotein A-I Tangier disease with coronary artery disease | h-cDNA, h-gDNA RFLP h-gDNA | Shoulders CC, NAR, 10:4873, 1982; Karathanasis SK, Nat. 301: 718, 1983; Karathanasis SK, PNAS, 80:6147, 1983 |
| 7 | LV-CMV-h-cDNA-(cs)-Chr | Apolipoprotein A-II Coronary artery disease | h-cDNA Chr h-cDNA | Sharpe CR, NAR, 12:3917, 1984; Sakaguchi, AY, AJHB, 36:207S, 1984; Knott TJ, BBRC, 120:734, 1984 |
| 8 | LV-CMV-hcDNA-(cs)-RNAi(β-amyloid) | Apolipoprotein C-I Risk factor for Alzheimer's disease | h-cDNA | Knott TJ, NAR, 12:3909, 1984 |
| 9 | LV-CMV-hcDNA-(cs)-RFLP | Apolipoprotein C-II Premature vascular disease | h-cDNA h-cDNA h-cDNA RFLP | Jackson CL, PNAS, 81:2945, 1985; Mykelbost O, JBC, 249:4401, 1984; Fojo SS, PNAS, 81:6354, 1984; Humphries SE, C Gen, 26:389, 1984 |
| 10 | LV-CMV-hcDNA-(cs)-h-cDNA | Apolipoprotein C-III Cardiovascular disease with metabolic syndrome (TRL = triacylglycerolyich lipoprotein) | h-cDNA and gDNA h-cDNA | Karathanasis SK, Nat. 304:371, 1983; Sharpe CR, NAR, 12:3917, 1984 |
| 11 | LV-CMV-hcDNA-(cs)-RNAi(β-amyloid) | Apolipoprotein E Cerebral palsy Alzheimer's disease | h-cDNA | Breslow JL, JBC, 257: 14639, 1982 |

FIG. 9 (Continued)

Selected Cloned Structural Genes

| | Gene | | Clone Type | Reference |
|---|---|---|---|---|
| 12 | LV-CMV-h-gDNA-(cs)-hcDNA | Atrial natriuretic factor<br>Congenital heart disease | h-cDNA<br>h-cDNA<br>h-cDNA<br>h-gDNA<br>h-gDNA<br>h-gDNA | Oikawa S, Nat, 309:724, 1984; Nakayama K, Nat, 310:699, 1984; Zivin RA, PNAS, 81: 6325, 1984; Seidman CE, Sci, 226: 1206, 1984; Nemer M, Nat, 312:654, 1984; Greenberg BI, Nat, 312:665, 1984 |
| 13 | LV-CMV-hcDNA-(cs)-RFLP | Chorionic gonadotropin, alpha chain<br>Crohn's disease<br>Inflammatory bowel disease | h-cDNA<br>RFLP | Fiddes JC, Nat, 281:351, 1981; Boothby M, JBC, 256:5121, 1981 |
| 14 | LV-CMV-hcDNA-(cs)-h-gDNA | Chorionic gonadotropin, beta chain<br>Gestational trophoblastic disease | h-cDNA<br>h-gDNA<br>h-gDNA | Fiddes JC, Nat, 286:684, 1980; Boorstein WR, Nat, 300:419, 1982; Talmadge K, Nat, 307:37, 1984 |
| 15 | LV-CMV-h-cDNA-(cs)-EGFP | Chymosin, pro (rennin)<br>Infectious disease | Bovine-cDNA | Harris TJR, NAR, 10:2177, 1982. |
| 16 | LV-CMV-hcDNA-(cs)-gDNA | Complement, factor B<br>Coeliac disease | h-cDNA<br>h-cDNA and gDNA | Woods DE, PNAS, 79:5661, 1982; Duncan R, PNAS, 80:4464, 1983 |
| 17 | LV-CMV-hcDNA-(cs)-hgDNA | Complement C2<br>Grave's Disease | h-cDNA<br>h-Gdna (C2, C4, and B) | Bentley DR, PNAS, 81:1212, 1984; Carroll MC, Nat, 307: 237, 1984 |
| 18 | LV-CMV-hcDNA-(cs)-m-Gdna | Complement C3<br>Renal disease | m-cDNA<br>h-gDNA | Domdey H, PNAS, 79:7619, 1983; Whitehead AS, PNAS, 79:5021, 1982 |
| 19 | LV-CMV-h-cDNA-(cs)-gDNA | Complement C4<br>Lupus disease | h-cDNA and gDNA | Carroll MC, PNAS, 80:264 |

FIG. 9 (Continued)

Selected Cloned Structural Genes

| | | Gene | Clone Type | Reference |
|---|---|---|---|---|
| 20 | LV-CMV-hcDNA-(cs)-EGFP | Complement C9 | h-cDNA<br>h-c-DNA | 1983; Whitehead AS, PNAS, 80:5387, 1983; DiScipio RC, PNAS, 81:7298, 1984 |
| 21 | LV-CMV-h-gDNA-(cs)RNAi (β-amyloid) | Corticotropin releasing factor<br>Alzheimer's disease<br>A stress factor | Sheep-cDNA<br>h-gDNA | Furutani Y, Nat, 301:537, 1983; Shibahara S, EMBO J, 2:775, 1983 |
| 22 | LV-CMV-h-gDNA-(cs)-m-cDNA | Epidermal growth factor<br>Salivary disease<br>Prostate disease/cancer | m-cDNA<br>m-cDNA<br>h-gDNA | Gray A, Nat, 303:722, 1983; Shibahara S, EMBO J, 2: 775, 1983 |
| 23 | LV-CMV-h-cDNA-(cs)-Chr | Epidermal growth factor receptor, oncogene c-erb B<br>Tongue (oral) cancer | h-cDNA and Chr | Lin CR, Sci, 224:843, 1984 |
| 24 | LV-CMV-r-cDNA-(cs)-EGFP | Epoxide dehydratase<br>Immuno disorder | r-cDNA | Gonzalez FJ, JBC, 256:4697, 1981 |
| 25 | LV-CMV-h-cDNA-(cs)-RNAi (fatty acid) | Erythropoietin<br>Congenital heart disease | h-cDNA | Lee-Huang S, PNAS, 81:2708, 1984 |
| 26 | LV-hcDNA-(cs)-RNAi (IL-2) | Esterase inhibitor, dehydratase<br>Inflammation disease | h-cDNA | Stanley KK, EMBO J,3:1429, 1984 |
| 27 | | Factor VIII | h-cDNA and gDNA<br>h-cDNA | Gitschier J, Nat, 312:326, 1984; Toole JJ, Nat, 312:342, 1984 |
| 28 | | Factor IX,<br>Christmas factor | h-cDNA<br>h-cDNA<br>RFLP<br>h-gDNA | Kurachi K, PNAS, 79:6461, 1982; Choo KH, Nat, 299:178, 1982; Camerino G, PNAS, 81:498, 1984; Anson DS, EMBO J, 3: 1053, 1984 |
| 29 | | Factor X | h-cDNA | Leytus SP, PNAS, 81:3699, 1984 |

FIG. 9 (Continued)

Selected Cloned Structural Genes

| | | Gene | Clone Type | Reference |
|---|---|---|---|---|
| 29 | LV-CMV-hcDNA-(cs)-hNGF | Fibrinogen A, alpha Dysfibrinogenemia disorder | h-cDNA | Kant JA, PNAS, 80:3953, 1983 |
| 30 | LV-CMV-h-gDNA-(cs)-h-cDNA | B beta, gamma Cardiovascular disease | h-gDNA (gamma) h-cDNA (alpha gamma) h-gDNA(gamma) | Fornace AH, Sci. 224:161, 1984; Imam AMA, NAR, 11:7427, 1983; Fornace AJ, JBC, 259:12826, 1984 |
| 31 | LV-CMV-h-cDNA-(cs)-RNAi(IL-2) | Gastrin releasing peptide Respiratory disease | h-cDNA | Spindel ER, PNAS, 81:5699, 1984 |
| 32 | LV-CMV-h-Gdna-(cs)-h-insulin | Glucagon, prepro Human diabetes | hamster-cDNA h-gDNA | Bell GI, Nat. 302:716, 1983; Bell GI, Nat. 304:368, 1983 |
| 33 | LV-CMV-h-cDNA-(cs)-h-gDNA | Growth hormone Growth hormone deficiency and other growth disorders i.e. Creutzfeldt-Jakob disease | h-cDNA h-gDNA GH-like gene | Martial JA, Sci. 205:602, 1979; DeNoto FM, NAR, 9:3719, 1981; Owerbach, D, Sci. 209:289, 1980 |
| 34 | LV-CMV-h-cDNA-(cs)-IGF-1 | Growth hormone, RF Same as above | h-cDNA | Gubler V, PNAS, 80:3411, 1983 |
| 35 | LV-CMV-h-cDNA-(cs)-RNAi(FHRH) | Somatocrinin Acromegaly | h-cDNA | Mayo KR, Nat. 306:86,1983 |
| 36 | LV-CMV-h-cDNA-(cs)-BCL-xP | Hemopexin Retina disease | h-cDNA | Stanley KK, EMBO J, 3: 1429, 1984 |
| 37 | LV-CMV-p-cDNA-(cs)-EGFP | Inhibin Trophoblastic disease | Porcine-cDNA | Mason AJ, Nat. 318:659,1985 |
| 38 | LV-CMV-h-gDNA-(cs)-RNAi (fatty acid) | Insulin, prepro Obesity syndrome | h-gDNA | Ullrich A, Sci. 209:612, 1980 |
| 39 | LV-CMV-hcDNA-(cs)-Chr | Insulin-like growth factor I Ischemic heart disease amyotrophic lateral sclerosis | h-cDNA h-cDNA Chr | Jansen M, Nat. 306:609, 1983; Bell GI, Nat, 310:775, 1984; Brissenden JE, Nat, 310:781, 1984 |

FIG. 9 (Continued)

Selected Cloned Structural Genes

| | | Gene | Clone Type | References |
|---|---|---|---|---|
| 40 | LV-CMV-h-cDNA-(cs)-Chr | Insulin-like growth factor II<br>Chronic liver disease | h-cDNA<br>h-gDNA<br>Chr | Bell GI, Nat, 310:775, 1984; Dull TJ, Nat, 310:777, 1984; Brissenden JE, Nat, 310:781, 1984 |
| 41 | LV-CMV-h-cDNA-(cs)-h-gDNA | Interferon, alpha (leukocyte), multiple<br>Hemophilia/Von-Willebrand's disease<br>Hepatitis disease | h-cDNA<br>h-cDNA<br>h-gDNA<br>h-gDNA<br>h-gDNA | Maeda S, PNAS, 77:7010, 1980; Goeddel DV, NAT, 290:20, 1981; Lawn RM, PNAS, 78:5435, 1981; Todokoro K, EMBO J, 3:1809, 1984; Torczynski RM, PNAS, 81:6451, 1984 |
| 42 | LV-CMV-h-gDNA-(cs)-h-cDNA | Interferon, beta (fibroblast)<br>Regulation of immune response in viral infections<br>Rheumatic/inflammation disease | h-cDNA<br>h-gDNA<br>h-gDNA (related)<br>h-gDNA (related)<br>h-cDNA | Taniguchi T, Gene, 10:11, 1980; Lawn RM, NAR, 9:1045, 1981; Sehgal P, PNAS, 80:3632, 1983; Sager AD, Sci, 223:1312, 1984; Gray PW, Nat, 295:503, 1982; |
| 43 | LV-CMV-h-cDNA-(cs)-h-gDNA | Interferon, gamma (immune) rheumatoid arthritis disease | h-cDNA<br>h-gDNA | Gray PW, Nat, 298:859, 1982 |
| 44 | LV-CMV-h-cDNA-(cs)-EGFP | Interleukin-1<br>Rheumatoid arthritis | m-cDNA | Lomedico PT, Nat, 312:458, 1984 |
| 45 | LV-CMV-h-cDNA-(cs)-RNAi(pol) | Interleukin-2<br>HIV-Therapy | h-cDNA | Devos R, NAR, 11:4307, 1983 |
| 46 | LV-CMV-hcDNA-(cs)-h-gDNA-(cs)-Chr | T-cell Growth factor<br>Immunoregulatory<br>IL-2 | h-cDNA<br>h-gDNA<br>Chr | Taniguchi T, Nat, 302:305, 1983; Holbrook NJ, PNAS, 81:1634, 1984; Siegel LF, Sci, 223:175, 1984 |

FIG. 9 (Continued)

| | Gene | | Selected Cloned Structural Genes | |
|---|---|---|---|---|
| | | | Clone Type | Reference |
| (47) | LC-CMV-m-cDNA-(CS)-EGFP | Interleukin-3 Autoimmune disease myeloproliferating disease | m-cDNA | Fung MC, Nat, 307:233, 1984 |
| (48) | LV-CMV-bcDNA-(CS)-gDNA | Kininogen, two forms Rheumatoid disease | bovine-cDNA | Nawa H, PNAS, 80:90,1983; |
| | | | bovine, -cDNA and gDNA | Kitamura N, Nat, 305:545,1983 |
| (49) | LV-CMV-h-gDNA-(CS)-chr | Luteinizing hormone, beta subunit Gynecologic disease | h-gDNA and Chr | Talmadge K, Nat, 207:37, 1984 |
| (50) | LV-CMV-hcDNA(CS)-gDNA | Luteinizing hormone disorders of reproductive endocrine system releasing hormone | h-cDNA and gDNA | Seeburg PH, Nat, 311:666, 1984 |
| (51) | LV-CMV-hcDNA-(CS)-gDNA | Lymphotoxin Liver related disease | h-cDNA and gDNA | Gray PW, Nat, 312:721, 1984 |
| (52) | LV-CMV-m-cDNA-(CS)-RNAi | mast cell growth factor Cutaneous mastocytoma atherosclerosis | m-cDNA | Yokoya T, PNAS, 81:1070, 1984 |
| (53) | LV-CMV-h-gDNA-(CS)-Chr-(CS)-NGF | nerve growth factor, beta subunit Neurological disorders | m-cDNA | Scott J, Nat, 302:538,1983; |
| | | | h-gDNA | Ullrich A, Nat, 303:821, 1983; |
| | | | Chr | Franke C, Sci, 222:1248, 1983 |
| (54) | LV-CMV-h-gDNA-(CS)-P53 | oncogene, c-sis, PGDF autoimmune disease | h-gDNA | Dalla-Favera R, Nat, 295:31, 1981 |
| (55) | LV-CMV-h-cDNA-(CS)-RNAi | Pancreatic polypeptide and icosapeptide pancreatic disease | h-cDNA | Clarke MF, Nat, 208:464, 1984 |
| | | | h-cDNA | Boel E, EMBO J, 3:909, 1984 |
| (56) | LV-CMV-hcDNA-(CS)-hgDNA | Parathyroid hormone, prepro Pseudotypopasa thyroidi-ism | h-cDNA | Hendy GN, PNAS, 78:7365, 1981; |
| | | | h-gDNA | Vasicek TJ, PNAS, 80:2127, 1983 |
| (57) | LV-CMV-hcDNA-(CS)-gDNA | Plasminogen Liver disease | h-cDNA and gDNA | Malinowski DP, Fed P, 42:1761, 1983 |
| (58) | LV-CMV-hcDNA-(CS)-hgDNA-(CS)-r-g-DNA | Plasminogen activator Cardiometabolic disorder | h-cDNA | Edlund T, PNAS, 80:349, 1983; |
| | | | h-cDNA | Pennica D, Nat, 301:214, 1983; |
| | | | h-gDNA | Ny T, PNAS |

FIG. 9 (Continued)

| | Gene | Selected Cloned Structural Genes | |
|---|---|---|---|
| | | Clone Type | Reference |
| | | h-cDNA | 81:5355, 1984; Cook NE, JBC, 256:4007, 1981; Cooke NE, Nat, 297:603, 1982 |
| | | r-gDNA | |
| (59) | LV-CMV-h-cDNA-(CS)-h-gDNA | Proopiomelanocortin Cushing's disease | h-cDNA | Debold CR, Sci, 220:721, 1983; Cochet M, Nat, 297:335, 1982 |
| | | | h-gDNA | |
| (60) | LV-CMV-h-cDNA-(CS)-hcDNA | Protein C Congenital thrombotic disease | h-cDNA | Foster D, PNAS, 81:4766, 1984 |
| (61) | LV-CMV-bcDNA-(CS)-GFP | Prothrombin Coronary heart disease | bovine-cDNA | MacGillivray RTA, PNAS, 77:5153, 1980 |
| (62) | LV-CMV-h-gDNA-(CS)-h-cDNA-(CS)-chr | Relaxin Vasoconstriction disease | h-gDNA | Hudson P, Nat, 301:628, 1983; Hudson P, EMBO J, 3:2333, 1984; Crawford RJ, EMBO J, 3:2341, 1984 |
| | | | h-cDNA (2 genes) | |
| | | | Chr | |
| (63) | LV-CMV-h-cDNA-(CS)-h-gDNA-(CS)-Chr | renin, prepro diabetic renal disease | h-cDNA | Imai T, PNAS, 80:7405, 1983; Hobart PM, PNAS, 81:5026, 1984; Miyazaki H, PNAS, 81:5999, 1984; Chirgwin JM, SCMG, 10:415, 1984 |
| | | | h-gDNA | |
| | | | h-gDNA | |
| | | | Chr | |
| (64) | LV-CMV-hcDNA-(CS)-h-gDNA-(CS)-Ri-IP | Somatostatin Pituitary disease huntington's disease | h-cDNA | Shen LP, PNAS, 79:4575, 1982; Naylor SL, PNAS, 80:2686, 1983 |
| | | | h-gDNA and Ri-IP | |
| (65) | LV-CMV-b-gDNA-(CS)-opioid analogous gene | Substances P & K inflammatory disease | bovine-gDNA | Nawa H, Nat, 312:729, 1984 |
| (66) | LV-CMV-b-cDNA-(CS)-EGFP | Tachykinin, prepro, Gastroenterological therapy | bovine-cDNA | Nawa, Nat, 306:32, 1983 |
| (67) | LV-CMV-hcDNA-(CS)-NGF | Urokinase Thromboembolic disease | h-cDNA | Verde P, PNAS, 81:4727, 1984 |

FIG. 14A

| Group Name | Day 7 | | Day 12 | | Tumor Growth Rate** |
|---|---|---|---|---|---|
| | Tumor Size L x W x H = Vol. (mm³) | | Tumor Size L x W x H = Vol. (mm³) | | |
| | Individual | Average | Individual | Average | |
| V1 | 180.00 | 309.6 | 31.50 | 61.3 | -80.2% |
| | 224.00 | | 90.00 | | |
| | 360.00 | | 64.00 | | |
| | 300.00 | | 24.00 | | |
| | 432.00 | | 96.00 | | |
| V2 | 540.00 | 346.8 | 72.00 | 72.6 | -79.1% |
| | 240.00 | | 90.00 | | |
| | 440.00 | | 63.00 | | |
| | 264.00 | | 50.00 | | |
| | 252.00 | | 70.00 | | |
| V3 | 450.00 | 393.1 | 126.00 | 99.4 | -74.7% |
| | 360.00 | | 140.00 | | |
| | 260.00 | | 100.00 | | |
| | 420.00 | | 64.00 | | |
| | 405.00 | | 50.00 | | |
| PC | 64.00 | 34.6 | 90.00 | 109.8 | 217.8% |
| | 6.00 | | 48.00 | | |
| | 50.00 | | 162.00 | | |
| | 75.00 | | 120.00 | | |
| | 12.00 | | 150.00 | | |
| Remark | 1st time drug injection | | 2nd time drug injection | | |

FIG. 14B

| Group Name | Day 16 | | | Day 21 | | |
|---|---|---|---|---|---|---|
| | Tumor Size L x W x H = Vol. (mm³) | | Tumor Growth Rate | Tumor Size L x W x H = Vol. (mm³) | | Tumor Growth Rate |
| | Individual | Average | | Individual | Average | |
| V1 | 8.00<br>62.50<br>45.00<br>6.00<br>147.00 | 41.8 | -86.5% | 0.50<br>8.00<br>30.00<br>0.02<br>60.00 | 10.2 | -96.7% |
| V2 | 31.50<br>60.00<br>70.00<br>13.50<br>62.50 | 45.4 | -86.9% | 15.00<br>40.00<br>40.00<br>1.00<br>48.00 | 23.0 | -93.4% |
| V3 | 90.00<br>84.00<br>67.50<br>22.50<br>4.00 | 44.8 | -88.6% | 30.00<br>48.00<br>18.00<br>18.00<br>0.20 | 17.1 | -95.7% |
| PC | 150.00<br>70.00<br>192.00<br>100.00<br>220.00 | 143.5 | 315.3% | 225.00<br>165.00<br>360.00<br>234.00<br>200.00 | 246.2 | 612.5% |
| Remark | 3rd time drug injection | | | 4th time drug injection | | |

FIG. 14C

| Group Name | Day 28 | | | | | Ratio of Tumor Weight/Starting Tumor Size** (mg/mm³) |
|---|---|---|---|---|---|---|
| | Tumor Size L x W x H ≈ Vol. (mm³) | | Tumor Growth Rate | Tumor Weight (mg) | | |
| | Individual | Average | | Individual | Average | |
| V1 | 180.00 | 20.5 | -93.4% | 280.0 | 132.0 | 0.43 |
| | 24.00 | | | 220.0 | | |
| | 20.00 | | | 90.0 | | |
| | 0.00 | | | 30.0 | | |
| | 6.00 | | | 40.0 | | |
| V2 | 25.00 | 33.0 | -90.5% | 270.0 | 250.0 | 0.72 |
| | 250.00 | | | 350.0 | | |
| | 12.00 | | | 200.0 | | |
| | 10.00 | | | 400.0 | | |
| | 6.00 | | | 30.0 | | |
| V3 | 160.00 | 24.9 | -93.7% | 220.0 | 176.0 | 0.45 |
| | 40.00 | | | 290.0 | | |
| | 1.20 | | | 190.0 | | |
| | 24.00 | | | 140.0 | | |
| | 0.10 | | | 40.0 | | |
| PC | 1050.00 | 1026.4 | 2870.0% | 1350.0 | 1303.0 | 37.70 |
| | 1260.00 | | | 1170.0 | | |
| | 960.00 | | | 1210.0 | | |
| | 1600.00 | | | 1580.0 | | |
| | 450.00 | | | 1205.0 | | |
| Remark | 5th time injection | | | | | |

SAFE LENTIVIRAL VECTORS FOR TARGETED DELIVERY OF MULTIPLE THERAPEUTIC MOLECULES

CROSS-REFERENCE TO RELATED APPLICATIONS

The Sequence Listing originally submitted in prior application Ser. No. 13/333,882 on Dec. 21, 2011 is incorporated herein by reference. A paper copy of the Sequence listing is submitted electronically herewith.

The present application is a continuation of U.S. application Ser. No. 16/687,525 filed on Nov. 18, 2019, which is a divisional application of U.S. application Ser. No. 13/333,882, filed on Dec. 21, 2011, which is a continuation of U.S. application Ser. No. 12/581,871 filed Oct. 19, 2009, which claims the benefit of priority to U.S. Provisional Application No. 61/243,121, filed Sep. 16, 2009; U.S. Provisional Application No. 61/116,138, filed Nov. 19, 2008; and U.S. Provisional Application No. 61/196,457, filed Oct. 17, 2008, the contents of each of which are incorporated by reference herein in their entireties.

BACKGROUND OF THE INVENTION

1. Field of the Invention

The present invention relates to the field of medicine, specifically to delivery of multiple therapeutic molecules strategically combined with regulatory elements, using a safe for human use, highly and long-term expressing in human subject lentiviral gene transfer vector for the treatment of a condition, disease or disorder.

2. General Background and State of the Art

The present application relates to a gene transfer vector that provides versatility, control, high expression, stable multiple gene expression, tolerability, and safety, for the design of effective gene therapies for disease. Virus vectors in development each have limitations for researchers to address.

Identification of target genes involved in neoplastic transformation and tumor progression has encouraged the idea that nucleotide sequences of cancer-relevant genes could lead to the development of tailored anticancer agents that lack many of the toxic side effects of traditional cytotoxic drugs. Mutations of the p53 gene are associated with transformation to a malignant phenotype. Transfer of wild-type P53, which plays a critical role in the regulation of cell growth and downregulation of genes that contribute to cancer progression, is hoped to result in selective and specific inhibition of tumor growth while minimizing undesirable side effects on normal cells. Delivery of the p53 gene has been reported in a replication-deficient adenoviral vector containing the wild-type p53 gene sequence. Functional activity and expression of the transgene product in tumor cells treated with the adenoviral vector has been reported. (Baker, et al., 1990, Suppression of human colorectal carcinoma cell growth by wild-type p53, Science 249: 912-915.) Two adenovirus-based gene therapeutics for the treatment of cancer were recently commercialized in China. These two agents, combined with chemotherapy, have been used there as an alternative treatment for some types of refractory cancer. (Peng, 2005, Current Status of Gendicine in China: Recombinant Human Ad-p53 Agent for Treatment of Cancers, Hum. Gene Ther. 16, 1016-1027; Yu, W., and Fang, H., 2007, Clinical Trials with Oncolytic Adenovirus in China. Curr. Cancer Drug Targets 7, 141-148). Although adenovirus vectors can efficiently deliver therapeutic genes in both dividing and non-dividing cells, and can be manufactured at high viral titers, adenovirus vectors are highly immunogenic (Shirakawa, et al., 2008, The Current Status of Adenovirus-based Cancer Gene Therapy, Mol. Cells 25(4): 462-466). Furthermore, long-term expression in target tissues is not observed.

Lentiviruses, such as HIV, are "slow viruses." Vectors derived from lentiviruses can be expressed long-term in the host cells after a few administrations to the patients, e.g., via ex vivo transduced bone marrow stem cells. For most diseases and disorders, including genetic diseases, cancer, and neurological disease, long-term expression is crucial to successful treatment. Safety has been a concern with lentiviral vectors, but a number of strategies for eliminating the ability of lentiviral vectors to replicate have now been described. For example, the deletion of promoter and enhancer elements from the U3 region of the long terminal repeat (LTR) are thought to have no LTR-directed transcription. The resulting vectors are called "self-inactivating" (SIN). However, it has been reported that HIV-1-derived vectors containing the SIN deletion in the U3 region of the LTR are capable of expressing full-length genomic transcripts (Logan, et al., 2004, Integrated Self-Inactivating Lentiviral Vectors Produce Full-Length Genomic Transcripts Competent for Encapsidation and Integration, J. Virology 78(16): 8421-8436). Therefore, combination of this deletion with other safety measures must be considered.

The last few years have seen immense excitement regarding the use of RNAi agents for disease therapies. Investigators reported that they were able to specifically silence mutant oncogenic ras without affecting wild-type ras in vitro (Zhang, et al., 1995, Safety evaluation of Ad5CMV-p53 in vitro and in vivo, Human Gene Therapy 6:155-164; Ishii, et al., 2001, Potential cancer therapy with the fragile histidine triad gene review of the preclinical studies, JAMA 286: 2441-2449). It is believed that treatment costs for siRNA would be similar to most protein-based therapies, e.g., antibody therapies. Preclinical cancer studies have shown inhibition of growth and survival of tumor cells by RNAi-mediated downregulation of several key oncogenes or tumor-promoting genes, including growth and angiogenic factors or their receptors (vascular endothelial growth factor, epidermal growth factor receptor), human telomerase (hTR, hTERT), viral oncogenes (papillomavirus E6 and E7) or translocated oncogenes (BCR-abl).

Various studies report on the in vivo activity and the potential of RNAi agents to suppress tumor growth. These include an intratumoral injection of an shRNA-adenoviral vector construct targeting a cell-cycle regulator causing inhibition of subcutaneous small cell lung tumor in mice, and systemic administration of an siRNA targeting a carcinoembryonic antigen-related cell adhesion molecule (CEACAM6) in mice with subcutaneously xenografted pancreatic adenocarcinoma cells. In another report, direct injection of a plasmid vector expressing shRNAs to matrix metalloproteinase MMP-9 and a cathepsin showed efficacy in established glioblastoma (Chen, et al., 2005, Reversal of the phenotype by K-rasvall2 silencing mediated by adenovirus-delivered siRNA in human pancreatic cancer cell line Panc-1, World J. Gastroenterol. 11(6): 831-838). However, delivery of siRNA for long-term expression in target cells and tissues has been particularly difficult in vivo.

Another problem in gene transfer is the delivery of therapeutic molecules to a sufficient number of target cells to elicit a therapeutic response. Recently, a series of virus-encoded and other regulatory proteins were found to possess the ability to cross biological membranes. These proteins include HIV-Tat and the herpes simplex virus type 1 tegument protein VP22. VP22 was also reported to exhibit a unique property of effecting intercellular spread. VP22 is a basic, 38-kDa phosphorylated protein (Knopf, et al., 1980, J. Gen. Virol. 46:405-414) encoded by the viral UL49 gene (Elliott, et al., 1992, J. Gen. Virol. 73:723-726).

Specific and controlled delivery of therapeutic molecules to an affected cell population, e.g., to tumor cells and even circulating cancer cells, can potentially be achieved by strategically positioning nucleic acid and protein regulatory elements, e.g., cell and tissue-specific promoters and enzyme cleavage sites. These elements are recognized by the production machinery that is present only in certain cell types. The ability to easily combine and regulate the expression and delivery of multiple therapeutic molecules, while taking effective safety measures without compromising expression levels, in methods for using a lentiviral gene transfer vector or lentiviral transfer system, would provide a researcher with a critical tool for treating a broad range of diseases and disorders.

SUMMARY OF THE INVENTION

The present invention is related to lentiviral transfer systems including safe, self-inactivating, recombinant lentiviral vectors with the capacity to accommodate strategic combinations of genes for therapeutic molecules and novel regulatory sequences, in methods for treating a broad range of diseases and disorders.

In one aspect, the invention relates to a lentiviral gene transfer system comprising: a self-inactivating transfer vector comprising: a first gene unit with a first heterologous nucleic acid sequence, operably linked to a first regulatory nucleic acid sequence; and a second gene unit with a second heterologous nucleic acid sequence, operably linked to a second regulatory nucleic acid sequence; and a helper construct which lacks a 5' LTR, wherein said 5' LTR has been replaced with a heterologous promoter, said helper construct further comprising: a lentiviral env nucleic acid sequence containing a deletion, wherein said deleted env nucleic acid sequence does not produce a functional env protein; a packaging signal containing a deletion, wherein said deleted packaging signal is nonfunctional. The transfer vector may be preferably derived from HIV-1. Preferably, RNAi or a polypeptide may be encoded by the heterologous nucleic acid sequence. In addition, expression of the first and second heterologous nucleic acid sequences may have a synergistic effect in inhibiting progression of a disease or disorder.

The transfer vector may include mammalian insulator sequence and splice acceptor and splice donor sites, and may be free of wPRE "wood-chuck" hepatitis virus post-transcriptional element downstream of a cloning site (Gao et al., J. Virol., Mar. 2008; p. 2938-2951).

The RNAi may inhibit expression of a gene that contributes to progression of a disease or disorder. In addition, the first or second heterologous nucleic acid sequence may include a sequence encoding a trafficking signal, and the trafficking signal may be expressed as a fusion with a protein expressed from the second heterologus nucleic acid sequence. The intercellular trafficking signal may be a membrane-penetrating protein or a fragment thereof, such as a plant or bacterial protein toxin, or viral protein, any other sequence domain with transporting function between cells, in particular, cancer cells. The trafficking signal may be derived from herpesvirus VP22 or HIV-Tat, or may be a HIV-Tat eleven amino acid transduction sequence. The herpesvirus may be HSV1, and the trafficking signal may further be a VP22 protein homologue of HSV1 VP22. The VP22 transport signal may include a C-terminal 34 amino acid sequence of VP22 of HSV1, or a fragment having 80% or greater identity to the terminal 34 amino acid sequence of VP22 of HSV1. Further, the VP22 transport signal may include one or more of RSASR, RTASR, RSRAR, RTRAR, ATATR, or RSAASR.

The transfer vector may utilize general or cell or tissue specific promoters such as TSTA promoter, mesothelin promoter, hPSA promoter, hCCKAR promoter, hAFP promoter, and hNSE promoter.

Tissue-specific enzyme cleavage sites may be included in the transfer vector, wherein cleavage at the site occurs within a polypeptide that is encoded by the first and second heterologous nucleic acid sequences. The regulatory nucleic acid sequence may include a sequence encoding a cell or tissue-specific enzyme cleavage site, wherein cleavage at the site occurs within at least one polypeptide that is encoded by two or more of the first, second and third heterologous nucleic acid sequences. The cell or tissue-specific enzyme cleavage site may be a protease 2A cleavage site, a presecretory protein signal peptidase cleavage site, or a pancreatic prechymotrypsinogen cleavage site.

The transfer vector may also include a nucleic acid sequence encoding translation initiation site. Such a sequence may be positioned between the gene units, and in certain aspects may be considered to belong to a "regulatory sequence" of a gene unit. Although a variety of sequences may be used, an internal ribosome entry site (IRES) is preferred.

The inventive lentiviral transfer system may be used to prepare a treatment for a disease or disorder. The disease or disorder may be cancer. In a preferred embodiment, a heterologous nucleic acid sequence may encode the P53 protein.

The antisense RNA, RNAi, or any polypeptide expressed from the heterologous nucleic acid sequence may be expressed consistently and for long period of time to inhibit expression of a gene or the activity of a gene product that contributes to progression of the cancer. The antisense RNA, RNAi and the polypeptide may inhibit expression and activity of a tumor promoting gene or gene product. The RNAi and the expressed polypeptide may inhibit expression of or activity of a growth factor, growth factor receptor, angiogenic factor, angiogenic factor receptor, cell cycle regulator, apoptosis-inducing molecule, or cell adhesion molecule. The RNAi or the expressed polypeptide may inhibit the expression or activity of a vascular endothelial growth factor, Bcl-2, K-ras, AEC-1, Myc, including c-Myc, a vascular endothelial growth factor receptor, epidermal growth factor receptor, hTR, hTERT, papillomavirus E6, papillomavirus E7, BCR-abl, CEACAM6, MMP9, or a cathepsin.

The cancer to be treated may be prostate cancer in which a regulatory nucleic acid sequence may include hPSA. If the cancer is liver cancer then a regulatory nucleic acid sequence may include hAFP. If the cancer is pancreatic cancer then a regulatory nucleic acid sequence may include hCCKAR to control the expression of RNAi or a polypeptide.

The inventive lentiviral transfer system may be used to prepare a treatment for a genetic disorder, such as a metabolic disorder, including Gaucher's Disease or Fabry's Disease. In the case of Gaucher's Disease, a first heterologous nucleic acid sequence may encode glucocerebrosidase and a second heterologous nucleic acid sequence may encode a human intrinsic selectable marker such as huCD25 protein or huNGF protein.

The lentiviral transfer system may include a regulatory nucleic acid sequence that includes a sequence encoding a trafficking signal that is expressed as a fusion with a glucocerebrosidase protein expressed from an adjacent heterologous nucleic acid sequence. A second regulatory nucleic acid sequence may include translation initiation sequence as well. A cell or tissue-specific enzyme cleavage site may also be included.

In the case of Fabry's Disease, said first heterologous nucleic acid sequence may encode an alpha-galactosidase-A protein, and a second heterologous nucleic acid sequence may encode the huCD25 protein.

In another aspect, the inventive lentiviral transfer system may include a first heterologous nucleic acid sequence comprising a sequence encoding a trafficking signal that is expressed as a fusion with the alpha-galactosidase-A protein expressed from the first heterologous nucleic acid sequence. The trafficking signal may be a VP22 trafficking signal or an HIV-Tat trafficking signal.

In yet another aspect, if the genetic disorder is Leber Congenital Amaurosis, the first heterologous nucleic acid sequence may encode the RPE65 protein, and a second heterologous nucleic acid sequence may encode the hBDNF protein, and a second regulatory nucleic acid sequence may include hNSE, and further the vector may include a third heterologous nucleic acid sequence encoding the hNGF protein, and also a third regulatory nucleic acid sequence including a sequence encoding a cell or tissue-specific enzyme cleavage site.

In another aspect, the disease or disorder to be treated may be a neurological disorder, such as Alzheimer's Disease, in which case, a first heterologous nucleic acid may encode the hNGF protein, a second heterologous nucleic acid may encode an RNAi targeted to beta-amyloid precursor protein, and wherein the second regulatory nucleic acid sequence may include a sequence encoding a cell or tissue-specific enzyme cleavage site. A third third heterologous nucleic acid that encodes the hBDNF protein may also be included, in which the first regulatory nucleic acid sequence may include a sequence encoding a trafficking signal that is expressed as a fusion with the hNGF protein expressed from the first heterologous nucleic acid sequence.

If the neurological disorder is Parkinson's Disease, a first heterologous nucleic acid may encode the hBDNF protein or the hGDNF protein, and the second heterologous nucleic acid encodes hGAD. The second regulatory nucleic acid sequence may include a sequence encoding a cell or tissue-specific enzyme cleavage site. Further, the first regulatory nucleic acid may include a sequence encoding a trafficking signal that is expressed as a fusion with the hBDNF protein or hGDNF protein expressed from the first heterologous nucleic acid sequence, wherein the vector may further include a third heterologous nucleic acid sequence encoding hNGF, in which the vector may further include a third regulatory nucleic acid sequence encoding a cell or tissue-specific enzyme cleavage site.

In another aspect, the invention is directed to a method for treating a condition, comprising administering to a patient a lentiviral particle for gene transfer, said lentiviral particle produced using a lentiviral transfer system comprising: a self-inactivating transfer vector comprising: a first gene unit with a first heterologous nucleic acid sequence, operably linked to a first regulatory nucleic acid sequence; and a second gene unit with a second heterologous nucleic acid sequence, operably linked to a second regulatory nucleic acid sequence; and a helper construct which lacks a 5' LTR, wherein said 5' LTR has been replaced with a heterologous promoter, said helper construct further comprising: a lentiviral env nucleic acid sequence containing a deletion, wherein said deleted env nucleic acid sequence does not produce functional env protein; a packaging signal containing a deletion, wherein said deleted packaging signal is nonfunctional. The condition may be cancer, such as liver cancer, pancreatic cancer, or prostate cancer. The condition may also be a genetic disorder, such as Gaucher's Disease or Fabry's Disease. The condition may also be a neurological disorder, such as Parkinson's Disease or Alzheimer's Disease. The condition may also be a need for cosmetic enhancement.

A pharmaceutical composition comprising a lentiviral particle for gene transfer, said lentiviral particle produced using a lentiviral transfer system comprising: a self-inactivating transfer vector comprising: a first gene unit with a first heterologous nucleic acid sequence, operably linked to a first regulatory nucleic acid sequence; and a second gene unit with a second heterologous nucleic acid sequence, operably linked to a second regulatory nucleic acid sequence; and a helper construct which lacks a 5' LTR, wherein said 5' LTR has been replaced with a heterologous promoter, said helper construct further comprising: a lentiviral env nucleic acid sequence containing a deletion, wherein said deleted env nucleic acid sequence does not produce functional env protein; a packaging signal containing a deletion, wherein said deleted packaging signal is nonfunctional.

In a further aspect, the invention is directed to a pharmaceutical composition that includes a lentiviral transfer vector, said lentiviral transfer vector comprising a first heterologous nucleic acid sequence, operably linked to a first regulatory nucleic acid sequence; and a second heterologous nucleic acid sequence, operably linked to a second regulatory nucleic acid sequence, wherein said transfer vector is self-inactivating.

The pharmaceutical compositions as described above may further include a chemotherapeutic agent, a steroid agent such as prednisolone, cortisone, corticosterone, or dexamethasone.

In one aspect of the invention, SIN element is incorporated into the recombinant lentivirus; the tat region has been modified so as to optionally allow for infection efficiency without allowing the replication functions and uncontrolled infection of the recombinant lentivirus beyond the intended target; and the rev protein has been inactivated so as to prevent further unwanted infectivity while preserving the basic function of the rev to support the expression efficiency of the therapeutic gene(s). Tat and rev proteins may be inactivated of their original replication activity without necessarily removing them from the lentivirus and thereby preserve their desirable attributes while keeping the resulting vector bio-safe.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIG. 1A. Helper (packaging) construct. The 5' LTR of the helper construct is replaced with the CMV promoter, to avoid integration of the viral elements presented in that construct. This is an important biosafety feature of the lentiviral transfer system of the invention. The triangles represent deletions: one represents a 36-bp deletion harboring the putative packaging signal from nucleotides 753 to 789 between the 5' major splice donor site and the beginning of the gag ATG coding region; one represents a deletion in the tat gene, and a third represents a deletion in nef. The packaging signal is functionally absent from this construct, to avoid production of an active gag-pol precursor. The poly (A) site was derived from the bovine growth hormone gene. The helper construct provides a nucleic acid sequence encoding lentiviral gag and pol, operably linked to a heterologous regulatory nucleic acid sequence. The construct further contains a deleted, nonfunctional env protein and is devoid of lentiviral sequences both upstream and downstream from a splice donor site to a lentiviral gag initation site. FIG. 1B. Envelope expression construct. An envelope construct encoding vesicular stomatitis virus G glycoprotein (VSV-G) is shown, though other non-lentiviral envelope proteins can be used instead. Expression is driven by the HIV-1 LTR. The poly (A) site was derived from the simian virus 40 late region. FIG. 1C. Transfer vector constructs. In these constructs, Tat, Vpr, and Nef are inactivated. Boxes interrupted by jagged lines contain partial deletions. RRE=Rev-response element; ψ=cis-acting packaging signal; IRES=internal ribosome entry site; huCD25=human IL-2Ra chain gene; GFP=Green Fluorescent Protein coding sequence; RNAi=interfering RNA coding sequence; S=stop codon; T=termination signal (e.g., SV40 polyA or BGH polyA); CS=cleavage site (e.g., viral 2A-like peptide cleaved by the 2A protease, presecretory protein cleavage site, pancreatic prechymotrypsinogen cleavage site); hPSA=human prostate specific antigen promoter; P1=promoter 1; CMV, Human CMV-IE promoter; P2=promoter-2; P53=tumor suppressor gene; dsRNA=Bcl-2 RNAi (human).

FIG. 2 Heterologous Proteins. This table provides examples of heterologous proteins contemplated for use in the vectors and methods of the present invention.

FIG. 3 Transport Genes. This table provides examples of transport genes contemplated for use in developing transport sequences for the vectors and methods of the present invention.

FIG. 4 Promoter Elements. This table provides examples of promoter elements contemplated for use in the vectors and methods of the present invention.

FIG. 5 Enhancer Elements. This table provides examples of enhancer elements contemplated for use in the vectors and methods of the present invention.

FIG. 7 Therapeutic Constructs. This table provides examples of constructs for use in the vectors and methods of the invention for certain therapeutic applications.

FIG. 8A. EGFP expression in PC-3 cells infected with STN-HIV-p53-TRES-EGFP (Panel 1) and PC-3 cells not infected with virus (2). FIG. 8B. EGFP expression in 293T cells infected with SIN-HIV-p53-TRES-EGFP (Panel 1) and 293T cells not infected with virus (2). FIG. 8C. Viral packaging of Vector. FIG. 8D. P53 expression. Lane 1: Size standards 1 kb plus DNA Ladder. Lane 2: PC-3 cells (no infection). Lane 3: PC-3 cells (infection). Lane 4: Blank. Lane 5: 293T cells (no infection). Lane 6: 293T cells (infection).

FIG. 9 Therapeutic Constructs 2. This table provides examples of constructs for use in the vectors and methods of the invention for certain therapeutic applications.

FIGS. 10A and 10B show phenotype of in vitro cell culture under phase-contrast microscope indicating that the P53-Bcl-2 RNAi construct induces cell necrosis in PC3 prostate cancer cells. FIG. 10A. untreated living cells. FIG. 10B. treated with viral vector construct P53-Bcl-2 RNAi, expressing P53 and an RNAi agent targeting human Bcl-2.

FIGS. 11A and 11B show phenotype of in vitro cell culture under phase-contrast microscope indicating that the P53-Bcl-2 RNAi construct does not cause necrosis in 293T cells. FIG. 11A. untreated cells. FIG. 11B. treated with viral vector construct P53-Bcl-2 RNAi, expressing P53 and an RNAi agent targeting human Bcl-2.

FIG. 13A. control tumor expresses hPSA. FIG. 13B. treatment tumor shows cell necrosis and no expression of hPSA.

FIGS. 14A-14C show a table that shows results from another mouse (in vivo) study confirming tumor reduction findings. Group V1 is prostrate tumor mice treated with P53 expressed alone in a viral vector; Group V2 is tumor mice treated with BCL2 siRNA alone expressed through viral vector; V3 is tumor mice treated with the dual viral construct expressing P53 and BCL2 siRNA. Group PC shows untreated tumor mice control. "*" in the tables indicates tumor sizes on Day 7 as the starting sizes for calculating the tumor growth rate and the ratio of Tumor Weigh/Starting Tumor Size for groups of V1, V2, V3, and PC.

DETAILED DESCRIPTION OF THE PREFERRED EMBODIMENTS

Figure 1A:
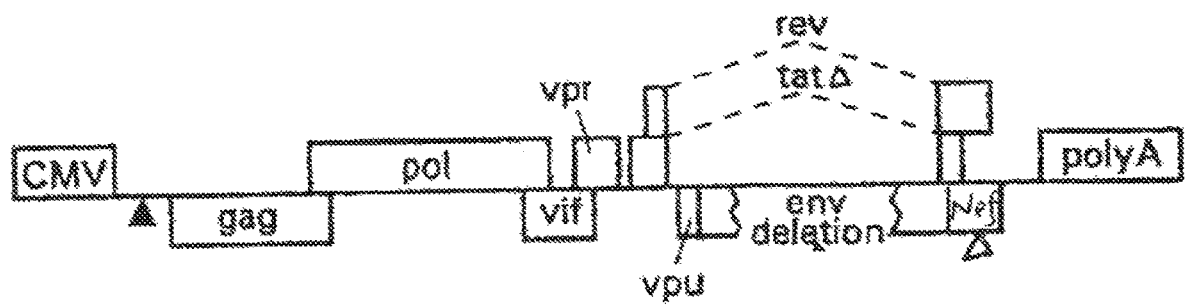
FIGS. 1A-1C Lentiviral transfer system. The drawing shows an HIV-1-based gene transfer system carrying multiple functional (therapeutic) genes.

In the present application, "a" and "an" are used to refer to both single and a plurality of objects.

Unless otherwise indicated, all terms used herein have the same ordinary meaning as they would to one skilled in the art of the present invention.

Citation of documents herein is not intended as an admission that any of the documents cited herein is pertinent prior art, or an admission that the cited documents are considered material to the patentability of the claims of the present application. All statements as to the date or representations as to the contents of these documents are based on the information available to the applicant and do not constitute any admission as to the correctness of the dates or contents of these documents.

As used herein, reference to "upstream", "downstream", "first gene", "second gene", "last gene", "before", "after" and so forth in relation to the spatial positioning of the various DNA sequences in a vector, is meant to be with respect to the 5' to 3' orientation of the vector sequence. For example "before" will have the same meaning as "upstream of" or 5' of a particular reference position, and "after" will have the same meaning of "downstream of" or 3' with respect to a particular reference point on the vector.

As used herein, "gene unit" includes a regulatory region that may include a promoter and a heterologous nucleic acid sequence encoding either an antisense RNA, RNAi or polypeptide of interest that is controlled by the regulatory sequence, which is typically referred to in the context of a multigene transfer vector. However, in situations where a fused polypeptide is desirous of being generated from the multigene vector of the encoded polypeptides of adjacent gene units, the regulatory region of the downstream gene units may include a nucleic acid sequence encoding a cleavage site instead of a separate promoter.

MODES OF CARRYING OUT THE INVENTION

It is to be understood that this invention is not limited to particular formulations or process parameters, as these may, of course, vary. It is also to be understood that the terminology used herein is for the purpose of describing particular embodiments of the invention only, and is not intended to be limiting. Further, it is understood that a number of methods and materials similar or equivalent to those described herein can be used in the practice of the present invention.

I. Lentiviral Transfer System

The present invention provides a recombinant lentivirus capable of infecting dividing and non-dividing cells. The virus is useful for the in vivo and ex vivo transfer and expression of nucleic acid sequences. Lentiviral vectors of the invention may be lentiviral transfer plasmids or infectious lentiviral particles. Construction of lentiviral vectors, helper constructs, envelope constructs, etc., for use in lentiviral transfer systems has been described, e.g., in U.S. Patent App. Pub. No. 2003/0119770, "Intercellular delivery of a herpes simplex virus VP22 fusion protein from cells infected with lentiviral vectors," incorporated herein by reference in its entirety.

Lentiviruses

Lentiviruses are RNA viruses wherein the viral genome is RNA. When a host cell is infected with a lentivirus, the genomic RNA is reverse transcribed into a DNA intermediate which is integrated very efficiently into the chromosomal DNA of infected cells. This integrated DNA intermediate is referred to as a provirus. Transcription of the provirus and assembly into infectious virus occurs in the presence of an appropriate helper virus or in a cell line containing appropriate sequences enabling encapsidation without coincident production of a contaminating helper virus. As described below, a helper virus is not required for the production of the recombinant lentivirus of the present invention, since the sequences for encapsidation are provided by co-transfection with appropriate vectors.

The lentiviral genome and the proviral DNA have three genes: the gag, the pol, and the env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication. Lentiviruses have additional genes including vit, vpr, tat, rev, vpu, nef, and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site, ψ). If the sequences necessary for encapsidation (or packaging of lentiviral RNA into infectious virions) are missing from the viral genome, the result is a cis defect which prevents encapsidation of genomic RNA. The resulting mutant is still capable of directing the synthesis of all virion proteins, but lacks function of replication.

In a first embodiment, the invention provides a recombinant lentivirus capable of infecting a dividing or non-dividing cell. The recombinant lentivirus comprises a nucleic acid sequence containing a lentiviral packaging signal flanked by lentiviral cis-acting nucleic acid sequences necessary for reverse transcription and integration, a heterologous nucleic acid sequence operably linked to a regulatory nucleic acid sequence, and a nucleic acid sequence encoding an intercellular trafficking signal, where the nucleic acid sequence encoding the intercellular trafficking signal is fused in-frame with the heterologous nucleic acid sequence, where the lentivirus does not contain either a complete gag, pol, tat, rev, or env gene.

The recombinant lentivirus of the invention is therefore genetically modified in such a way that some of the structural, infectious genes of the native virus have been removed, and some removed sequences replaced with a nucleic acid sequence to be delivered to a target non-dividing cell. After infection of a cell by the virus, the virus releases its nucleic acid into the cell and the lentivirus genetic material can integrate into the host cell genome. The transferred lentivirus genetic material is then transcribed and translated, e.g., as dictated by the regulatory sequences, into proteins within the host cell.

Lentiviral Vector Systems

The invention provides a method of producing a recombinant lentivirus capable of infecting a dividing or non-dividing cell comprising transfecting a suitable host cell with the following: a transfer vector providing a nucleic acid encoding a lentiviral gag and a lentiviral pol, where the gag and pol nucleic acid sequences are operably linked to a heterologous regulatory nucleic acid sequence and where the transfer vector is defective for nucleic acid sequence encoding functional env protein and devoid of lentiviral sequences both upstream and downstream from a splice donor site to a gag initiation site of a lentiviral genome; an envelope construct providing a nucleic acid encoding a non-lentiviral env protein; and a helper construct providing a nucleic acid sequence containing a lentiviral packaging signal flanked by lentiviral cis-acting nucleic acid sequences for reverse transcription and integration, and providing a cloning site for introduction of a heterologous nucleic acid sequence operably linked to a regulatory nucleic acid sequence and optionally to a nucleic acid sequence encoding an intercellular trafficking signal, where the nucleic acid sequence encoding the intercellular trafficking signal is fused in-frame with the heterologous nucleic acid sequence, where the helper construct does not contain either a complete gag, pol, or env gene, and recovering the recombinant lentivirus. An illustration of the individual vectors used in the method of the invention is shown in FIG. 1.

The method of the invention includes the combination of a minimum of three vectors in order to produce a recombinant virion or recombinant lentivirus. For example, a vector of the invention can include (a) the p53 gene product, expressed and driven by a regulatory nucleic acid sequence to treat tumor cells or migrating cells having a p53 gene mutation; (b) a specific siRNA driven by second regulatory nucleic acid sequence to down-regulate tumor activity of the tumor cells in target tissue or organs; wherein the double or multiple gene system is able to enhance delivery efficacy and therapeutic response. It is understood that in the vectors and methods of the present invention, the relative positions in the transfer vector of the therapeutic molecules—be they proteins, RNAi or other types of antisense agents—can vary as needed. Therefore, for example, any of the first, second, or third heterologous nucleic acid sequences can encode an RNAi. Furthermore, multiple heterologous nucleic acid sequences (e.g., two or three) can encode an RNAi or other antisense agent.

A first vector is a helper construct, which provides a nucleic acid encoding a lentiviral gag and a lentiviral pol (FIG. 1A).

Figure 1B:
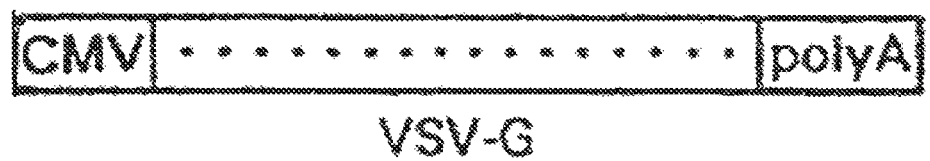

A second vector is an envelope construct, which provides a nucleic acid encoding a non-lentiviral env protein (FIG. 1B). The env gene can be derived from any virus excluding lentiviruses. The env gene is ideally derived from a virus other than HIV. The env gene may be amphotropic envelope protein which allows transduction of cells of human and other species, or may be ecotropic envelope protein, which is able to transduce only mouse and rat cells. Further, it may be desirable to target the recombinant virus by linkage of the envelope protein with an antibody or a particular ligand for targeting to a receptor of a particular cell-type. By inserting a sequence (including regulatory region) of interest into the viral vector, along with another gene which encodes the ligand for a receptor on a specific target cell, for example, the vector is now target specific. Lentiviral vectors can be made target specific by inserting, for example, a protein. Targeting is often accomplished by using an antibody to target the lentiviral vector. Those of skill in the art will know of, or can readily ascertain without undue experimentation, specific methods to achieve delivery of a lentiviral vector to a specific target.

Examples of retroviral-derived env genes include, but are not limited to: Moloney murine leukemia virus (MoMuLV), Harvey murine sarcoma virus (HaMuSV), murine mammary tumor virus (MuMTV), gibbon ape leukemia virus (GaLV), and Rous Sarcoma Virus (RSV). Other env genes such as Vesicular stomatitis virus (VSV) (Protein G) can also be used.

The construct providing the viral env nucleic acid sequence is operably associated with regulatory sequence, e.g., a promoter or enhancer. Preferably, the regulatory sequence is a viral promoter. The regulatory sequence can be any eukaryotic promoter or enhancer, including for example, the Moloney murine leukemia virus promoter-enhancer element, the human cytomegalovirus enhancer, or the vaccinia P7.5 promoter. In some cases, such as the HIV-1 promoter-enhancer element, these promoter-enhancer elements are located within or adjacent to the LTR sequences.

Figure 1C:
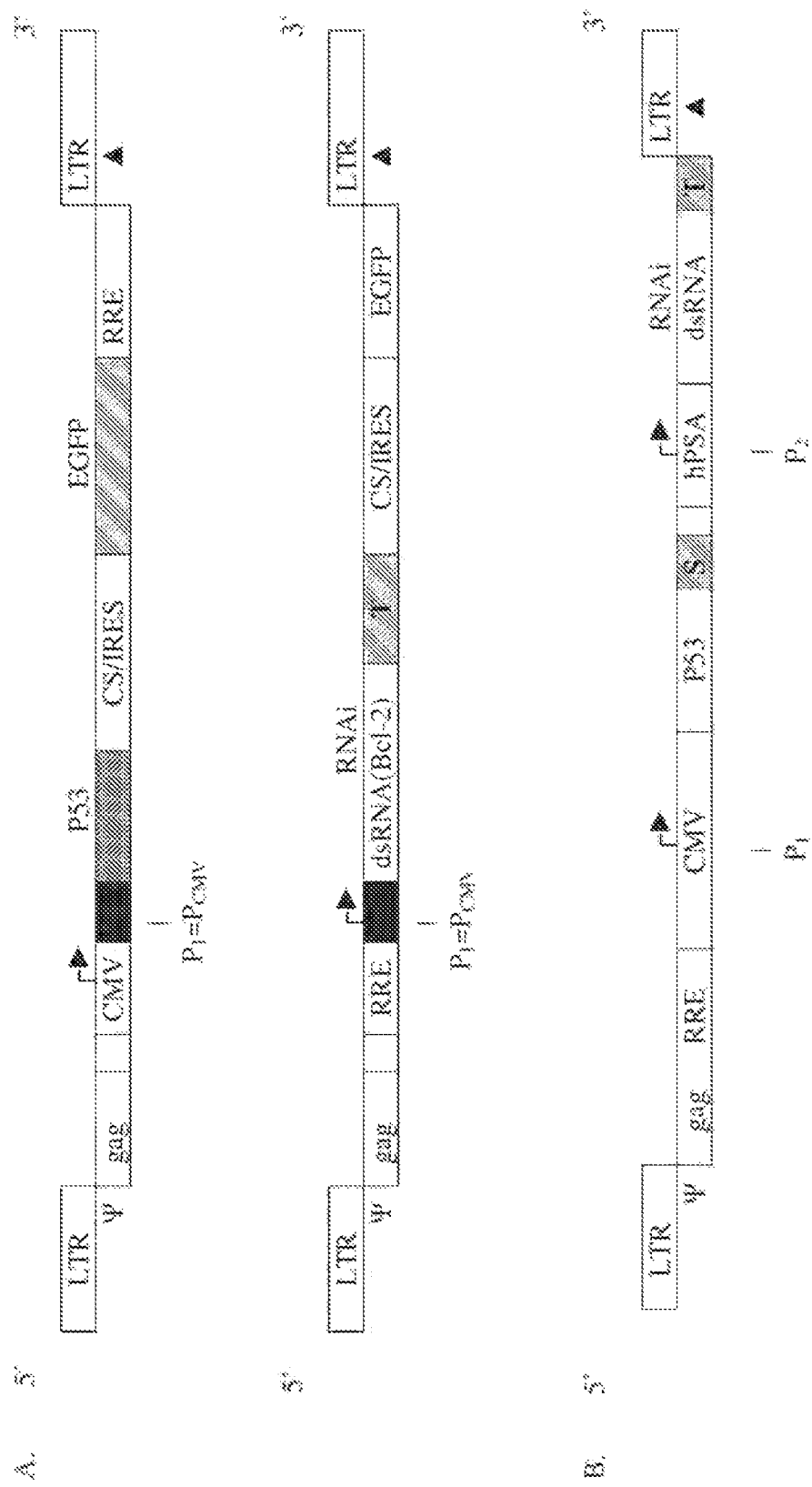
Figure 1C:
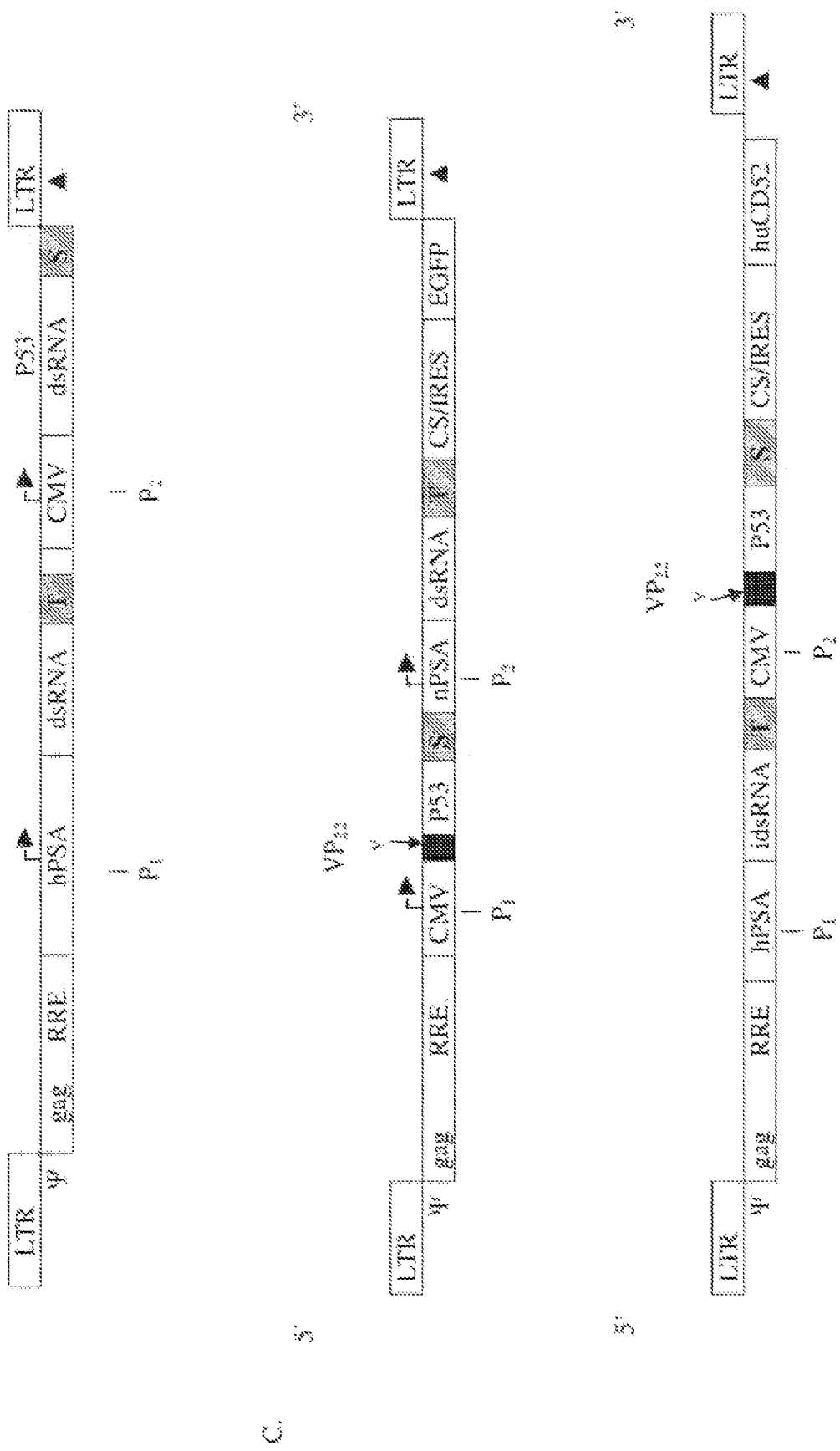
Figure 1C:
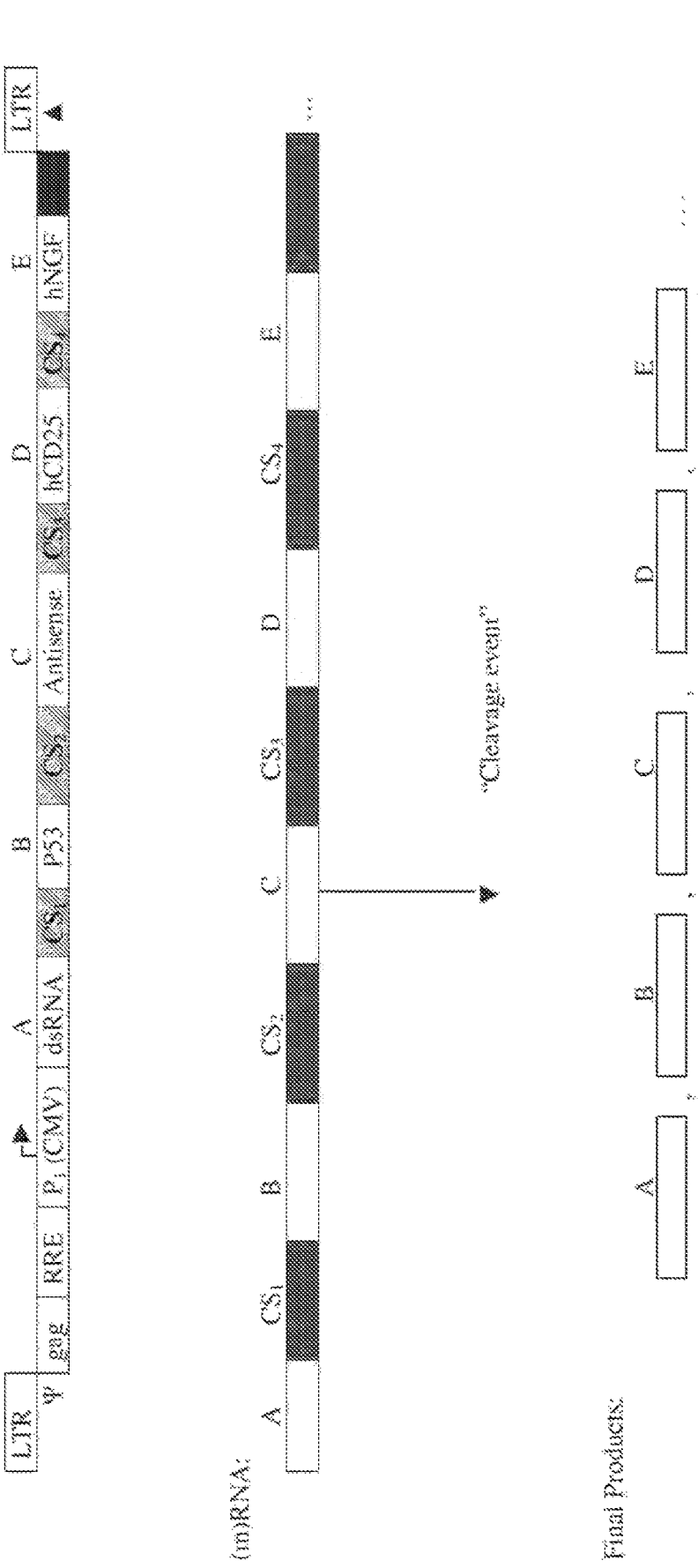

A third vector, the transfer vector, provides a nucleic acid sequence, which contains the cis-acting viral sequences necessary for the lentiviral life cycle. Such sequences include the lentiviral psi packaging sequence, reverse transcription signals, integration signals, viral promoter, enhancer, and polyadenylation sequences. The transfer vector also contains a cloning site for a heterologous nucleic acid sequence to be transferred to a dividing or non-dividing cell, and optionally a nucleic acid sequence encoding an intercellular trafficking signal, where the nucleic acid sequence encoding the intercellular trafficking signal is fused in-frame with the heterologous nucleic acid sequence (FIG. 1C).

Since recombinant lentiviruses produced by standard methods in the art are defective, they require assistance in order to produce infectious vector particles. Typically, this assistance is provided, for example, by using a helper cell line that provides the missing viral functions. These plasmids are missing a nucleotide sequence which enables the packaging mechanism to recognize an RNA transcript for encapsidation. Suitable cell lines produce empty virions, since no genome is packaged. If a lentiviral vector is introduced into such cells in which the packaging signal is intact, but the structural genes are replaced by other genes of interest, the vector can be packaged and vector virion produced.

The method of producing the recombinant lentivirus of the invention is different than the standard helper virus/packaging cell line method described above. The three or more individual vectors used to co-transfect a suitable packaging cell line collectively contain all of the required genes for production of a recombinant virus for infection and transfer of nucleic acid to a non-dividing cell. Consequently, there is no need for a helper virus.

Conveniently during the cloning stage, the nucleic acid construct referred to as the transfer vector, having the packaging signal and the heterologous cloning site, also contains a selectable marker gene. Marker genes are utilized to assay for the presence of the vector, and thus, to confirm infection and integration. Typical selection genes encode proteins that confer resistance to antibiotics and other toxic substances, e.g. histidinol, puromycin, hygromycin, neomycin, methotrexate, etc.

"Non-dividing" cell refers to a cell that does not go through mitosis. Non-dividing cells may be blocked at any point in the cell cycle, (e.g., $G_0/G_1$, $G_1/S$, $G_2/M$), as long as the cell is not actively dividing. For ex vivo infection, a dividing cell can be treated to block cell division by standard techniques used by those of skill in the art, including, irradiation, aphidocolin treatment, serum starvation, and contact inhibition. However, it should be understood that ex vivo infection is often performed without blocking the cells since many cells are already arrested (e.g., stem cells). The recombinant lentivirus vector of the invention is capable of infecting any non-dividing cell, regardless of the mechanism used to block cell division or the point in the cell cycle at which the cell is blocked. Examples of pre-existing non-dividing cells in the body include neuronal, muscle, liver, skin, heart, lung, and bone marrow cells, and their derivatives.

The method of the invention provides at least three vectors which provide all of the functions required for packaging of recombinant virions as discussed above. The method also envisions transfection of vectors including viral genes such as vpr, vif, nef, vpx, tat, rev, and vpu. Some or all of these genes can be included, for example, on the packaging construct vector, or, alternatively, they may reside on individual vectors. There is no limitation to the number of vectors which are utilized, as long as they are co-transfected to the packaging cell line in order to produce a single recombinant lentivirus. For example, one could put the env nucleic acid sequence on the same construct as the gag and pol.

The vectors are introduced via transfection or infection into the packaging cell line. The packaging cell line produces viral particles that contain the vector genome. Methods for transfection or infection are well known by those of skill in the art. After co-transfection of the at least three vectors to the packaging cell line, the recombinant virus is recovered from the culture media and titered by standard methods used by those of skill in the art.

In another embodiment, the invention provides a recombinant lentivirus produced by the method of the invention as described above.

The invention also provides a method of nucleic acid transfer to a non-dividing cell to provide expression of a particular nucleic acid sequence. Therefore, in another embodiment, the invention provides a method for introduction and expression of a heterologous nucleic acid sequence in a non-dividing cell comprising infecting the non-dividing cell with the recombinant virus of the invention and expressing the heterologous nucleic acid sequence in the non-dividing cell.

It may be desirable to modulate the expression of a gene regulating molecule in a cell by the introduction of a molecule by the method of the invention. The term "modulate" envisions the suppression of expression of a gene when it is over-expressed, or augmentation of expression when it is under-expressed. Where a cell proliferative disorder is associated with the expression of a gene, nucleic acid sequences that interfere with the gene's expression at the translational level can be used. This approach utilizes, for example, antisense nucleic acid, ribozymes, or triplex agents, siRNA to block transcription or translation of a specific mRNA, either by masking that mRNA with an antisense nucleic acid or triplex agent, or by cleaving it with a ribozyme.

The method of the invention may also be useful for neuronal or glial cell transplantation, or "grafting," which involves transplantation of cells infected with the recombinant lentivirus of the invention ex vivo, or infection in vivo into the central nervous system or into the ventricular cavities or subdurally onto the surface of a host brain. Such methods for grafting will be known to those skilled in the art and are described in Neural Grafting in the Mammalian CNS, Bjorklund and Stenevi, eds. (1985). Procedures include intraparenchymal transplantation, (i.e., within the host brain) achieved by injection or deposition of tissue within the host brain so as to be apposed to the brain parenchyma at the time of transplantation.

Self-Inactivating Lentiviral Vectors

Self-inactivating (SIN) lentiviral vectors have a deletion in the U3 region of the 3' LTR that eliminates regulatory sequences, including the TATA box. The deletion has been reported to result in transcriptional inactivation of the LTR in proviruses without affecting vector titers or transgene expression in vitro. SIN vectors are described, e.g., by Zufferey, et al., 1998, J. Virology 72(12):9873-9880, who made a 400 bp deletion, and Miyoshi, et al., 1998, J. Virology 72(10):81508157, who made a 133 bp deletion.

It has been reported that a certain U3 deletion actually results in increased expression from the vector in vivo (Bayer, et al., 2008, A Large U3 Deletion Causes Increased In Vivo Expression from a Nonintegrating Lentiviral Vector, Molecular Therapy doi:10.1038/mt.2008.199). This finding suggests that additional alterations to the lentivirus sequences are needed to ensure safety of gene transfer systems.

II. Heterologous Nucleic Acid Sequences

A heterologous nucleic acid sequence is operably linked to a regulatory nucleic acid sequence. As used herein, the term "heterologous" nucleic acid sequence refers to a sequence that originates from a foreign species, or, if from the same species, it may be substantially modified from its original form. Alternatively, an unchanged nucleic acid sequence that is not normally expressed in a cell is a heterologous nucleic acid sequence. The term "operably linked" refers to functional linkage between the regulatory sequence and the heterologous nucleic acid sequence. The heterologous sequence can be linked to a promoter. The heterologous nucleic acid sequence can be under control of either the viral LTR promoter-enhancer signals or of an internal promoter, and retained signals within the lentiviral LTR can still bring about efficient integration of the vector into the host cell genome. The use of nonintegrating vectors for certain purposes, e.g., where transient expression is sufficient, is also contemplated.

The recombinant virus of the invention is capable of transferring nucleic acid sequences into a non-dividing cell. The term "nucleic acid sequence" refers to any nucleic acid molecule, preferably DNA. The nucleic acid molecule may be derived from a variety of sources, including DNA, cDNA, synthetic DNA, RNA, or combinations thereof. Such nucleic acid sequences may comprise genomic DNA which may or may not include naturally occurring introns. Moreover, such genomic DNA may be obtained in association with promoter regions, introns, or poly(A) sequences. Genomic DNA may be extracted and purified from suitable cells by means well known in the art. Alternatively, messenger RNA (mRNA) can be isolated from cells and used to produce cDNA by reverse transcription or other means.

FIG. 2 shows examples of heterologous proteins that can be expressed from their genes using the vectors and methods of the present invention. FIGS. 7 and 8 further list examples of cloned structural genes that can serve as, e.g., a first, second, or third heterologous nucleic acid sequence of the invention.

A preferred protein for expression using the vectors and methods of the present invention is tumor antigen P53. Expression of P53 is defective in most cancers, e.g., due to mutation of the gene or lowered expression. Delivery of the wild-type gene encoding the 53-kilodalton protein is therefore a goal of gene therapy for many cancers.

Nucleic acids encoding the same proteins or targeting the same RNAs can be used in a single transfer vector, for example, two genes for the same protein can be cloned from different sources and used as the first and second heterologous nucleic acid sequences. Similarly, RNAi sequences that are specific for different parts of the same target RNA, or that differ in their percent homology to the target RNA, can be used together.

It may be desirable to transfer a nucleic acid encoding a biological response modifier. Included in this category are immunopotentiating agents including nucleic acids encoding a number of the cytokines classified as "interleukins." These include, for example, interleukins 1 through 12. Also included in this category, although not necessarily working according to the same mechanisms, are interferons, and in particular gamma interferon (γ-IFN), tumor necrosis factor (TNF) and granulocyte-macrophage-colony stimulating factor (GM-CSF). It may be desirable to deliver such nucleic acids to bone marrow cells or macrophages to treat enzymatic deficiencies or immune defects, or cancer disease. Nucleic acids encoding growth factors, toxic peptides, ligands, receptors, or other physiologically important proteins can also be introduced into specific non-dividing cells.

Selection of RNAi Agents and Other Antisense Nucleic Acid Sequences

An RNAi agent used in the vectors and methods of the present invention can be targeted to any RNA molecule. Besides messenger RNA (mRNA), RNAi agents can target, e.g., various species of microRNA. The use of RNAi in gene therapy and RNAi selection and sequence design, are described, e.g., in WO 2007/109131, "Lentiviral Vectors That Provide Improved Expression and Reduced Variegation after Transgenesis," and WO 2007/087113, "Natural Antisense and Non-Coding RNA Transcripts as Drug Targets," both of which are incorporated herein by reference.

It may be desirable to modulate the expression of a gene regulating molecule in a cell by the introduction of a molecule by the method of the invention. The term "modulate" envisions the suppression of expression of a gene when it is over-expressed, or augmentation of expression when it is under-expressed. Where a cell proliferative disorder is associated with the expression of a gene, nucleic acid sequences that interfere with the gene's expression at the translational level can be used. This approach utilizes, for example, antisense nucleic acid, ribozymes, or triplex agents, siRNA to block transcription or translation of a specific mRNA, either by masking that mRNA with an antisense nucleic acid or triplex agent, or by cleaving it with a ribozyme.

Antisense nucleic acids are DNA or RNA molecules that are complementary to at least a portion of a specific mRNA molecule (Weintraub, 1990 Scientific American 262:40). In the cell, the antisense nucleic acids hybridize to the corresponding mRNA, forming a double-stranded molecule. The antisense nucleic acids interfere with the translation of the mRNA, since the cell will not translate an mRNA that is double-stranded. Antisense oligomers of about 15 nucleotides are preferred, since they are easily synthesized and are less likely to cause problems than larger molecules when introduced into the target cell. The use of antisense methods to inhibit the in vitro translation of genes is well known in the art (Marcus-Sakura, 1988 Anal Biochem 172:289).

The antisense nucleic acid can be used to block expression of a mutant protein or a dominantly active gene product, such as amyloid precursor protein that accumulates in Alzheimer's disease. Such methods are also useful for the treatment of Huntington's disease, hereditary Parkinsonism, and other diseases. Antisense nucleic acids are also useful for the inhibition of expression of proteins associated with toxicity.

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al. 1991 Antisense Res and Dev 1:227; Helene, C. 1991 Anticancer Drug Design 6:569).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, 1988 J Amer Med Assn 260:3030). A major advantage of this approach is that, because they are sequence-specific, only mRNAs with particular sequences are inactivated.

RNA interference (RNAi) is mediated by double stranded RNA (dsRNA) molecules that have sequence-specific homology to their target nucleic acid sequences (Caplen, N. J., et al, Proc. Natl. Acad. ScL USA 98:9742-9747 (2001)). Biochemical studies in *Drosophila* cell-free lysates indicate that, in certain embodiments of the present invention, the mediators of RNA-dependent gene silencing are 21-25 nucleotide "small interfering" RNA duplexes (siRNAs). The siRNAs are derived from the processing of dsRNA by an RNase enzyme known as Dicer (Bernstein, E., et al, Nature 409:363-366 (2001)). siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion (Bernstein, E., et al, Nature 409:363-366 (2001); Boutla, A., et al, Curr. Biol. 11:1776-1780 (2001)). Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 0 to about 50 nucleotides (nt). In examples of non-limiting embodiments, siRNAs can comprise about 5 to about 40 nt, about 5 to about 30 nt, about 10 to about 30 nt, about 15 to about 25 nt, or about 20-25 nucleotides.

"RNAi" or "RNAi agent" refers to an at least partly double-stranded RNA having a structure characteristic of molecules that are known in the art to mediate inhibition of gene expression through an RNAi mechanism or an RNA strand comprising at least partially complementary portions that hybridize to one another to form such a structure. When an RNA comprises complementary regions that hybridize with each other, the RNA will be said to self-hybridize. An RNAi agent includes a portion that is substantially complementary to a target gene. An RNAi agent, optionally includes one or more nucleotide analogs or modifications. One of ordinary skill in the art will recognize that RNAi agents that are synthesized in vitro can include ribonucleotides, deoxyribonucleotides, nucleotide analogs, modified nucleotides or backbones, etc., whereas RNAi agents synthesized intracellularly, e.g., encoded by DNA templates, typically consist of RNA, which may be modified following transcription. Of particular interest herein are short RNAi agents, i.e., RNAi agents consisting of one or more strands that hybridize or self-hybridize to form a structure that comprises a duplex portion between about 15-29 nucleotides in length, optionally having one or more mismatched or unpaired nucleotides within the duplex. RNAi agents include short interfering RNAs (siRNAs), short hairpin RNAs (shRNAs), and other RNA species that can be processed intracellularly to produce shRNAs including, but not limited to, RNA species identical to a naturally occurring miRNA precursor or a designed precursor of an miRNA-like RNA.

The term "short, interfering RNA" (siRNA) refers to a nucleic acid that includes a double-stranded portion between about 15-29 nucleotides in length and optionally further comprises a single-stranded overhang (e.g., 1-6 nucleotides in length) on either or both strands. The double-stranded portion is typically between 17-21 nucleotides in length, e.g., 19 nucleotides in length. The overhangs are typically present on the 3' end of each strand, are usually 2 nucleotides long, and are composed of DNA or nucleotide analogs. An siRNA may be formed from two RNA strands that hybridize together, or may alternatively be generated from a longer double-stranded RNA or from a single RNA strand that includes a self-hybridizing portion, such as a short hairpin RNA. One of ordinary skill in the art will appreciate that one or more, mismatches or unpaired nucleotides can be present in the duplex formed by the two siRNA strands. One strand of an siRNA (the "antisense" or "guide" strand) includes a portion that hybridizes with a target nucleic acid, e.g., an mRNA transcript. Typically the antisense strand is perfectly complementary to the target over about 15-29 nucleotides, typically between 17-21 nucleotides, e.g., 19 nucleotides, meaning that the siRNA hybridizes to the target transcript without a single mismatch over this length. However, one of ordinary skill in the art will appreciate that one or more mismatches or unpaired nucleotides may be present in a duplex formed between the siRNA strand and the target transcript.

"Short hairpin RNA" refers to a nucleic acid molecule comprising at least two complementary portions hybridized or capable of hybridizing to form a duplex structure sufficiently long to mediate RNAi (typically between 15-29 nucleotides in length), and at least one single-stranded portion, typically between approximately 1 and 10 nucleotides in length that forms a loop connecting the ends of the two sequences that form the duplex. The structure may further comprise an overhang. The duplex formed by hybridization of self-complementary portions of the shRNA has similar properties to those of siRNAs and, as described below, shRNAs are processed into siRNAs by the conserved cellular RNAi machinery. Thus shRNAs are precursors of siRNAs and are similarly capable of inhibiting expression of a target transcript. As is the case for siRNA, an shRNA includes a portion that hybridizes with a target nucleic acid, e.g., an mRNA transcript and is usually the perfectly complementary to the target over about 15-29 nucleotides, typically between 17-21 nucleotides, e.g., 19 nucleotides. However, one of ordinary skill in the art will appreciate that one or more mismatches or unpaired nucleotides may be present in a duplex formed between the shRNA strand and the target transcript.

An RNAi agent is considered to be "targeted" to a transcript and to the gene that encodes the transcript if (1) the RNAi agent comprises a portion, e.g., a strand, that is at least approximately 80%, approximately 85%, approximately 90%, approximately 91%, approximately 92%, approximately 93%, approximately 94%, approximately 95%, approximately 96%, approximately 97%, approximately 98%, approximately 99%, or approximately 100% complementary to the transcript over a region about 15-29 nucleotides in length, e.g., a region at least approximately 15, approximately 17, approximately 18, or approximately 19 nucleotides in length; and/or (2) the Tm of a duplex formed by a stretch of 15 nucleotides of one strand of the RNAi agent and a 15 nucleotide portion of the transcript, under conditions (excluding temperature) typically found within the cytoplasm or nucleus of mammalian cells and/or in a *Drosophila* lysate as described, e.g., in U.S. Patent App. Pubs. 2002/0086356 and 2004/0229266, is no more than approximately 15° C. lower or no more than approximately 10° C. lower, than the Tm of a duplex that would be formed by the same 15 nucleotides of the RNAi agent and its exact complement; and/or (3) the stability of the transcript is reduced in the presence of the RNAi agent as compared with its absence. An RNAi agent targeted to a transcript is also considered targeted to the gene that encodes and directs synthesis of the transcript. A "target region" is a region of a target transcript that hybridizes with an antisense strand of an RNAi agent. A "target transcript" is any RNA that is a target for inhibition by RNA interference. The terms "target RNA" and "target transcript" are used interchangeably herein.

Selection of appropriate RNAi agents is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of RNAi that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

Selection of an appropriate antisense nucleic acid is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots can be performed to allow a determination of the degree of identity between genes in target species and other species. By performing Southern blots at varying degrees of stringency, as is well known in the art, it is possible to obtain an approximate measure of identity. These procedures allow the selection of antisense nucleic acids that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

Selection of hybridization sites for antisense nucleic acids can be made by one of skill in the art using methods described in the literature. For example, Ding, et al., report a method for defining mRNA hybridization sites based on determining RNA structures using algorithms and thermodynamic and structural properties of the RNA (Ding, et al., 2001, Statistical prediction of single-stranded regions in RNA secondary structure and application to predicting effective antisense target sites and beyond, Nucleic Acids Research 29(5):1034-1046; incorporated herein by reference in its entirety). Sczakiel, et al., also describe a method for computer-supported design of antisense oligonucleotides (Sczakiel, et al., 2000, Theoretical and experimental approaches to design effective antisense oligonucleotides, Frontiers in Bioscience 5: D194-201; Scherr, et al., 2000, RNA accessibility prediction: a theoretical approach is consistent with experimental studies in cell extracts, Nucleic Acids Research 28: 2455-2461; Patzel, et al., 1999, A theoretical approach to select effective antisense oligodeoxyribonucleotides at high statistical probability, J. Biol. Chem. 266:18162-18171; all incorporated herein by reference in their entirety).

Reports of other methods for identifying mRNA hybridization sites used include, e.g., Chiang, et al., who describe a method based on calculating melting temperatures (Chiang, et al., 1991, Antisense oligonucleotides inhibit intercellular adhesion molecule 1 expression by two distinct mechanisms, J. Biol. Chem. 266: 18162-18171, incorporated herein by reference in its entirety). Methods based on calculation of duplex formation free energies have been used (see, e.g., Stull, et al., 1992, Predicting antisense oligonucleotide inhibitory efficacy: a computational approach using histograms and thermodynamic indices, Nucleic Acids Research 20:3501-3508; Ding, et al., 1999, A bayesian statistical algorithm for RNA secondary structure prediction, Comput. Chem. 23:387-400; all incorporated herein by reference in their entirety). Still other methods rely on the use of combinatorial oligonucleotides to identify the hybridization sites within the target RNA. Identification of the hybridization sites is made using RNase H cleavage (Lloyd, et al., 2001, Determination of optimal sites of antisense oligonucleotide cleavage within TNFα mRNA, Nucleic Acids Research 29:3664-3673, incorporated herein by reference in its entirety), microarray analysis (Mir, et al., 1999, Determining the influence of structure on hybridization using oligonucleotide arrays, Nature Biotechnology 17:788-792; and Sohail, et al., 2001, Antisense oligonucleotides selected by hybridization to scanning arrays are effective reagents in vivo, Nucleic Acids Research 29:2041-2051, both incorporated herein by reference in their entirety) or MALDI-TOF mass spectrometry (Altman, et al., 1999, Selection of modified oligonucleotides with increased target affinity via MALDI-monitored nuclease survival assays, J. Comb. Chem. 1:493-508, incorporated herein by reference in its entirety).

The utility of an antisense nucleic acid molecule for modulation (including inhibition) of an mRNA can be readily determined by simple testing. Thus, an in vitro or in vivo expression system comprising the targeted mRNA, mutations or fragments thereof, can be contacted with a particular antisense nucleic acid molecule (modified or unmodified) and levels of expression are compared to a control, that is, using the identical expression system which was not contacted with the antisense nucleic acid molecule. In vitro assays of oligonucleotide activity can also be useful for identifying antisense nucleic acids of the invention. For example, Lloyd, et al., report a direct inverse correlation between predicted chimeric antisense oligonucleotide activities, as determined using an in vitro RNase H assay, and the resultant levels of mRNA and protein expression (Lloyd, et al., 2001, Determination of optimal sites of antisense oligonucleotide cleavage within TNFα mRNA, Nucleic Acids Research 29(17): 3664-3673). According to Lloyd, et al., the ability of the in vitro assay to predict oligonucleotide efficacy was superior to other computationally based RNA structural predictions, ΔG calculations and in vivo trial and error methodologies.

Bcl-2 and molecules that work in conjunction with Bcl-2 are also targets for cancer therapy. B cell leukemia/lymphoma-2 (Bcl-2) is the prototype member of a family of cell death regulatory proteins. Bcl-2 is found mainly in the mitochondria and blocks apoptosis by interfering with the activation of caspases. Gene transfer of Bcl-2 into tumor cells has been shown to enhance their metastatic potential (Miyake et al., 1999). Bcl-2 gene transfer may be applied to bone marrow transplant since Bcl-2 enhances the survival of hematopoietic stem cells after reconstitution of irradiated recipient (Innes et al., 1999). Also, Bcl-2 gene transfer could be useful against neurodegenerating diseases since expression of Bcl-2 in neurons protects them from apoptosis (Saille et al., 1999). Bcl-XS (short isoform) is a dominant negative repressor of Bcl-2 and Bcl-XL. It has been used in gene therapy experiments to initiate apoptosis in tumors that express Bcl-2 and Bcl-XL. Expression of Bcl-XS reduces tumor size (Ealovega et al., 1996) and sensitizes tumor cells to chemotherapeutic agents (Sumatran et al., 1995), suggesting a role for Bcl-XS in initiating cell death in tumors that express Bcl-2 or Bcl-XL (Dole et al., 1996). Expression of these genes or RNAi agents targeting them can be selected as appropriate for the condition being treated.

Equivalent Molecules

The invention comprehends that the therapeutic molecules delivered using the vectors and methods of the present invention can be modified. The nucleic acid molecule encoding a given protein be modified, for instance, due to the degeneracy of codon usage, a coding sequence can be modified, and modified and truncated forms of a protein can be used, such as those which may be found in the literature or analogous to truncated or modified forms found in the literature.

Likewise, analogs, homologs, derivatives, and variants of the coding sequences can be used and analogs, homologs, derivatives and variants of proteins can be expressed; such expressed analogs, homologs, derivatives and variants of proteins can have activity analogous to that of the full-length protein, and the analogs, homologs, derivatives and variants of the protein coding sequence encode such active analogs, homologs, derivatives, and variants.

III. Heterologous Regulatory Sequences

A "first heterologous regulatory sequence" is positioned upstream (5' of) the first heterologous nucleic acid sequence, encoding, e.g., a therapeutic gene. Similarly, a "second heterologous regulatory sequence" can be positioned upstream (5' of) the second heterologous nucleic acid sequence and downstream of the first heterologous nucleic acid sequence, and a "third heterologous regulatory sequence" can be positioned upstream (5' of) the third heterologous nucleic acid sequence and downstream of the second heterologous nucleic acid sequence. A heterologous regulatory sequence can be a sequence that influences, e.g., expression or localization, of a therapeutic molecule encoded by a heterologous nucleic acid sequence. A heterologous regulatory sequence can comprise a promoter, enhancer, protease recognition (cleavage) sequence, internal ribosome binding site, intracellular or intercellular trafficking (transport) signal, etc. Certain heterologous regulatory sequences, e.g., cleavage sequences and trafficking sequences, can be expressed as part of a fusion with a therapeutic molecule.

In embodiments, a heterologous regulatory sequence affects an upstream heterologous nucleic acid sequence. Therefore, a fourth regulatory sequence, located downstream of a third heterologous nucleic acid sequence, can be included in the transfer vector. Also, for example, the second heterologous regulatory sequence can contain elements that affect expression or localization of the first heterologous nucleic acid and its corresponding therapeutic molecule, and the third heterologous regulatory sequence can contain elements that affect expression or localization of the second heterologous nucleic acid and its corresponding therapeutic molecule.

Promoters and Enhancers

The promoter sequence may be homologous or heterologous to the desired gene sequence. A wide range of promoters may be utilized, including viral or mammalian promoters. Cell or tissue specific promoters can be utilized to target expression of gene sequences in specific cell populations. Suitable mammalian and viral promoters for the present invention are available in the art.

Examples of promoters, cellular promoters/enhancers and inducible promoters/enhancers that can be used in combination with the present invention are listed in FIGS. 4 and 5. Any suitable promoter/enhancer combination (as per the Eukaryotic Promoter Database, EPDB) can be used to drive expression of constructs of the invention.

Trafficking Signals

Trafficking signals can direct a molecule to different compartments within a cell, as well as outside the cell and into other cells. An "intercellular trafficking signal," or transport signal, is an amino acid sequence that imparts the property to a protein of being able to pass through membranes between cells. Examples of membrane-penetrating proteins include, but are not limited to, several plant and bacterial protein toxins, such as ricin, abrin, modeccin, diphtheria toxin, cholera toxin, anthrax toxin, heat labile toxins, and *Pseudomonas aeruginosa* exotoxin A. Examples of membrane-penetrating proteins that are not toxins include the TAT protein of human immunodeficiency virus and the protein VP22, the product of the UL49 gene of herpes simplex virus type 1. One line of research involves adapting such molecules from their naturally destructive role into therapeutic compositions.

The effectiveness of lentiviral vectors to deliver genes encoding proteins fused to herpes simplex virus type 1 tegument protein VP22 has been reported (see, e.g., U.S. Pat. App. Pub. No. 2003/0119770). "VP22" denotes: protein VP22 of HSV, e.g., of HSV1, and transport-active fragments and homologues thereof, including transport-active homologues from other herpesviruses including varicella zoster virus VZV, marek's disease virus MDV and bovine herpesvirus BHV.

Among sub-sequences of herpesviral VP22 protein with transport activity, investigators have found that, for example, transport activity is present in polypeptides corresponding to amino acids 60-301 and 159-301 of the full HSV1 VP22 sequence (1-301). A polypeptide consisting of aa 175-301 of the VP22 sequence has markedly less transport activity, and is less preferred in connection with the present invention. Accordingly, the present invention relates in one aspect to a sub-sequence of VP22 containing a sequence starting preferably from about aa 159 (or earlier, towards the N-terminal, in the native VP22 sequence), to about aa 301, and having (relative to the full VP22 sequence) at least one deletion of at least part of the VP22 sequence which can extend for example from the N-terminal to the cited starting point, e.g., a deletion of all or part of the sequence of about aa 1-158. (Less preferably, such a deletion can extend further in the C-terminal direction, e.g., to about aa 175.) For example, partial sequences in the range from about aa 60-301 to about aa 159-301 are provided.

VP22 sequences as contemplated herein extend to homologous proteins and fragments based on sequences of VP22 protein homologues from other herpesviruses, e.g., the invention provides corresponding derivatives and uses of the known VP22-homologue sequences from VZV (e.g., all or homologous parts of the sequence from aa 1-302), from MDV (e.g., all or homologous parts of the sequence from aa 1-249) and from BHV (e.g., all or homologous parts of the sequence from aa 1-258). The sequences of the corresponding proteins from HSV2, VZV, BHV and MDV are available in public protein/nucleic acid sequence databases. Thus, for example, within the EMBL/Genbank database, a VP22 sequence from HSV2 is available as gene item UL49 under accession no. Z86099 containing the complete genome of HSV2 strain HG52; the complete genome of VZV including the homologous gene/protein is available under accession numbers X04370, M14891, M16612; the corresponding protein sequence from BHV is available as "bovine herpesvirus 1 virion tegument protein" under accession number U21137; and the corresponding sequence from MDV is available as gene item UL49 under accession number L10283 for "gallid herpesvirus type 1 homologous sequence genes". In these proteins, especially those from HSV2 and VZV, corresponding deletions can be made, e.g., of sequences homologous to aa 1-159 of VP22 from HSV1. Homologies between these sequences are readily accessible by the use of standard algorithms, default parameters, and software.

Furthermore, chimeric VP22 proteins and protein sequences are also useful within the context of the present invention, e.g., a protein sequence from VP22 of HSV1 for part of which a homologous sequence from the corresponding VP22 homologue of another herpesvirus has been substituted. For example, into the sequence of polypeptide 159-301 from VP22 of HSV1, C-terminal sequences can be substituted from VP22 of HSV2 or from the VP22 homologue of BHV.

Investigators have found that deletion of the 34-amino acid C-terminal sequence from VP22 of HSV1 abolishes transport-activity, thus this sequence region contains essential elements for transport activity. According to a further aspect of the invention, there are provided in-frame fusions comprising a nucleic acid sequence encoding the 34-amino acid C-terminal sequence from VP22, or a variant thereof, together with a sequence for a heterologous nucleic acid sequence. In-frame fusions of nucleic acid sequences encoding modified terminal fragments having at least one mutation insertion or deletion relative to the C-terminal 34 amino acid sequence of HSV1 VP22 are also provided.

Investigators have also been found that sequences necessary for transport activity contain one or a plurality of amino acid sequence motifs or their homologues from the C-terminal sequence of VP22 of HSV1 or other herpesviruses, which can be selected from RSASR (SEQ ID NO: 1), RTASR (SEQ ID NO: 2), RSRAR (SEQ ID NO: 3), RTRAR (SEQ ID NO: 4), ATATR (SEQ ID NO 5), and wherein the third or fourth residue A can be duplicated, e.g., as in RSAASR (SEQ ID NO: 6). Corresponding in-frame fusions of nucleic acid sequences encoding these signals are also provided.

The HIV-1 Tat protein was also reported to enhance intercellular trafficking in vitro. It is composed of 86 amino acids and contains a highly basic region and a cysteine-rich region. It was found that Tat-derived peptides as short as eleven amino acids are sufficient for transduction of proteins (Fawell, et al., 1994, Proc Natl Acad Sci USA 91:664-668). However, the exact mechanism by which the 11-amino acid transduction domain crosses lipid bilayers is poorly understood. Schwarze et al. (Science, 385:1569-1572, 1999)

reported generating a Tat-β-galactosidase fusion protein that was delivered efficiently into brain tissue and skeletal muscle in vivo.

In embodiments of the present invention, a Tat-derived trafficking protein of eleven amino acids Try-Gly-Arg-Lys-lys-Arg-Arg-Gln-Arg-Arg (SEQ ID NO: 7) is used to enhance intercellular trafficking of therapeutic molecules. Any appropriate nucleic acid sequence can be used to express this protein, e.g., tat ggc agg aag aag cgg aga cag cga cga aga (SEQ ID NO:8) with a start codon.

Control of intracellular as well as intercellular transport is contemplated for use in the methods of the invention. This level of control can be used to target therapeutic proteins to particular cellular compartments, e.g., to correct defects for proteins involved in specific disease processes.

Other potentially useful Tat-derived trafficking sequences have been described. For example Chauhan, et al., 2007, The Taming of the Cell Penetrating Domain of the HIV Tat: Myths and Realities, J. Control Release 117(2): 148-162, incorporated herein by reference in its entirety, disclose variants of the Tat protein transduction domain.

Following are Tat-derived cell penetrating peptides described by Chauhan, et al.:

| | | |
|---|---|---|
| PTD | YGRKKRRQRRR | (SEQ ID NO: 9) |
| PTD-4 | YARAAARQARA | (SEQ ID NO: 10) |
| YM-3 | THRLPRRRRRR | (SEQ ID NO: 11) |
| CTP | GGRRARRRRRR | (SEQ ID NO: 12) |

As reported by the authors, depending on the nature of the protein being transported, these peptides effect transport, including transport among cellular compartments. For example, cytoplasmic proteins reportedly end up in the nucleus when PTD is used, nucleo-cytoplasmic proteins go to the nucleus when PTD-4 is used, secretory proteins are found in the nucleus and outside the cell when YM-3 is used, and membrane proteins go to the membrane and nucleus when CTP is used.

Other cell penetrating proteins useful for introducing recombinant proteins into cells are penetratin, polylysine, polyarginine, Kaposi FGF, Syn B1, FGF-4, nuclear localization signal, anthrax toxin derivative 254-amino acids peptide segment, diphtheria toxin "R" binding domain, MPG (described below), WR peptide, and exotoxin A. Penetratin peptide has also been used for siRNA delivery to cells. In embodiments, these proteins or their derivatives used in as trafficking signals in the vectors and methods of the invention.

A fusion peptide, "MPG," has been described for efficient transduction of nucleic acids. This peptide is a bipartite amphipathic peptide obtained by combining the fusion domain of HIV-gp41 protein and the NLS domain of SV40 large T antigen. This peptide is being used as a nanoparticle for transduction of siRNA in vitro and is also available commercially. (See, e.g., Chauhan, et al., 2007; Morris, et al., 1999, A novel potent strategy for gene delivery using a single peptide vector as a carrier, Nucleic Acids Research 27:3510-3517.)

In embodiments of the vectors and methods of the invention, an siRNA or other antisense agent is transported intercellularly or intracellularly.

The inventive transfer vector may include splice acceptor and splice donor sequences flanking the gene construct. In the case of multigene transfer vector, the splice acceptor sequence may be inserted upstream of the first promoter-structural gene unit and splice donor site may be located in the downstream of the last promoter-structural gene unit in the 5' to 3' order. A mammalian insulator sequence (MIS) may be inserted downstream of the gene units, or if specific promoters are used for the gene units, then the MIS may be placed before the first gene unit and after the last gene unit followed by splice donor site. A translation initiation sequence may also be included in the multigene gene transfer vector. The use of the translation initiation sequence causes the second and subsequent multigene units to be expressed evenly and stably compared with the first gene expression product.

Translation Initiation Sequence

The transfer vector may optionally comprise a sequence that allows for translation initiation in the middle of a messenger RNA (mRNA) sequence as part of the greater process of protein synthesis. While this sequence may be typically IRES other sequences may be used, which may have a similar sequence.

Splice Acceptor/Splice Donor Sequence

The transfer vector may optionally comprise a promoter-gene sequence flanked by a splice acceptor site 5' to a gene unit and a splice donor site 3' to the promoter-gene. For instance, the following elements may be present 5' to 3': a splice acceptor site, first promoter for the first gene unit, first heterologous nucleic acid sequence and splice donor site 3' to the first gene unit, then a splice acceptor site and a second promoter for the second gene, the second heterologous nucleic acid sequence, splice donor site, and then if there is a third gene, a splice acceptor site, third promoter for the third gene unit, the third heterologous nucleic acid sequence, and a splice donor site, and so forth. The splice acceptor or donor site typically may include about 5 to 10 bases.

Mammalian Insulator Sequence (MIS)

The transfer vector may optionally comprise an insulator sequence, in particular mammalian insulator sequence (MIS). Insulators are DNA sequence elements that can protect against the activation influence of distal enhancers associated with other genes, and also help to preserve the independent function of genes embedded in a genome in which they are surrounded by regulatory signals so that cross interaction is avoided. The insulators as used in the present application may not necessarily be limited to use in lentiviruses. The insulators may be used with other viral vectors.

To provide background on these insulator sequences, the zinc finger protein CCCTC-binding factor (CTCF) is a versatile transcription regulator that binds to insulators and shows enhancer-blocking activity for regulating gene expression control. Chicken (beta-globin) insulator with about 1.2 kb is widely used in vitro or in vivo animals, but generally does not have human or mammalian compatible factors to be entirely useful in treating humans or mammals.

Bovine or human growth hormone transcriptional stop sequences may also be used as insulators. A short-element of about 238 bp containing the "HS" DNA element core sequence, which is the binding site for CTCF is also effective as an "enhancer blocking" element. Template DNA for generation of such element, for example a pcDNA3, which contains bovine growth hormone transcriptional stop sequence may be as follows: PCR primers: 5' agctagatagtgt-cacctaaatgc-3' (SEQ ID NO:13) and 5'-agcatgcctgctatt-3' (SEQ ID NO:14).

A binding site for the transcription factor CTCF may be responsible for enhancer-blocking activity in a variety of insulators, including the insulators at the 5' and 3' chromatin boundaries of the chicken and human beta-globin locus. The minimal element responsible for this activity may be a binding site for CTCF.

When several different sequences of insulators of 5' and 3' HS/CTCF are compared using "human insulator" as the template, there are at least two mutations in the mouse, at least 5 mutations in chicken at the 5' HS/CTCF. In addition, there are at least two mutations in mouse, at least 4 mutations at the 3' HS/CTCF.

The insulator sequence as used in the lentivirus transfer vector may be placed as follows. In a single gene vector where a general promoter is used to control gene expression, MIS may be placed 3' of the gene and upstream of the splicing donor site. However, if a specific promoter is used to control the expression of the gene, the MIS may be placed upstream of the specific promoter and downstream of the gene, wherein the MIS sequences are optionally flanked by the splice acceptor on the 5' side and splice donor on the 3' side of the gene. In a single gene construct, for RNAi expression where specific promoter is used, MIS may flank the specific promoter-structural gene construct, optionally with a splice donor site downstream of the 3' MIS. Two or more MIS may be used together to enhance the blocking effects.

For multiple gene vectors, if a general promoter is used, an MIS may be included downstream of the gene units with splice donor site 3' to the MIS. However, if a specific promoter is used MIS is place upstream of the first specific promoter for the first structural gene, and another MIS downstream of the last specific promoter-structural gene set. The MIS are optionally flanked by splice acceptor on the 5' side and splice donor on the 3' side.

IV. Therapeutic Applications

The invention includes a variety of therapeutic applications for the lentiviral vectors of the invention. In particular, lentiviral vectors are useful for gene therapy. Exemplary therapeutic applications are listed in FIG. 7. The invention provides methods of treating and/or preventing infection by an infectious agent, the method comprising administering to a subject prior to, simultaneously with, or after exposure of the subject to the infectious agent a composition comprising an effective amount of a lentiviral vector, wherein the lentiviral vector directs transcription of at least one RNA that hybridizes to form an shRNA or siRNA that is targeted to a transcript produced during infection by the infectious agent, which transcript is characterized in that reduction in levels of the transcript delays, prevents, and/or inhibits one or more aspects of infection by and/or replication of the infectious agent.

The invention provides methods of treating a disease or clinical condition by, for example, removing a population of cells from a subject at risk of or suffering from the disease or clinical condition and engineering or manipulating the cells to comprise an effective amount of therapeutic agents by infecting or transfecting the cells with a lentiviral vector. At least a portion of the cells are returned to the subject.

Without limitation, therapeutic approaches may find particular use in diseases such as cancer, in which a mutation in a cellular gene is responsible for or contributes to the pathogenesis of the disease, and in which specific inhibition of the target transcript bearing the mutation may be achieved by expressing an RNAi agent targeted to the target transcript within the cells, without interfering with expression of the normal (i.e. non-mutated) allele. Furthermore, treatment of any cancer in which P53 expression is defective is contemplated using the vectors and methods of the invention.

The invention is also useful for the treatment of genetic diseases, for example, Gaucher's Disease and Fabry's Disease. Gaucher's disease is a lysosomal storage disease caused by a deficiency of the enzyme glucocerebrosidase. This deficiency leads to an accumulation of the enzyme substrate, the fatty substance glucocerebroside (also known as glucosylceramide). Fatty material can collect in the spleen, liver, kidneys, lungs, brain and bone marrow. It has been reported, using a mouse model for Gaucher's Disease, that a lentiviral vector can transduce HSCs that are capable of long-term gene expression in vivo (Kim, et al., 2005, "Long-term expression of the human glucocerebrosidase gene in vivo after transplantation of bone-marrow-derived cells transformed with a lentivirus vector, J. Gene Med. 7:878-887, incorporated herein by reference).

According to certain embodiments of the invention, rather than removing cells from the body of a subject, infecting or transfecting them in tissue culture, and then returning them to the subject, inventive lentiviral vectors or lentiviruses are delivered directly to the subject.

Neurological Disorders

Cells infected with a recombinant lentivirus of the invention, in vivo, or ex vivo, used for treatment of a neuronal disorder for example, may optionally contain an exogenous gene, for example, a gene which encodes a receptor or a gene which encodes a ligand. Such receptors include receptors which respond to dopamine, GABA, adrenaline, noradrenaline, serotonin, glutamate, acetylcholine and other neuropeptides, as described above. Examples of ligands which may provide a therapeutic effect in a neuronal disorder include dopamine, adrenaline, noradrenaline, acetylcholine, gamma-aminobutyric acid and serotonin. The diffusion and uptake of a required ligand after secretion by an infected donor cell would be beneficial in a disorder where the subject's neural cell is defective in the production of such a gene product. A cell genetically modified to secrete a neurotrophic factor, such as nerve growth factor (NGF), might be used to prevent degeneration of cholinergic neurons that might otherwise die without treatment. Alternatively, cells can be grafted into a subject with a disorder of the basal ganglia, such as Parkinson's disease, or can be modified to contain an exogenous gene encoding L-DOPA, the precursor to dopamine. Parkinson's disease is characterized by a loss of dopamine neurons in the substantia nigra of the midbrain, which have the basal ganglia as their major target organ.

U.S. Pat. No. 6,800,281, "Lentiviral-mediated growth factor gene therapy for neurodegenerative diseases," incorporated herein by reference in its entirety, describes methods for treating Parkinson's Disease using glial cell derived neurotrophic factor (GDNF), highly conserved neurotrophic factor that potently promotes the survival of many types of neurons.

Parkinson's disease (PD) is a neurodegenerative disorder characterized by the loss of the nigrostriatal pathway; a progressive disorder resulting from degeneration of dopaminergic neurons within the substantia nigra. Although the cause of Parkinson's disease is not known, it is associated with the progressive death of dopaminergic (tyrosine hydroxylase (TH) positive) mesencephalic neurons, inducing motor impairment. The characteristic symptoms of Parkinson's disease appear when up to 70% of TH-positive nigrostriatal neurons have degenerated. Surgical therapies aimed at replacing lost dopaminergic neurons or disrupting aberrant basal ganglia circuitry have recently been tested (C. Honey et al. 1999). However, these clinical trials have focused on patients with advanced disease, and the primary goal of forestalling disease progression in newly diagnosed patients has yet to be realized. The administration can be by stereotaxic injection. The administration can be intracranially, e.g., intracranially to striatum or to substantia nigra. The administration can also be by retrograde transport.

In an embodiment, the administration site is the striatum of the brain, in particular the caudate putamen. Injection into the putamen can label target sites located in various distant regions of the brain, for example, the globus pallidus, amygdala, subthalamic nucleus or the substantia nigra. Transduction of cells in the pallidus commonly causes retrograde labelling of cells in the thalamus. In a preferred embodiment the (or one of the) target site(s) is the substantia nigra.

In another embodiment the vector system is injected directly into the spinal cord. This administration site accesses distal connections in the brain stem and cortex. Within a given target site, the vector system may transduce a target cell. The target cell may be a cell found in nervous tissue, such as a neuron, astrocyte, oligodendrocyte, microglia or ependymal cell. In a preferred embodiment, the target cell is a neuron, in particular a TH positive neuron.

The vector system can be administered by direct injection. Methods for injection into the brain (in particular the striatum) are well known in the art (Bilang-Bleuel et al (1997) Proc. Acad. Nati. Sci. USA 94:8818-8823; Choi-Lundberg et al (1998) Exp. Neurol.154:261-275; Choi-Lundberg et al (1997) Science 275:838-841; and Mandel et al (1997)) Proc. Acad. Natl. Sci. USA 94:14083-14088). Stereotaxic injections maybe given.

Administration of the cells or virus into selected regions of the recipient subject's brain may be made by drilling a hole and piercing the dura to permit the needle of a microsyringe to be inserted. The cells or recombinant lentivirus can alternatively be injected intrathecally into the spinal cord region. A cell preparation infected ex vivo, or the recombinant lentivirus of the invention, permits grafting of neuronal cells to any predetermined site in the brain or spinal cord, and allows multiple grafting simultaneously in several different sites using the same cell suspension or viral suspension and permits mixtures of cells from different anatomical regions.

For transduction in tissues such as the brain, it is necessary to use very small volumes, so the viral preparation is concentrated by ultracentrifugation. The resulting preparation should have at least $10^8$ pfu./ml, preferably from $10^8$ to $10^{10}$ pfu./ml, more preferably at least $10^9$ pfu./ml. (The titer is expressed in transducing units per ml (pfu./ml) as titered on a standard D17 cell line). It has been found that improved dispersion of transgene expression can be obtained by increasing the number of injection sites and decreasing the rate of injection (Horellou and Mallet (1997) as above). Usually between 1 and 10 injection sites are used, more commonly between 2 and 6. For a dose comprising $1-5 \times 10^9$ pfu./ml, the rate of injection is commonly between 0.1 and 10 µl/min, usually about 1 µl/min.

In another embodiment the vector system is administered to a peripheral administration site. The vector may be administered to any part of the body from which it can travel to the target site by retrograde transport. In other words the vector may be administered to any part of the body to which a neuron within the target site projects.

The "periphery" can be considered to be all part of the body other than the CNS (brain and spinal cord). In particular, peripheral sites are those which are distant to the CNS. Sensory neurons may be accessed by administration to any tissue which is innervated by the neuron. In particular this includes the skin, muscles and the sciatic nerve.

In another embodiment the vector system is administered intramuscularly. In this way, the system can access a distant target site via the neurons which innervate the innoculated muscle. The vector system may thus be used to access the CNS (in particular the spinal cord), obviating the need for direct injection into this tissue. There is thus provided a non-invasive method for transducing a neuron within the CNS. Muscular administration also enables multiple doses to be administered over a prolonged period.

Other neuronal disorders that can be treated similarly by the method of the invention include Alzheimer's disease, Huntington's disease, neuronal damage due to stroke, and damage in the spinal cord. Alzheimer's disease is characterized by degeneration of the cholinergic neurons of the basal forebrain. The neurotransmitter for these neurons is acetylcholine, which is necessary for their survival. Engraftment of cholinergic cells infected with a recombinant lentivirus of the invention containing an exogenous gene for a factor which would promote survival of these neurons can be accomplished by the method of the invention, as described. Following a stroke, there is selective loss of cells in the CA1 of the hippocampus as well as cortical cell loss which may underlie cognitive function and memory loss in these patients. Once identified, molecules responsible for CA1 cell death can be inhibited by the methods of this invention. For example, antisense sequences, or a gene encoding an antagonist can be transferred to a neuronal cell and implanted into the hippocampal region of the brain.

The method of transferring nucleic acid also contemplates the grafting of neuroblasts in combination with other therapeutic procedures useful in the treatment of disorders of the CNS. For example, the lentiviral infected cells can be co-administered with agents such as growth factors, gangliosides, antibiotics, neurotransmitters, neurohormones, toxins, neurite promoting molecules and antimetabolites and precursors of these molecules such as the precursor of dopamine, L-DOPA.

Further, there are a number of inherited neurologic diseases in which defective genes may be replaced including: lysosomal storage diseases such as those involving β-hexosamimidase or glucocerebrosidase; deficiencies in hypoxanthine phosphoribosyl transferase activity (the "Lesch-Nyhan" syndrome); amyloid polyneuropathies (-prealbumin); Duchenne's muscular dystrophy, and retinoblastoma, for example.

For diseases due to deficiency of a protein product, gene transfer could introduce a normal gene into the affected tissues for replacement therapy, as well as to create animal models for the disease using antisense mutations. For example, it may be desirable to insert a Factor IX encoding nucleic acid into a lentivirus for infection of a muscle or liver cell.

Stem cell therapy contemplates injection of stem cells transduced by a lentiviral vector carrying a therapeutic gene of interest into a fetus central nervous system. The correction or rescue of a genetic defect is achieved during cell differentiation. Stem cells at a nondividing stage should be efficiently transduced by such a vector using a convenient infection technique.

V. Pharmaceutical Compositions

The invention further provides pharmaceutical compositions comprising lentiviral vectors of the invention and one or more pharmaceutically acceptable carriers.

The pharmacologically active compounds of this invention can be processed in accordance with conventional methods of galenic pharmacy to produce medicinal agents for administration to patients, e.g., mammals including humans.

The compounds of this invention can be employed in admixture with conventional excipients, i.e., pharmaceutically acceptable organic or inorganic carrier substances suitable for parenteral, enteral (e.g., oral) or topical application, which do not deleteriously react with the active compounds. Suitable pharmaceutically acceptable carriers include but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins.

For parenteral application, particularly suitable are injectable, sterile solutions, preferably oily or aqueous solutions, as well as suspensions, emulsions, or implants, including suppositories. Ampoules are convenient unit dosages.

For enteral application, particularly suitable are tablets, dragees, liquids, drops, suppositories, or capsules. A syrup, elixir, or the like can be used wherein a sweetened vehicle is employed.

Sustained or directed release compositions can be formulated, e.g., by inclusion in liposomes or those wherein the active compound is protected with differentially degradable coatings, e.g., by microencapsulation, multiple coatings, etc. It is also possible to freeze-dry these compounds and use the lyophilizates obtained, for example, for the preparation of products for injection.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

It will be appreciated that the actual preferred amounts of active compound in a specific case will vary according to the specific compound being utilized, the compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The lentiviral vectors of the invention can also be administered in combination with other agents, for example, chemotherapeutic agents, radiation treatment, or steroids, according to methods known and described in the art. PCT Publication WO 2008/08069942, "Novel Methods of Enhancing Delivery of a Gene Therapy Vector Using Steroids," describes methods for enhancing expression of a viral vector-encoded therapeutic gene product by delivering to a subject the viral vector in conjunction with a steroid, e.g., prednisolone, cortisone, corticosterone, or dexamethasone. In embodiments, the individual therapies being combined are not necessarily administered together, e.g., they can be administered separately via different modes of administration, alternately, etc.

VII. Patients

The invention contemplates treatment of patients including human patients. The term patient as used in the present application refers to all different types of mammals including humans and the present invention is effective with respect to all such mammals. The present invention is effective in treating any mammalian species which have a disease potentially remedied by delivery of a gene product or inhibition of expression of a gene.

The contents of all cited references, including literature references, issued patents, published patent applications, and co-pending patent applications, cited throughout this application are hereby expressly incorporated by reference in their entirety.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1- Vector Construction

The additional components of the gene transfer system include a packaging (helper) plasmid and an envelope (Env) plasmid encoding VSV-G driven by the HIV-1 LTR (Mochizuki, H. et al., 1998, J Virol 72:8873-8883; Reiser, J. et al., 1996, PNAS USA 93:15266-15271). These packaging and envelope constructs are described herein and by Lai et al., 2000, PNAS, 97: 11297-11302, and Lai, et al., 2002, Neurosci. Res. 67: 363-371, incorporated herein by reference. The helper construct has a deletion in the packaging signal rendering it inactive, and the 5' LTR is replaced with the CMV-IE promoter. The CMV promoter was derived from pcDNA 3.1, which was used as a template for a PCR reaction yielding 590 bp of the CMV promoter. The HIV-1 helper construct was digested by EcoRV (33) and Afl II (517) to have generate a deletion of 475 bp from the U3 region of the 5' LTR. Insertion of the CMV promoter PCR fragment was then ligated into the HIV-1 helper construct to create a safer Tat-independent construct without compromising viral titer. The viral genes tat and nef were also inactivated. Pseudotyped vectors were produced in human embryonic kidney 293T cells using a three-component transient packaging system (Mochizuki, H. et al., 1998).

The transfer vectors were based on HIV-1 lentivirus vectors, and were made using methods similar to those described by Kim, et al., J. Gene Med. (2005), referenced above. The transfer vectors of the present invention are self-inactivating, i.e., they have a deletion in the U3 region of the 5' LTR that was introduced as follows: (a) the fragment between Nef and the 3' LTR was isolated by digesting with Xho-I and Afl-II; (b) the isolated fragment of about 820 bp was subcloned into the PUC18 vector; (c) the U3 region (containing the TATA box, SP1) of the 3' LTR of about 337 bp was deleted by EcoR-V and Rsa-I; and (d) a PCR fragment from (c) containing the regions of Nef and the 3' LTR with the U3 deletion were ligated back into the lentiviral vector.

Figure 6:
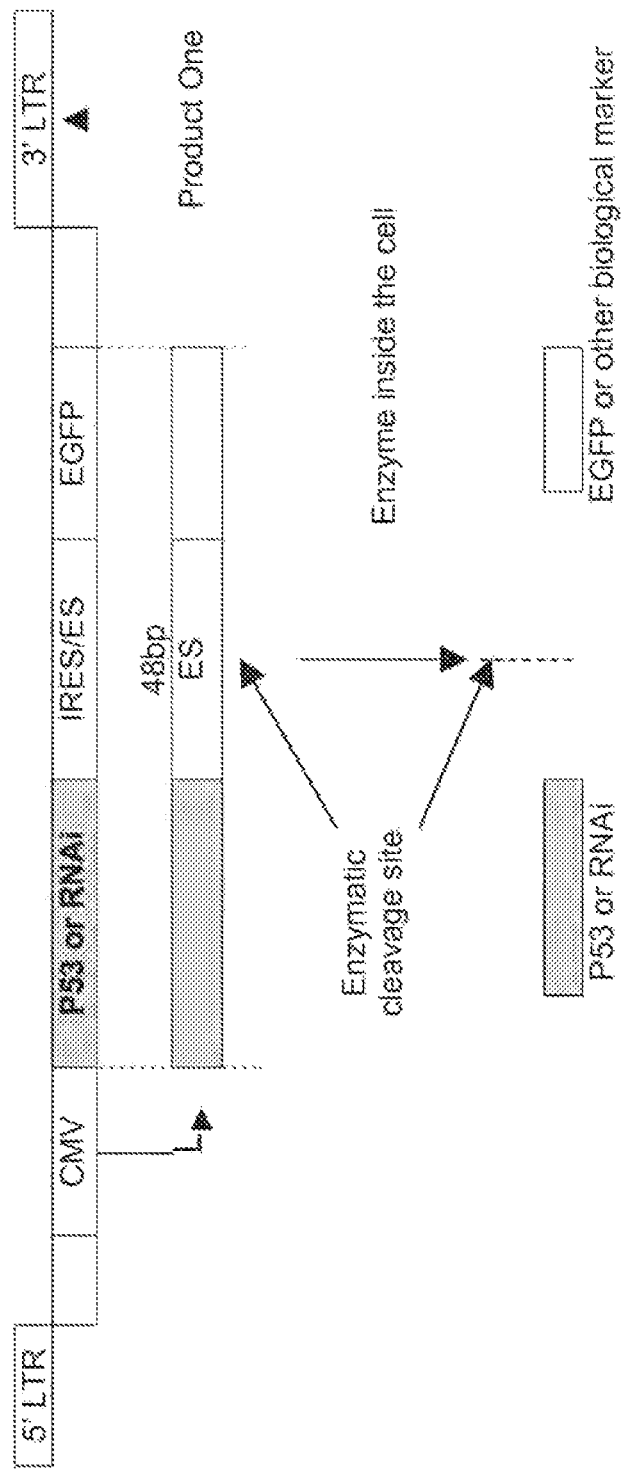
FIG. 6 SIN-LV-P53-EGFP and SIN-LV-BCL2 RNAi-EGFP. The drawing shows the vector constructs used as described in the Examples.

Example 2—In Vitro Infection of a Prostate Cancer Cell Line with SIN-HIV-P53-EGFP PC-3 (prostate cancer) cells were infected with a lentivirus containing a gene transfer vector expressing wild-type P53 and EGFP. Three groups were tested. Treatment group: PC-3 cells were treated with SIN-HIV-P53-EGFP (construct shown in FIG. 6). Control (negative) group: PC-3 cells were untreated. Control (positive) group: Normal cells were treated or not treated with SIN-HIV-P53-EGFP.

Figure 8A:
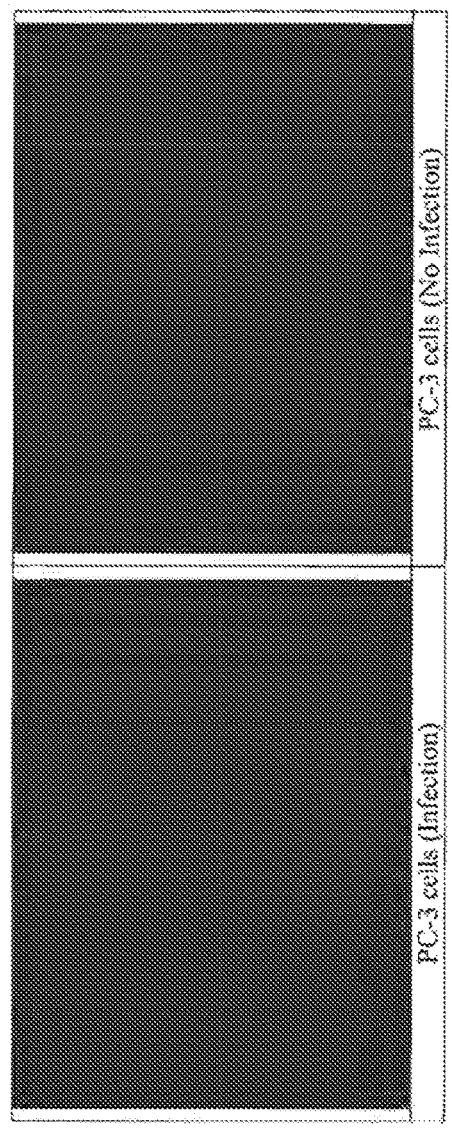
FIGS. 8A-8D Infection of Prostate Cancer Cells.
Figure 8B:
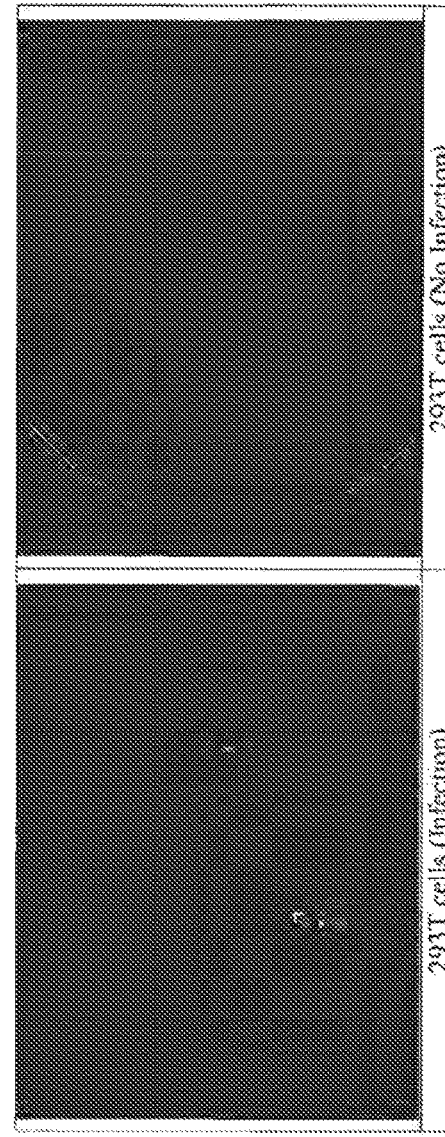
Figure 8C:
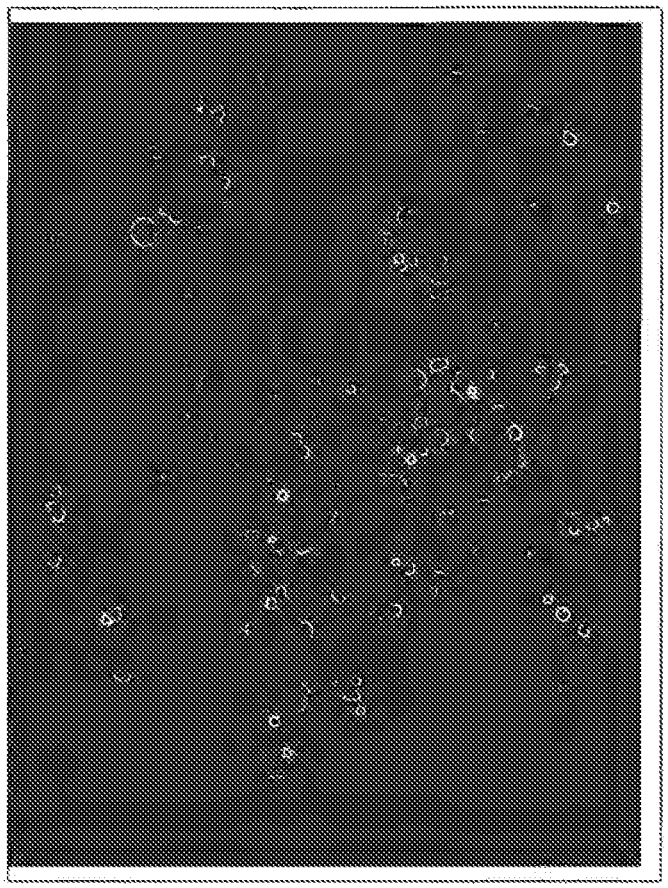
Figure 8D:
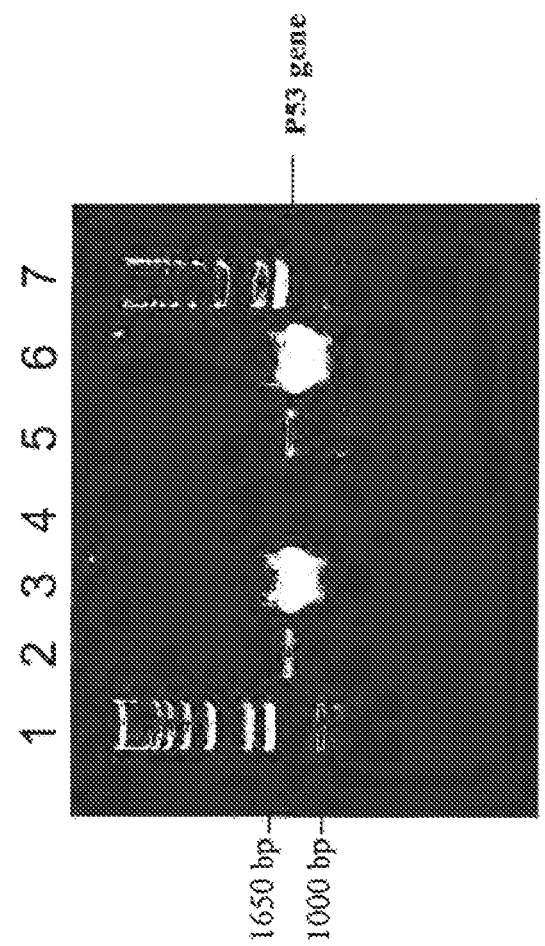

Prostate cancer cell-lines (PC-3) and 293-T cells were placed into the 12 well-plate with $0.4 \times 10^6$ cells, and were cultured in the RPMI 1640 and DMEM medium containing antibiotics. 200 µl of the packaged lentiviral vector SIN-CMV-p53-IRES/CS-EGFP (see FIG. 1C) was added to the cells for the infection study under 1 mg/ml. The cells were then cultured by incubating for 6-16 hours at 37° C. in a $CO_2$ incubator. After infection for 48-72 hours, we evaluated the expression of EGFP using a fluorescence microscope in both the transduced PC-3 and 239-T cells. We found that a high level of EGFP was expressed in both PC-3 and 293-T cells transduced by SIN-CMV-p53-IRES/CS-EGFP, but not in the control group of those cells that were not infected (FIGS. 8A-C). The results indicated that our vector system worked well to express both transgenes simultaneously.

After treatment, RNA was isolated from the cells, and RT-PCR was used to determine the p53 expression level at different time points. Corresponding cell growth curves and survival cell numbers were determined at different time points, and the results for treated and untreated cells compared.

To evaluate confirm P53 expression, we extracted total RNA 96 hours after infection. 0.5 µg total RNA from each group (treated and untreated) were used as template for RT-PCR. P53 mRNA was amplified using sense primer (from the partial promoter of CMV: 5'-tacgtattagtcatcgctatt-3) and antisense primer (from the end of the P53 gene: 5'-aggcctcattcagctctcgga-3'). The results showed that the cell lines infected by the vector expressed a high level of P53, and the uninfected cell lines expressed only the basic level of endogenous p53 (see FIG. 8D). Thus, our data indicated that our vector system is functional for highly expressing both the two transgene protein in the cells at the same time.

We also compared growth and survival of the prostate cancer cells transduced with the vector with untreated cells. Taking time points for up to one week, we observed the growth condition and cell numbers under the light and fluorescent microscopes. Expression of EGFP indicated transduction by the vector. We observed that PC-3 cells transduced by the vector died quickly compared with the untreated PC-3 cells, and that both treated and untreated 293-T cells showed growth and no significant cell death. The result can be confirmed using FACS analysis to quantitate cell numbers at the respective time points.

Example 3—In Vivo Transduction with SIN-HIV-P53-EGFP and SIN-HIV-P53Bc1-2 RNAi Transduction with the SIN-HIV-P53-EGFP vector described in Example II, expressing P53 and GFP, or SIN-HIV-P53-Bc1-2 RNAi, expressing P53 and an RNAi agent targeting human Bc1-2, is done in vivo. See FIG. 1C, Panel B, upper construct (CMV-P53-hPSA-Bc1-2 RNAi). The NOD SCID mouse model, characterized by a major immunodeficiency, is used to study gene therapy for prostate cancer using lentiviral transfer systems of the invention.

NOD SCID mice are subcutaneously implanted with a PC-3 cell suspension in a thoracic postero-lateral wound. Tumor cell suspensions are injected using a 30-gauge needle and a 1-ml disposable syringe. The volume of inoculation is 100 µl ($2 \times 10^6$ tumor cells suspended in 100 µl of PBS). After tumor appearance (1-2 weeks post-implantation), the virus injections are made.

Tumor progression is monitored by palpation twice a week by the investigator, and subcutaneous tumor size is measured using a caliper. Viral vector is administered at a titer of about $10^8$ pfu/ml, by tail-vein injection. Animals are euthanized according to tumor size or clinical status during the observation period. Cervical dislocation is performed 2 to 4 weeks after injection.

Prostate cancer tumor sizes are measured, and for EGFP immunostaining to evaluate distribution of the vector, liver, lung, heart, and bone marrow cells are harvested. These tissue samples are collected for immunostaining does as described by Lai, et al., PNAS, 2002. The tissues are subjected to total RNA and protein extractions, to evaluate expression of the transgenes. The tissue slides are made and examined for EGFP fluorescence under the fluorescence microscope, to determine the distribution of the vector and thereby identify target tissues in the animal model. P53 expression is evaluated by RT-PCR of tissue observed to express EGFP under the fluorescent microscope. The function of the RNAi agent targeted to bc1-2 is be tested by both RT-PCR of RNA and Western-blot protein analysis in the same samples, to determine whether the level of Bc1-2 in tumor tissue is significantly downregulated in the same target cells that express EGFP.

Co-localization of the target cells expressing the P53 or RNAi and EGFP simultaneously is evaluated, particularly those cells in tumors that underwent size reduction as a result of vector treatment. The distribution, e.g., in bone marrow, of the vector after i. v. injection is also determined, to provide information useful for human clinical trials using the vector coexpressing P53 and a bcl-2 RNAi agent.

Example 4—In Vitro Synergistic Effects of SIN-HIV-P53-Bc1-2 RNAi

Figures 10A, 10B:
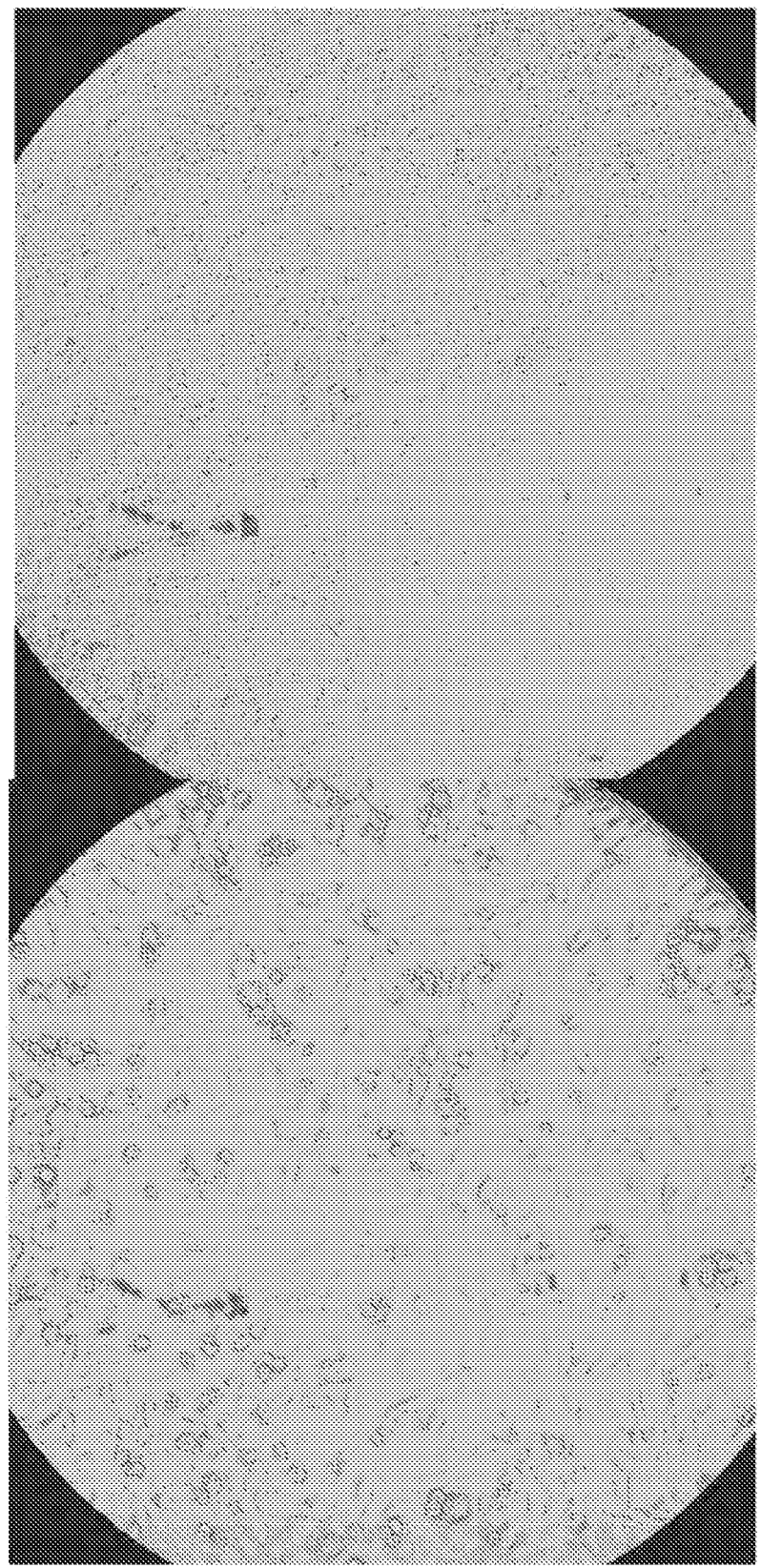
FIGS. 10A-10B Experimental evidence of efficacy of the viral vector construct P53-Bcl-2 RNAi, expressing P53 and an RNAi agent targeting human Bcl-2.

PC3 prostate cancer cells grown on a substrate were contacted with double gene viral vector construct that express P53 and Bcl-2 RNAi, which is discussed above. FIGS. 10A and 10B show in vitro test results that show that double gene (P53 and Bcl-2 RNAi) expression construct viral vector induces cell necrosis of PC3 prostate cancer cells. In living culture, FIG. 10A shows the untreated cells, and the FIG. 10B shows cells treated with the double gene vector.

However, when tested on human embryonic kidney cells (293T), the double gene construct did not cause necrosis.

Figures 11A, 11B:
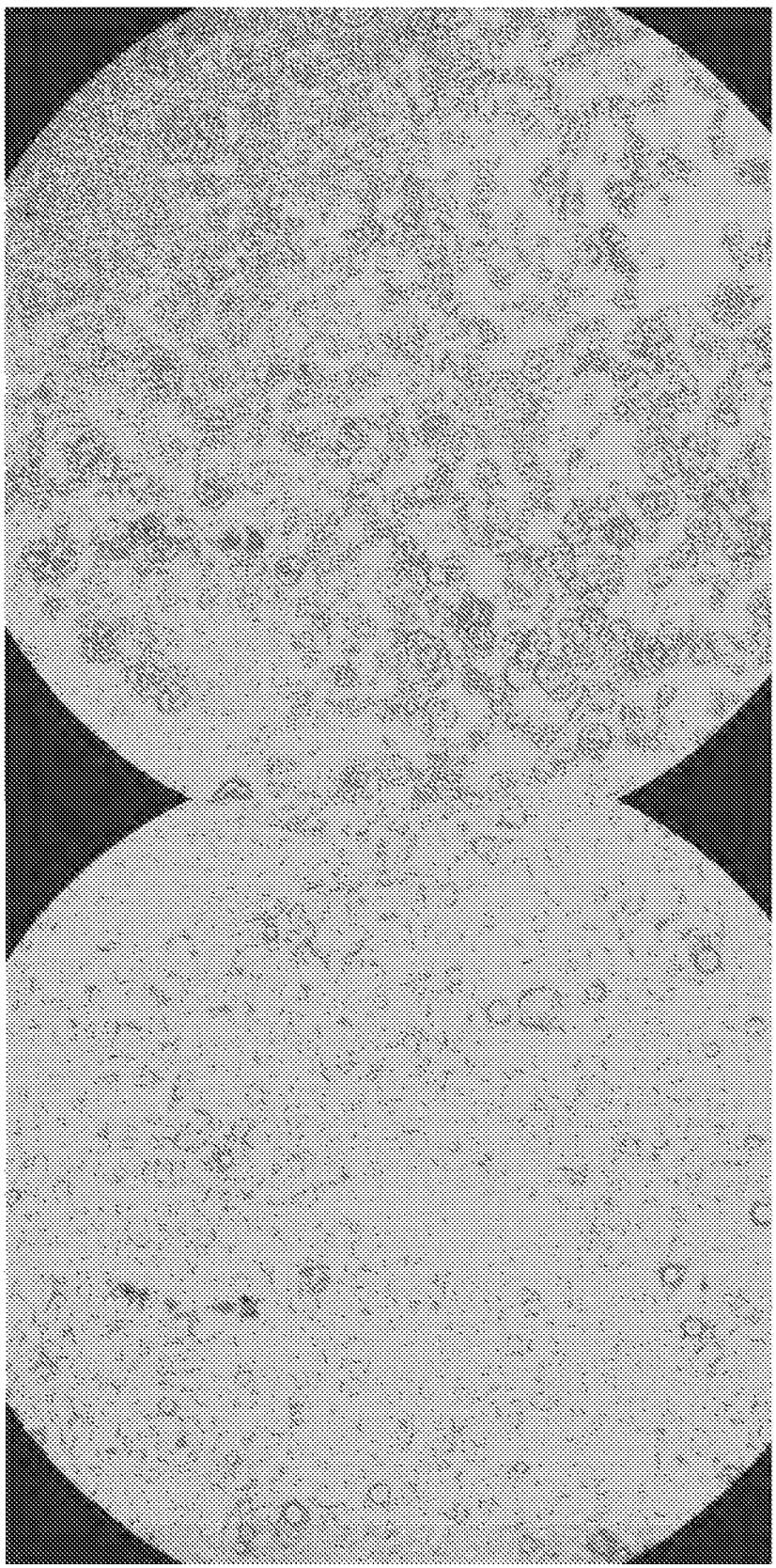
FIGS. 11A-11B Experimental evidence of efficacy of the viral vector construct P53-Bcl-2 RNAi, expressing P53 and an RNAi agent targeting human Bcl-2.

FIG. 11A shows the untreated cells and FIG. 11B shows cells treated with the viral vector construct P53-Bc1-2 RNAi, expressing P53 and an RNAi agent targeting human Bc1-2. No difference in necrosis is observed, indicating specificity of the double gene construct for prostate tumor. The cells were observed three days after infection.

Figure 12:
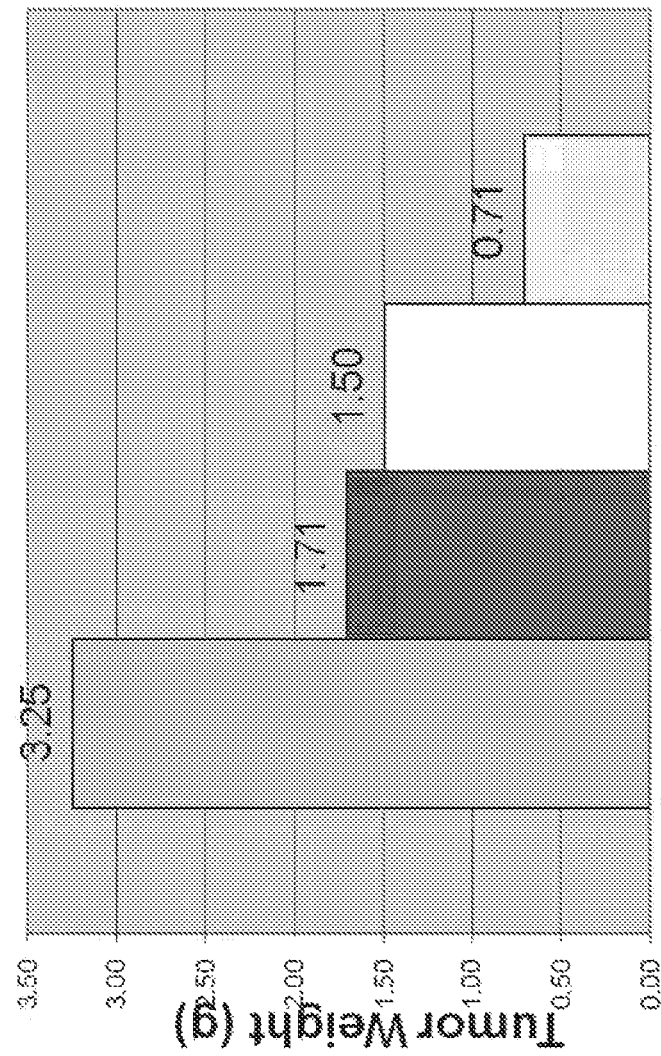
FIG. 12 In vivo test demonstrates tumor reduction efficacy of viral vector construct P53-Bcl-2 RNAi, expressing P53 and an RNAi agent targeting human Bcl-2. In order from left to right, far left bar is weight of the control tumor group after three weeks; tumor treated with P53 alone expressed through viral vector construct (repair genetic defect); tumor treated with BCL2 SiRNA alone expressed through viral vector construct (down regulation of BCL2 gene) only; and on the far right tumor treated with viral vector construct P53-Bcl-2 RNAi, expressing P53 and an RNAi agent targeting human Bcl-2 for simultaneous P53 (repair) and BCL2 siRNA.

Example 5— In Vivo Synergistic Effects of SIN-HIV-P53-Bc1-2 RNAi Over P53 and Bc1 RNAi Alone—First Study In vivo effects of the double gene construct and the individual single gene constructs were compared against prostate tumor. The results show that synergistic tumor reducing effects were seen for the viral vector construct P53-Bc1-2 RNAi, expressing P53 and an RNAi agent targeting human Bc1-2. FIG. 12 is a graph showing this effect. In order from left to right, far left bar is untreated control group; P53 alone expressed through viral vector construct (repair); Bc1-2 siRNA alone expressed through viral vector construct (downregulation of BCL2 gene) only; and on the far right viral vector construct P53-Bc1-2 RNAi, expressing P53 and an RNAi agent targeting human Bc1-2 for simultaneous P53 (repair) and Bc1-2 siRNA. Whereas application of P53 gene construct alone reduced the tumor weight to 1.71 grams, and 1.5 grams when only Bc1-2 siRNA construct was applied, application of the combination gene construct resulted in the tumor weight of 0.71 grams, indicating a synergistic effect of the double gene construct.

In the in vivo studies, 100 µl of viruses ($5.0 \times 10^8$ cells) were injected into the tail vein of mice for three weeks. After injection for three weeks, the mice were sacrificed and tumors were harvested and weighed.

Figures 13A, 13B:
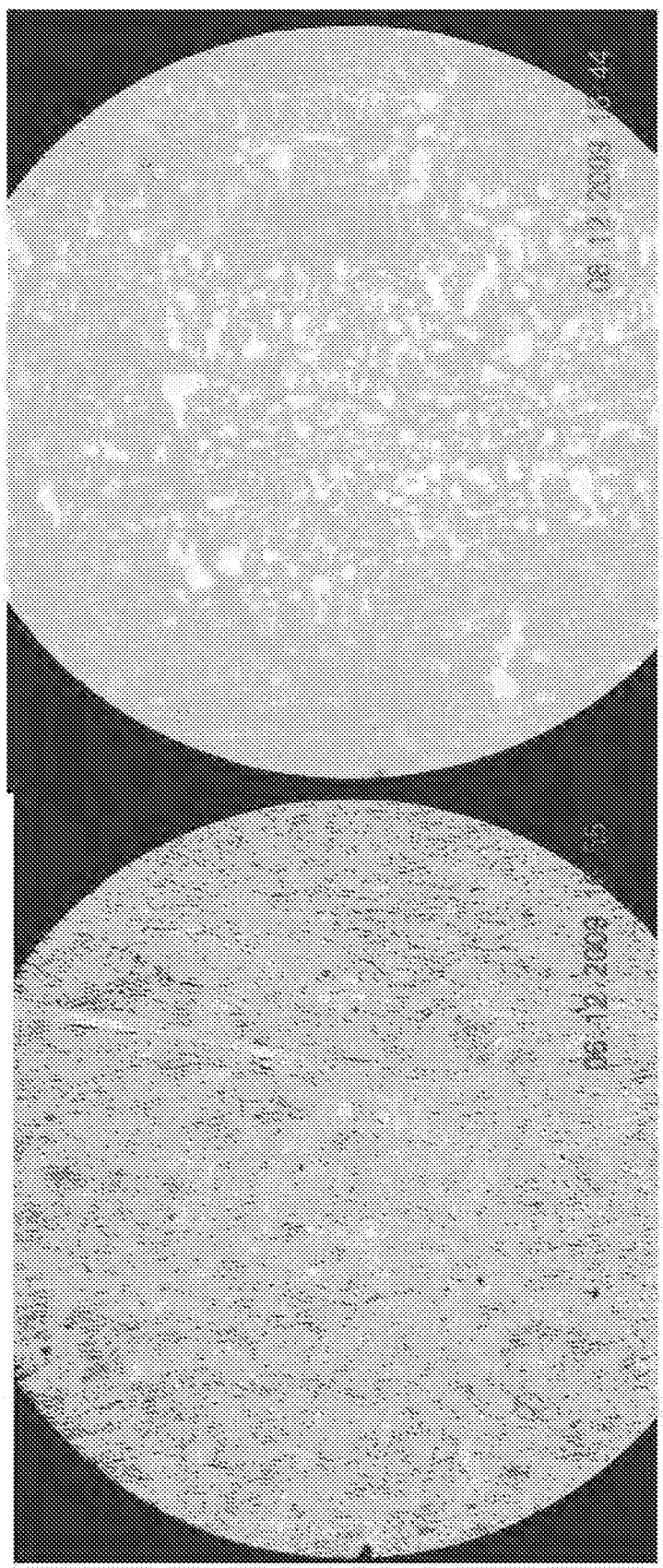
FIGS. 13A-13B show in vivo tumor staining of control (untreated tumor) versus treatment groups. Immunohistochemical staining by specific antibodies show that tumor cells treated with viral vector construct P53-Bcl-2 RNAi, expressing P53 and an RNAi agent targeting human Bcl-2 no longer produce hPSA (human prostate specific antigen), which means that the cells are no longer active tumor cells or are no longer actively cancerous.

Further, cells obtained from the untreated tumor and tumor treated with the double gene construct were examined for human prostate-specific antigen (hPSA) expression. FIGS. 13A and 13B show staining of control (untreated tumor) versus the treatment group. The results show that tumor cells treated with viral vector construct P53-Bc1-2 RNAi, expressing P53 and an RNAi agent targeting human Bc1-2 no longer produce hPSA, which means that the cells are no longer active tumor cells or are no longer actively cancerous. After human prostate specific antibody staining, FIG. 13A shows the control tumor, which expresses hPSA, and FIG. 13B shows treatment tumor that shows cell necrosis and no expression of hPSA.

Example 6— In Vivo Synergistic Effects of SIN-HIV-P53-Bc1-2 RNAi Over P53 and Bc1 RNAi Alone—Second Study A second study was carried out using mouse models for prostate cancer using the individual gene constructs for P53 and Bc1-2 RNAi, and the double gene construct that carry both of these genes. Multiple mice were tested. V1 Group is mice treated with P53 gene construct alone, V2 Group is mice treated with Bc1-2 RNAi construct alone, and V3 Group is mice treated with a double gene construct expressing both P53 and Bc1-2. PC is the untreated control mice. As shown in the table in FIGS. 14A-14C, the mice were injected with the constructs and their tumor size measured. Injection days were Days 0, 5, 9, 14 and 21. Tumor size measurement days were Days 7, 12, 16, 21 and 28. Comparison of the tumor size of the V1, V2, V3 mice show that the tumor size in these mice were much reduced compared with the tumor size in the control PC mice. Comparison of the tumor weight on Day 28 in FIG. 14C indicates that V1, V2, V3 mice tumor weight were much reduced compared with the tumor weight in the control PC mice. The ratio of tumor weight/starting tumor size at day 7 shows a large difference in the V1, V2 and V3 Groups compared with that of the PC control mice.

V3 Group was injected with half of the dosage concentration compared with V1 and V2 Groups. Yet its tumor size is smaller than V2 and close to V1, thus indicating the synergistic effect of V3.

Example 7—Treatment of Human Patients with SIN-HIV-CMV-p53-hPSA-RNAihuCD25

To investigate the combination gene therapy effects of our gene vector for treatment of human metastatic prostate cancer, adult bone marrow cells (BMC) genetically modified by transduction with SIN-HIV-CMV-p53-hPSA-RNAi-huCD25 (FIG. 1C, Panel C, lower construct) are administered to patients with metastasized prostate cancer by the following procedure: (1) blood is harvested from the patient to collect stem cells. Recent medical advances now make it possible to collect stem cells from circulating blood as well. The collection or harvesting of bone marrow is typically done in a hospital operating room under general anesthesia. The bone marrow is then frozen and stored until gene therapy is completed. (2) The bone marrow cells are transduced ex vivo by the gene transfer vector expressing P53, RNAi and huCD25. To select only those cells stems transduced by the transfer vector, cells expressing the selectable marker huCD25 are selected. Stem cell selection is one method used for purging tumor cells. Recent clinical studies have demonstrated that stem cell selection reduces the tumor contamination found in mobilized blood. This is possibly because stem cells have unique properties not shared by tumor cells. (3) After evaluation of the transduced stem cells, and marker selection, the stem cells are thawed and returned to the patient. This procedure is often referred to as the transplant. Within a few days after completing the gene therapy, the stored stem cells are transplanted, or re-infused into the patient's bloodstream. The re-infusion process is similar to a blood transfusion and takes place in the patient's room: it is not a surgical procedure. The frozen bags of bone marrow or blood cells are thawed in a warm water bath, and then injected into the bloodstream through the catheter. It usually takes 2-4 hours for the infusion. Infused stem cells travel through the bloodstream, and eventually, to the bone marrow where they begin to produce new white blood cells, red blood cells, and platelets. (3) The patients are evaluated by collection of their blood to determine the level of P53, Bc1-2, and the selectable marker (i.e., huCD25) at different time points following treatment using Real Time PCR. At the same time a routine diagnosis of index is done to see if any indexes of cancer markers disappear in the current clinical settings.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A lentiviral transfer system comprising:
a self-inactivating transfer vector comprising:
  (a) multiple gene units, wherein each gene unit comprises a heterologous nucleic acid sequence operably linked to a regulatory nucleic acid sequence; and
  (b) a mammalian insulator sequence and splice acceptor and donor sites,
wherein the self-inactivating transfer vector is free of wPRE (wood-chuck hepatitis virus post-transcriptional element).

2. The lentiviral transfer system of claim 1, further comprising an envelope construct for providing a functional env protein.

3. The lentiviral transfer system of claim 1, wherein the multiple gene units comprise a first gene unit operably linked to a first regulatory nucleic acid sequence and a second gene unit operably linked to a second regulatory nucleic acid sequence.

4. The lentiviral transfer system of claim 3, wherein at least one of the first gene unit or the second gene unit encodes a trafficking signal.

5. The lentiviral transfer system of claim 1, wherein the regulatory nucleic acid sequence comprises a cell-specific or tissue-specific promoter.

6. The lentiviral transfer system of claim 5, wherein the cell or tissue-specific promoter is selected from: TSTA promoter, mesothelin promoter, hPSA promoter, hCCKAR promoter, hAFP promoter, and hNSE promoter.

7. The lentiviral transfer system of claim 6, wherein the heterologous nucleic acid sequence encodes at least one RNAi agent or at least one polypeptide that inhibits expression of Bcl-2.

8. A pharmaceutical composition comprising a lentiviral particle for gene transfer, said lentiviral particle produced using a lentiviral transfer system comprising:
a self-inactivating transfer vector comprising:
  (a) multiple gene units, wherein each gene unit comprises a heterologous nucleic acid sequence operably linked to a regulatory nucleic acid sequence; and
  (b) a mammalian insulator sequence and splice acceptor and donor sites,
wherein the self-inactivating vector is free of wPRE (wood-chuck hepatitis virus post-transcriptional element).

9. The pharmaceutical composition of claim 8, further comprising an envelope construct for providing a functional env protein.

10. The pharmaceutical composition of claim 8, wherein the multiple gene units comprise a first gene unit operably linked to a first regulatory nucleic acid sequence and a second gene unit operably linked to a second regulatory nucleic acid sequence.

11. The pharmaceutical composition of claim 10, wherein at least one of the first gene unit or the second gene unit encodes a trafficking signal.

12. The pharmaceutical composition of claim 8, wherein the regulatory nucleic acid sequence comprises a cell-specific promoter or tissue-specific promoter.

13. The pharmaceutical composition of claim 8, wherein the pharmaceutical composition further comprises a chemotherapeutic agent or a steroid agent.

14. The pharmaceutical composition of claim 8, wherein the heterologous nucleic acid sequence encodes at least one RNAi agent or at least one polypeptide that inhibits expression of Bcl-2.

\* \* \* \* \*

SEQUENCE LISTING

```
<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<223> OTHER INFORMATION: transport motif

<400> SEQUENCE: 1

Arg Ser Ala Ser Arg
1               5

<210> SEQ ID NO 2
<211> LENGTH: 5
<212> TYPE: PRT
<213> ORGANISM: Artificial Sequence
<220> FEATURE:
<223> OTHER INFORMATION: transport motif

<400> SEQUENCE: 2

Arg Thr Ala Ser Arg
1               5

<210> SEQ ID NO 3
<211> LENGTH: 5
<212> TYPE: PRT
<213> ORGANISM: Artificial Sequence
<220> FEATURE:
<223> OTHER INFORMATION: transport motif

<400> SEQUENCE: 3

Arg Ser Arg Ala Arg
1               5

<210> SEQ ID NO 4
<211> LENGTH: 5
<212> TYPE: PRT
<213> ORGANISM: Artificial Sequence
<220> FEATURE:
<223> OTHER INFORMATION: transport motif

<400> SEQUENCE: 4

Arg Thr Arg Ala Arg
1               5

<210> SEQ ID NO 5
<211> LENGTH: 5
<212> TYPE: PRT
<213> ORGANISM: Artificial Sequence
<220> FEATURE:
<223> OTHER INFORMATION: transport motif

<400> SEQUENCE: 5

Ala Thr Ala Thr Arg
1               5

<210> SEQ ID NO 6
<211> LENGTH: 6
<212> TYPE: PRT
<213> ORGANISM: Artificial Sequence
<220> FEATURE:
<223> OTHER INFORMATION: transport motif

<400> SEQUENCE: 6

Arg Ser Ala Ala Ser Arg
1               5
```

<210> SEQ ID NO 7
<211> LENGTH: 9
<212> TYPE: PRT
<213> ORGANISM: Artificial Sequence
<220> FEATURE:
<223> OTHER INFORMATION: tat derived peptide

<400> SEQUENCE: 7

Gly Arg Lys Lys Arg Arg Gln Arg Arg
1               5

<210> SEQ ID NO 8
<211> LENGTH: 33
<212> TYPE: DNA
<213> ORGANISM: Artificial Sequence
<220> FEATURE:
<223> OTHER INFORMATION: nucleic acid encoding tat derived peptide

<400> SEQUENCE: 8
tatggcagga agaagcggag acagcgacga aga                                33

<210> SEQ ID NO 9
<211> LENGTH: 11
<212> TYPE: PRT
<213> ORGANISM: Artificial Sequence
<220> FEATURE:
<223> OTHER INFORMATION: tat derived peptide

<400> SEQUENCE: 9

Tyr Gly Arg Lys Lys Arg Arg Gln Arg Arg
1               5                   10

<210> SEQ ID NO 10
<211> LENGTH: 11
<212> TYPE: PRT
<213> ORGANISM: Artificial Sequence
<220> FEATURE:
<223> OTHER INFORMATION: tat derived peptide

<400> SEQUENCE: 10

Tyr Ala Arg Ala Ala Ala Arg Gln Ala Arg Ala
1               5                   10

<210> SEQ ID NO 11
<211> LENGTH: 11
<212> TYPE: PRT
<213> ORGANISM: Artificial Sequence
<220> FEATURE:
<223> OTHER INFORMATION: tat derived peptide

<400> SEQUENCE: 11

Thr His Arg Leu Pro Arg Arg Arg Arg Arg
1               5                   10

<210> SEQ ID NO 12
<211> LENGTH: 11
<212> TYPE: PRT
<213> ORGANISM: Artificial Sequence
<220> FEATURE:
<223> OTHER INFORMATION: tat derived peptide

<400> SEQUENCE: 12

Gly Gly Arg Arg Ala Arg Arg Arg Arg Arg
1               5                   10

```
<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
agctagatag tgtcacctaa atgc                                              24

<210> SEQ ID NO 14
<211> LENGTH: 15
<212> TYPE: DNA
<213> ORGANISM: Artificial Sequence
<220> FEATURE:
<223> OTHER INFORMATION: Primer

<400> SEQUENCE: 14
agcatgcctg ctatt                                                        15
```